United States Patent
Murtha, III

(10) Patent No.: US 11,969,313 B1
(45) Date of Patent: Apr. 30, 2024

(54) SURGICAL PROCEDURES FOR REPAIRING AND STABILIZING AN INJURED CRANIAL CRUCIATE LIGAMENT IN THE CANINE STIFLE JOINT

(71) Applicant: Thomas J. Murtha, III, North Andover, MA (US)

(72) Inventor: Thomas J. Murtha, III, North Andover, MA (US)

(*) Notice: Subject to any disclaimer, the term of this patent is extended or adjusted under 35 U.S.C. 154(b) by 0 days.

(21) Appl. No.: 18/523,138

(22) Filed: Nov. 29, 2023

Related U.S. Application Data

(60) Provisional application No. 63/385,425, filed on Nov. 30, 2022.

(51) Int. Cl.
*A61D 1/00* (2006.01)
*A61F 2/08* (2006.01)
*A61B 17/06* (2006.01)

(52) U.S. Cl.
CPC .............. *A61D 1/00* (2013.01); *A61F 2/0811* (2013.01); *A61B 2017/06023* (2013.01)

(58) Field of Classification Search
CPC ....... A61D 1/00; A61F 2/0811; A61F 2/0805; A61F 2/08; A61F 2002/0882; A61F 2002/0888; A61F 2250/0081; A61B 2017/06023
See application file for complete search history.

(56) References Cited

U.S. PATENT DOCUMENTS

| | | | |
|---|---|---|---|
| 6,764,513 B1 * | 7/2004 | Dowling | A61F 2/08 623/13.14 |
| 2002/0120280 A1 * | 8/2002 | Wotton, III | A61B 17/0487 606/148 |
| 2008/0195148 A1 * | 8/2008 | Cook | A61D 1/00 606/228 |
| 2012/0065732 A1 * | 3/2012 | Roller | A61B 17/0487 606/232 |

* cited by examiner

*Primary Examiner* — Dianne Dornbusch
(74) *Attorney, Agent, or Firm* — Matthew M. Yospin

(57) ABSTRACT

A surgical procedure for repairing and stabilizing an injured (torn, partially torn, or otherwise injured) cranial cruciate ligament in the canine stifle joint. The procedure strategically implants multiple filaments with increased tensile strength along multiple separate extra-capsular loading pathways that divide and distribute the load on the canine's stifle joint in different planes and directions for greater overall stability and strength of the repair. The filaments are anchored at multiple strategic points to stabilize the canine stifle joint. The repaired stifle joint requires multiple points of failure in the implanted filaments for the procedure to fail.

16 Claims, 47 Drawing Sheets

SURGICAL PROCEDURES FOR REPAIRING AND STABILIZING AN INJURED CRANIAL CRUCIATE LIGAMENT IN THE CANINE STIFLE JOINT

FIELD OF THE INVENTION

This invention relates to a surgical procedure for repairing and stabilizing an injured (torn, partially torn, or otherwise injured), cranial cruciate ligament in the canine stifle joint.

BACKGROUND OF INVENTION

The stifle joint of the dog is equivalent to a human's knee. The cranial cruciate ligament (CCL) is located inside the joint and is responsible for maintaining its stability. This cranial cruciate ligament is similar to the anterior cruciate ligament (ACL) in humans.

Cranial cruciate ligament injuries, or tears, are by far the most common orthopedic injury in dogs. When the cranial cruciate ligament is injured (torn, partially torn, or otherwise injured), the shin bone (tibia) slides forward with respect to the thigh bone (femur), which is known as a positive drawer sign. Most dogs with this injury cannot walk normally and experience pain. The resulting instability damages the cartilage and surrounding bones and leads to osteoarthritis (OA).

Once such an injury occurs, a surgical procedure is needed that repairs and stabilizes the canine stifle joint after the patient has injured (torn, partially torn, or otherwise injured), its cranial cruciate ligament. Only surgery can restore proper limb stability and function.

The most commonly performed surgical procedures today are osteotomy or bone cutting surgical procedures, Tibial Plateau Leveling Osteotomy (TPLO), such as the procedure disclosed in U.S. Pat. No. 4,677,973 to Slocum, granted 1987 ("Proximal, tibial osteotomy for leveling a tibial plateau"), and Tibial Tuberosity Advancement (TTA).

The Tibial Plateau Leveling Osteotomy (TPLO) surgical procedure changes the angle and relationship of the femur and the tibia. A semicircular cut is made through the top of the tibia, rotating the top of the tibia, and using a bone plate to allow the tibia to heal. This realignment of the surfaces within the stifle helps to provide stability during a stride and helps to reduce future joint inflammation.

In the Tibial Tuberosity Advancement (TTA) surgical procedure, the front part of the tibia is cut and separated from the rest of the tibia. An orthopedic spacer is screwed into the space between the two sections of bone to slide the front part of the lower knee forward and up. This moves the patella ligament into better alignment, thereby removing some of the abnormal sliding movement. A bone plate is then attached to hold the front section of the tibia in the proper position. By changing the alignment of the patella ligament, the forces that cause the femur to slip backward when the cranial cruciate ligament is torn instead move straight down the tibia, resulting in less shearing force or instability.

The Tibial Plateau Leveling Osteotomy (TPLO) and Tibial Tuberosity Advancement (TTA) surgical procedures have high complication rates, high opposite limb cranial cruciate ligament tear rates and, because they cause substantial trauma to the bone, they have been associated with the development of neoplastic changes (osteosarcoma or bone cancer) at the surgical site post-operatively over time. TPLO and TTA are highly traumatic surgical procedures that involve cutting of bone, reorientation or re-leveling of the bone, and metal plating of the bone. Recovery from these osteotomy surgical procedures is prolonged and difficult and the resultant off-loading of the surgically repaired limb (onto and double-loading the opposite limb) likely contributes significantly to the high opposite limb cranial cruciate ligament tear rates associated with these procedures.

Research and publications on the topic of surgical procedures for repair and stabilization of the canine stifle joint include "A Comparative Study of the Length Patterns of Anterior Cruciate Ligament Reconstructions in the Dog and Man" (M. P. Palmisano et. al, Vet. Comp. Orthop. Traumatol. 2000; 13: 73-77), "Isometry of potential suture attachment sites for the cranial cruciate ligament deficient canine stifle" (S. C. Roe et. al, Vet. Comp. Orthop. Traumatol. 2008: 3, 215-220), "Determination of isometric points for placement of a lateral suture in treatment of the cranial cruciate ligament deficient stifle" (D. Hulse et. al, Vet. Comp. Orthop. Traumatol. 2010; 3: 163-167), and "Determination of Isometric Points in the Stifle of a Dog Using a 3D Model" (N. Yair et. al, Vet. Comp. Orthop. Traumatol. 2023, published online 2023-07-24). The present disclosure presents surgical methods for creating and maintaining isometric tension in a stifle joint throughout the range of motion of the stifle joint.

Prior surgical procedures attempt to "reinvent the wheel" and are based on the premise that the anatomy of the canine stifle joint is defective and that this defective anatomy is the underlying cause for most canine cranial cruciate ligament tears. The TPLO and TTA surgical procedures effectively attempt to redesign the anatomy of the canine stifle joint and re-engineer the biomechanics of the joint (how the joint works) without anything assuming the role of the cranial cruciate ligament. As a result, there is a complete contrast and dichotomy between the new biomechanics of the surgically repaired limb (how it moves and functions), compared to how the opposite limb moves and functions using the natural biomechanics that have evolved over time. This creates an obvious and significant asymmetry in the recovering patient's bilateral movement and gait. The repaired limb moves this new way and relies on a metal implant for stability, while the other limb moves the old, natural way, and relies on a natural ligament comprised of collagen fibers for stability. This unnatural and significant asymmetry creates mechanical stress points not only within each of the stifle joints, but at various points along each extremity (along each hind limb) and quite likely affecting the hips, the spine, and perhaps the forelimbs as well.

Most TPLO and TTA surgical patients exhibit prolonged off-loading of the surgically repaired limb during the post-operative recovery period, resulting in an overload of the opposite, nonsurgical, stifle joint and cranial cruciate ligament that is forced to carry and support all the additional load shifted from the surgically repaired limb. The cumulative effect of the overloading of the opposite limb stifle joint and cranial cruciate ligament along with the forces associated with the asymmetrical gait and resultant awkward movement consistently come to bear on the opposite (non-surgical) stifle joint is that these combined forces quickly become overwhelming, and often, the opposite limb cranial cruciate ligament tears as well.

Other surgical procedures used to correct cranial cruciate ligament injuries include the Extracapsular Lateral Suture Stabilization and Tightrope surgeries. These are both extra-capsular procedures that attempt to re-stabilize the existing anatomy of the canine stifle joint.

One prior art procedure, sometimes referred to as extra-capsular Lateral Suture Stabilization (ELSS), is another surgical procedure that attempts to provide stability to the unstable canine knee. In this procedure, a strong single monofilament suture (comprised of various materials ranging in tensile strength) is placed from the lateral fabella to the tibial crest, to re-establish a connection between the tibia and the femur with the intent to re-stabilize the stifle joint. This suture limits cranial translation of the tibia relative to the femur and maintains normal range of motion in the knee.

One prior art procedure, sometimes referred to as the TightRope surgical procedure, requires drilling two bone channels; one from side to side through the tibia and the other from side to side through the femur, to run a strong single monofilament suture through, thereby stabilizing the joint. This procedure uses bone anchors to reduce the need for additional suture material in and/or around the joint.

The Extracapsular Lateral Suture Stabilization and Tightrope surgeries distribute the entire load (weight and force) coming to bear on the patient's stifle joint (and thus on the implanted filament) in a single direction or plane, which allows for greater instability as the stifle joint moves through its range of motion, consequently overloading the filament. The entire load on the patient's stifle joint is carried by a single filament along a single plane and direction (or loading pathway), and this requires only a single point of failure for the surgical procedure itself to fail. If this single filament should slacken, loosen, or break, the stifle joint becomes unstable once again and the surgical procedure has failed. The potential for overloading of the single filament can lead to compromise of the structural integrity of the filament, instability, and ultimately failure of the filament and the surgical procedure.

The subject invention is a surgical procedure based on the premise that the anatomy and biomechanics of the canine stifle joint are what they should be, and what they have evolved to be over many hundreds of thousands of years. The surgical procedure of the subject invention effectively re-stabilizes the existing anatomy of the canine stifle joint, reinforcing what mother nature created in the first place and allowing normal and symmetrical use of the injured limb once again, by creating and maintaining isometric tension in a stifle joint throughout the range of motion of the stifle joint. This allows for a faster and easier recovery from surgery and provides consistently superior results without the substantially higher postoperative opposite limb cranial cruciate ligament tear rates associated with osteotomy surgeries and without the other problems, issues and complications commonly associated with the TPLO and TTA surgical procedures.

The surgical procedure of the subject invention strategically implants multiple filaments of monofilament nylon, or other suitable material, having a combined tensile strength that is eight to ten times the load (weight and force) that comes to bear on the patient's stifle joint. Multiple filaments are implanted along two separate extra-capsular loading pathways that divide and distribute the load (weight and force) on the patient's stifle joint in different planes and directions (both vertically and horizontally) for greater overall stability and strength of the repair and requiring multiple points of failure for the procedure itself to fail. This over-engineering allows for failure of one or more filaments without compromising the overall strength and integrity of the surgical repair.

The present disclosure further discloses an improved surgical stacking needle, suitable for surgeries on any animals, where the surgery requires or is facilitated by the use of a needle with the capability to hold and use multiple filaments at a time. The needle may be disposed with an enlarged eye, or with one or more eyes, or with enlarged eye or eyes. With multiple eyes, the needle comprises multiple eye-separators, to separate the eyes from other eyes, and to support the needle in the head area of the needle. Such a surgical stacking needle, which may also be referred to as a "curved elongated eye stacking needle" or a "straight elongated eye stacking needle" or an "elongated eye stacking needle" may be used to facilitate surgeries such as those further described herein, or other surgeries requiring multiple filaments.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses a method of stabilizing a cranial cruciate ligament deficient stifle, the method comprising the steps of: implanting one or more filaments along at least two separate extra-capsular loading pathways on the stifle, wherein each pathway comprises a different directional plane; anchoring the filaments in at least four points proximate to the canine stifle; wherein failure of the stabilized (after being injured) canine cranial cruciate ligament requires a plurality of points of failure in the implanted one or more filaments. An object of the present disclosure is to disclose surgical methods for creating and maintaining isometric tension in a stifle joint throughout the range of motion of the stifle joint.

The subject invention also discloses a method for repairing an injured canine cranial cruciate ligament, the method comprising the steps of: implanting one or more filaments along at least two separate extra-capsular loading pathways on a canine stifle proximate to the cranial cruciate ligament, wherein each pathway comprises a different directional plane; anchoring the filaments in at least four points proximate to the canine stifle; wherein failure of the repaired injured canine cranial cruciate ligament requires a plurality of points of failure in the implanted one or more filaments.

The subject invention further discloses a method for repairing an injured canine cranial cruciate ligament in a stifle, the method comprising the steps of: drilling a first hole and a second hole in a tibial tuberosity extending from a lateral side to a medial side; inserting a first needle behind the lateral fabella, circumnavigating around the lateral fabella at substantially a forty-five degree angle to a horizontal plane and exiting the lateral fabella; threading an eye of the first needle with one or more filaments, each with a first and second end; circumnavigating the first needle containing (meaning having or holding, after the eye has been threaded with the one or more filaments) the one or more filaments around the lateral fabella at an angle substantially forty-five degrees to the horizontal plane, until the first needle and filaments can be pulled free in a lateral direction from the stifle; cutting each filament within the first needle at an apex centered at the needle eye to create a third end and a fourth end for each filament; threading a first portion of the one or more filaments through an eye of a second needle, each of the one or more filaments having a first end and a second end; passing the second needle through the first (proximal) hole in the tibial tuberosity from the lateral side to the medial side; passing the second needle through the second (distal) hole in the tibial tuberosity from the medial side to the lateral side; pairing and clasping the first and second ends of each filament with a corresponding third end and fourth end of each filament; threading substantially a remaining portion of the one or more filaments through the eye of the second needle through the first and second ends of each filament; passing the second needle through the first hole in the tibial tuberosity from the lateral side to the medial side; carrying the second needle at angle between thirty to forty-five degrees through a soft fascia tissue on a medial aspect of a patella ligament, exiting and crossing over a cranial border of, that is, just behind, the patella ligament, through a fascia tissue on a lateral aspect of the patella ligament and carried through a lateral fascia of the a biceps femoris muscle; pairing and clasping the first and second ends of each filament with the corresponding third end and fourth end of each filament where a filament was cut into filament portions and the filament portions are paired; pulling the one or more filaments substantially tight; and connecting the first and second ends of each filament with the corresponding third end and fourth end of each filament, wherein filaments comprising a craniomedial pathway must be connected first, wherein within each pathway, the filaments having greater diameter must be connected first.

The subject invention also discloses a method for repairing an injured canine cranial cruciate ligament in a stifle, the method comprising the steps of: drilling a first (proximal) hole in a tibial tuberosity by entering the tibial tuberosity on a lateral side and exiting the tibial tuberosity on a medial side; drilling a second (distal) hole in the tibial tuberosity by entering the tibial tuberosity on the lateral side and exiting the tibial tuberosity on the medial side; inserting a curved needle behind the caudal-ventral aspect of the lateral fabella, circumnavigating around the lateral fabella at substantially a forty-five degree angle to a horizontal plane and exiting at a cranial-dorsal aspect of the lateral fabella; threading an eye of the curved needle with one or more filaments, each with a first and second end; balancing a substantially equal length of each filament on either side of the eye of the curved needle; circumnavigating the curved needle containing (meaning having or holding, after the eye has been threaded with the one or more filaments) the one or more filaments around the lateral fabella at an angle substantially forty-five degrees to the horizontal plane, until the curved needle and filaments can be pulled free in a lateral direction from the stifle; cutting each filament within the eye of the curved needle at a filament apex to create a third end and a fourth end for each filament; threading substantially a first half, or other suitable number or portion, of the one or more filaments through an eye of a substantially straight second needle such that the first and second ends of each filament are approximately near each other; passing the second needle through the first (proximal) hole in the tibial tuberosity from the lateral side to the medial side; passing the second needle through the second (distal) hole in the tibial tuberosity from the medial side to the lateral side; pairing and clasping the first and second ends of each filament with a corresponding third end and fourth end of each filament; threading substantially a second half, or other suitable number or portion, of the one or more filaments through the eye of the second needle through the first and second ends of each filament; passing the second needle through the first (proximal) hole in the tibial tuberosity from the lateral side to the medial side; carrying the second needle at angle between thirty to forty-five degrees through a soft fascia tissue on a medial aspect of a patella ligament, exiting and crossing over a cranial border behind the patella ligament, through a fascia tissue on a lateral aspect of the patella ligament and carried through a lateral fascia of the a biceps femoris muscle; pairing and clasping the first and second ends of each filament with the corresponding third end and fourth end of each filament; pulling the one or more filaments substantially tight; and connecting the first and second ends of each filament with the corresponding third end and fourth end of each filament, wherein filaments comprising a craniomedial pathway must be connected first, wherein within each pathway, the filaments having greater diameter must connected first.

The subject invention additionally discloses a method for repairing an injured canine cranial cruciate ligament in a stifle, the method comprising the steps of: drilling a first (proximal) hole in a tibial tuberosity by entering the tibial tuberosity on a lateral side and exiting the tibial tuberosity on a medial side; drilling a second (distal) hole in the tibial tuberosity by entering the tibial tuberosity on the lateral side and exiting the tibial tuberosity on the medial side; exposing a lateral fabella from a biceps femoris muscle; inserting a curved elongated eye stacking needle behind the caudal-ventral aspect of the lateral fabella, circumnavigating around the lateral fabella at substantially a forty-five degree angle to a horizontal plane and exiting at the cranial-dorsal aspect of the lateral fabella; holding a needle point of the curved elongated eye stacking needle; holding an other end of the curved elongated eye stacking needle, proximate to an eye of the curved elongated eye stacking needle; threading the eye of the needle with one or more filaments, wherein the one or more filaments are vertically stacked within the eye of the curved elongated eye stacking needle; balancing a substantially equal length of each filament on either side of the eye of the curved elongated eye stacking needle; clasping opposite ends of each filament, such as the first end and the second end of each filament; circumnavigating the curved elongated eye stacking needle containing (meaning having or holding, after the eye has been threaded with the one or more filaments) the one or more filaments behind and around the lateral fabella at an angle substantially forty-five degrees to the horizontal plane, until the curved elongated eye stacking needle and filaments can be pulled free in a lateral direction from the stifle; cutting each filament within the eye of the curved elongated eye stacking needle at a filament apex to create a third end and a fourth end for each filament; clasping the third end and fourth end of each filament; threading substantially a first half, or other suitable number or portion, of the one or more filaments through an eye of a straight elongated eye stacking needle, which may be substantially or approximately straight, such that the first and second ends of each filament are approximately near each other; passing the straight elongated eye stacking needle through the first (proximal) hole in the tibial tuberosity from the lateral side to the medial side; passing the straight elongated eye stacking needle through the second (distal) hole in the tibial tuberosity from the medial side to the lateral side; pairing and clasping the first and second ends of each filament with a corresponding third end and fourth end of each filament; threading substantially a second half, or other suitable number or portion, of the one or more filaments through the eye of the substantially straight elongated eye stacking needle through the first and second ends of each filament; passing the straight elongated eye stacking needle through the first (proximal) hole in the tibial tuberosity from the lateral side to the medial side; carrying the straight elongated eye stacking needle at angle between thirty to forty-five degrees through a soft fascia tissue on a medial aspect of a patella ligament, exiting and crossing over a cranial border behind the patella ligament, through a fascia tissue on a lateral aspect of the patella ligament and carried through a lateral fascia of a biceps femoris muscle; pairing and clasping the first and second ends of each filament with the corresponding third end and fourth end of each filament; pulling the one or more filaments substantially tight; and connecting the first and second ends of each filament with the corresponding third end and fourth end of each filament, wherein filaments comprising a craniomedial pathway must be connected first, wherein within each pathway, the filaments having greater diameter must connected first.

In further embodiments of the subject invention, the first hole is proximal to a proximal-lateral aspect of the tibial tuberosity;

In other embodiments of the subject invention, the second hole is proximal to a vertical midpoint of the tibial tuberosity.

In additional embodiments of the subject invention, the one or more filaments comprise a monofilament nylon.

In embodiments of the subject invention, the one or more filaments comprise an increased tensile strength of eight to ten times the load that comes to bear on the canine's stifle.

In other embodiments of the subject invention, the stifle joint after being repaired requires multiple points of failure in the implanted one or more filaments for the method to fail.

In further embodiments of the subject invention, the first portion of the one or more filaments is distributed along a craniomedial pathway, distributing a load more proximally and along both the vertical and horizontal planes.

In embodiments of the subject invention, the remaining portion of the one or more filaments is distributed along a caudolateral pathway which distributes the load more distally and vertically along a lateral-vertical plane.

In additional embodiments of the subject invention, the second hole is one to four centimeters from the first hole.

In other embodiments of the subject invention, the first and second holes comprise a diameter of three to six millimeters.

In further embodiments of the subject invention, each filament may be forty-eight inches long.

In additional embodiments of the subject invention, the tensile strength of each filament may be selected from a group comprising 40-pound, 60-pound, and 80-pound, also written or referred to as 40 #, 60 #, and 80 #.

In embodiments of the subject invention, the terms "substantially" and "approximately" are defined as at least close to (and can include) a given value or state, as understood by a person of ordinary skill in the art. In one embodiment, the term "substantially" refers to ranges within 10%, preferably within 5%, more preferably within 1%, and most preferably within 0.1% of the given value or state being specified. Where ranges are provided, the foregoing applies to both the start and end of the range of values given.

In embodiments of the subject invention, the term "relatively" is defined as a comparison of a property, or the proportion of a property between two components.

BRIEF DESCRIPTION OF THE DRAWINGS

Advantages of the present invention will be apparent from the following detailed description of embodiments, which description should be considered in conjunction with the accompanying drawings, in which.

DETAILED DESCRIPTION OF THE EMBODIMENTS

Figure 1:
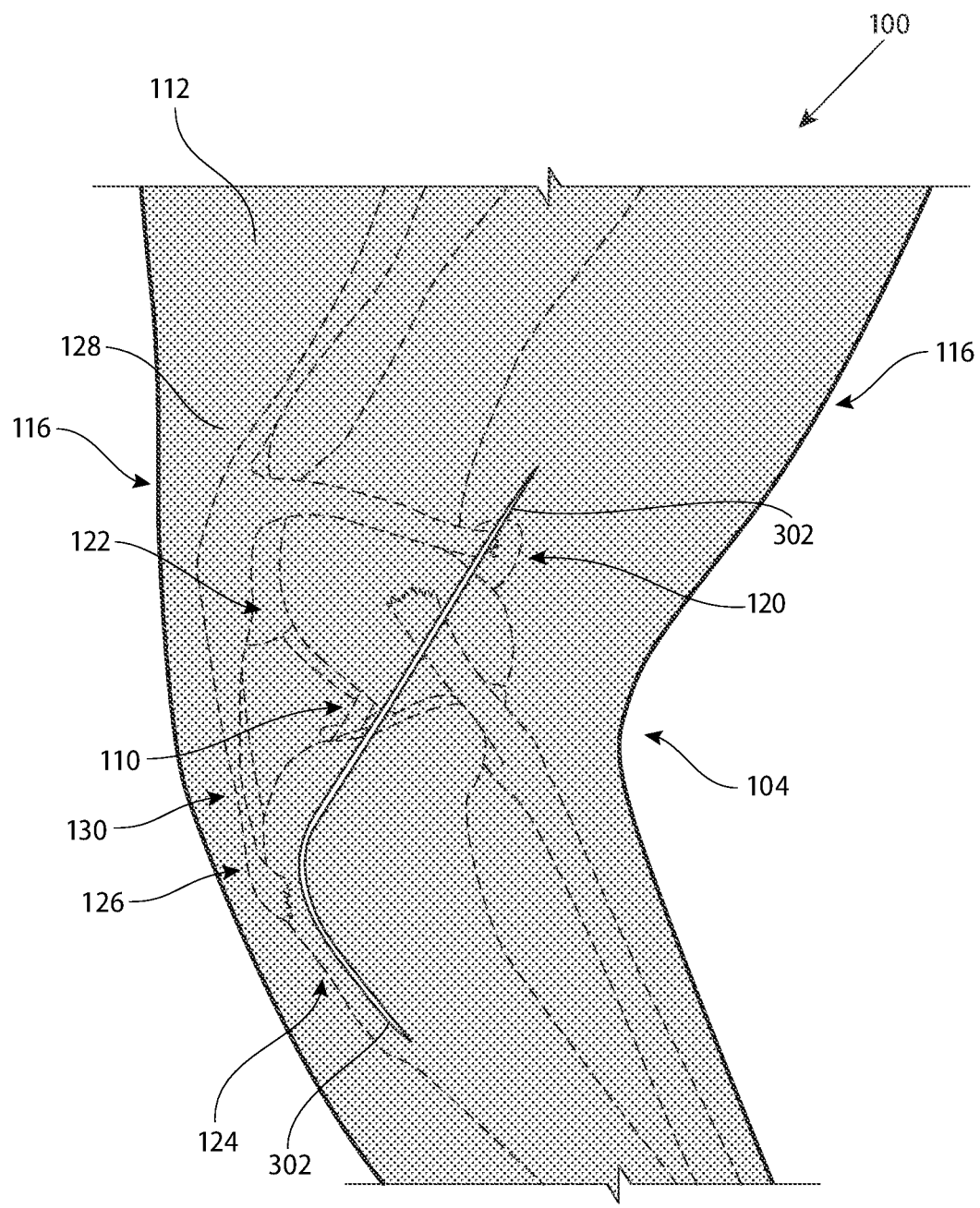
FIG. 1 illustrates a lateral view of the main ligaments and tendons of the canine stifle with a first skin incision originating dorsal to the lateral fabella, continuing distally to the tibial tuberosity, then curving ventrally and parallel to the tibial tuberosity.

The presently disclosed invention is described with specificity to meet statutory requirements. But, the description itself is not intended to limit the scope of this patent. Rather, the claimed invention might also be configured in other ways, to include different steps or elements similar to the ones described in this document, in conjunction with other present or future technologies. Moreover, although the term "step" or similar terms may be used herein to connote different aspects of methods employed, the term should not be interpreted as implying any particular order among or between various steps herein disclosed unless and except when the order of individual steps is explicitly described.

In the following description, numerous specific details are set forth to provide a thorough understanding of the invention. But, the present invention may be practiced without these specific details. Structures and techniques that would be known to one of ordinary skill in the art have not been shown in detail, in order not to obscure the invention. Referring to the figures, it is possible to see the various major elements constituting the apparatus, systems, and methods of use of the present invention.

The subject invention discloses a minimally-invasive veterinary orthopedic surgical procedure for repairing and stabilizing a canine stifle joint 104 of a canine 100, also referred to herein as a dog, after the canine 100 has injured (torn, partially torn, or otherwise injured), a cranial cruciate ligament 110 (CCL). The surgical procedure taught herein comprises multiple improvements over a prior surgical technique for repairing or stabilizing an injured canine cranial cruciate ligament in a stifle. The present disclosure presents surgical methods for creating and maintaining isometric tension in a stifle joint throughout the range of motion of the stifle joint. The cranial cruciate ligament is important to neutralize cranial tibial subluxation, as well as to neutralize internal rotation and hyperextension of the stifle. The cranial cruciate ligament consists of two bands (craniomedial and caudolateral) that biomechanically provide constant and consistent isometric tension throughout the entire range of motion of the stifle joint. The craniomedial band is taut in both flexion and extension, while the caudolateral band is only taut in extension. It is the duality of function provided by the two bands which comprise the cranial cruciate ligament that allows for constant and consistent isometric tension as the stifle joint moves throughout its entire range of motion. The surgical procedure of the present disclosure teaches implanting multiple filaments along two separate load distribution pathways to reconnect the tibia and femur at strategic points, dividing and effectively distributing the load (weight and force) along both a craniomedial pathway (also referred to as an upper pathway, or as a proximal horizontal pathway) and a caudolateral pathway (also referred to as a lower pathway, or as a distal lateral vertical pathway). Dividing and distributing the load carried by the implanted filaments along two separate load distribution pathways not only imparts a greater level of strength and endurance to the surgical repair of the present disclosure, doing so effectively replicates the same duality of function and stabilizing effect previously provided by the cranial cruciate ligament. The strategic placement and anchoring of the implanted filaments at points on both the tibia and femur to create both the craniomedial pathway and caudolateral pathway load distribution pathways effectively replicates the same function and stabilizing effect previously provided by the cranial cruciate ligament, thus restoring more natural stifle biomechanics, and allowing for constant and consistent isometric tension throughout the stifle joint's entire range of motion.

The surgical procedure 300 strategically implants one or more filaments 210, where each of the one or more filaments 210 have a tensile strength 212, or in instances with more than one such filament, each of the said filaments can have a different tensile strength or the same tensile strength as other such filaments, in any combination, which is relatively increased, along one or more extra-capsular loading pathways 214, which is some aspects comprise at least two separate such pathways, that divide and distribute the load 106 (weight and force) on the stifle joint 104 of the patient in different planes and directions for greater overall stability and strength of the repair. The one or more filaments 210 are anchored at four strategic points to stabilize the canine stifle joint 104. The stifle joint 104, after being repaired, requires multiple points of failure in the one or more filaments 210 after the one or more filaments 210 are implanted, for the stifle joint 104, after being repaired, and the surgical procedure 300 to fail.

In embodiments of the subject invention, the one or more filaments 210 may each have or comprise a tensile strength 212 of eight to ten times the load 106 that comes to bear on the stifle joint 104 of the patient. In embodiments of the subject invention, the one or more filaments 210 are implanted in vertical planes 216 and in horizontal planes 218 of the one or more extra-capsular loading pathways 214.

Some portion of the load 106 that is carried by the one or more filaments 210 may be distributed along a craniomedial pathway 370, being proximal or dorsal, distributing a portion of the load 106 more proximally and along both the vertical planes 216 and the horizontal planes 218 (medial to lateral). In this embodiment, forty to fifty percent of the load 106 is distributed more proximally and along both the vertical planes 216 and the horizontal planes 218. The craniomedial pathway 370 may be referred to herein as an "upper pathway", a "proximal horizontal vertical pathway", or a "PHV pathway".

Some other, remaining, portion of the load 106 may be distributed more distally, along a caudolateral pathway 360, being distal or ventral, which distributes the remaining portion of the load 106 more distally and vertically along a lateral-vertical plane 219. In this embodiment, fifty to sixty percent of the load 106—the remaining portion thereof—is distributed more distally and vertically along the lateral-vertical plane 219. The caudolateral pathway 360 may be referred to herein as a "lower pathway", a "distal lateral vertical pathway", or a "DLV pathway".

Figure 27:
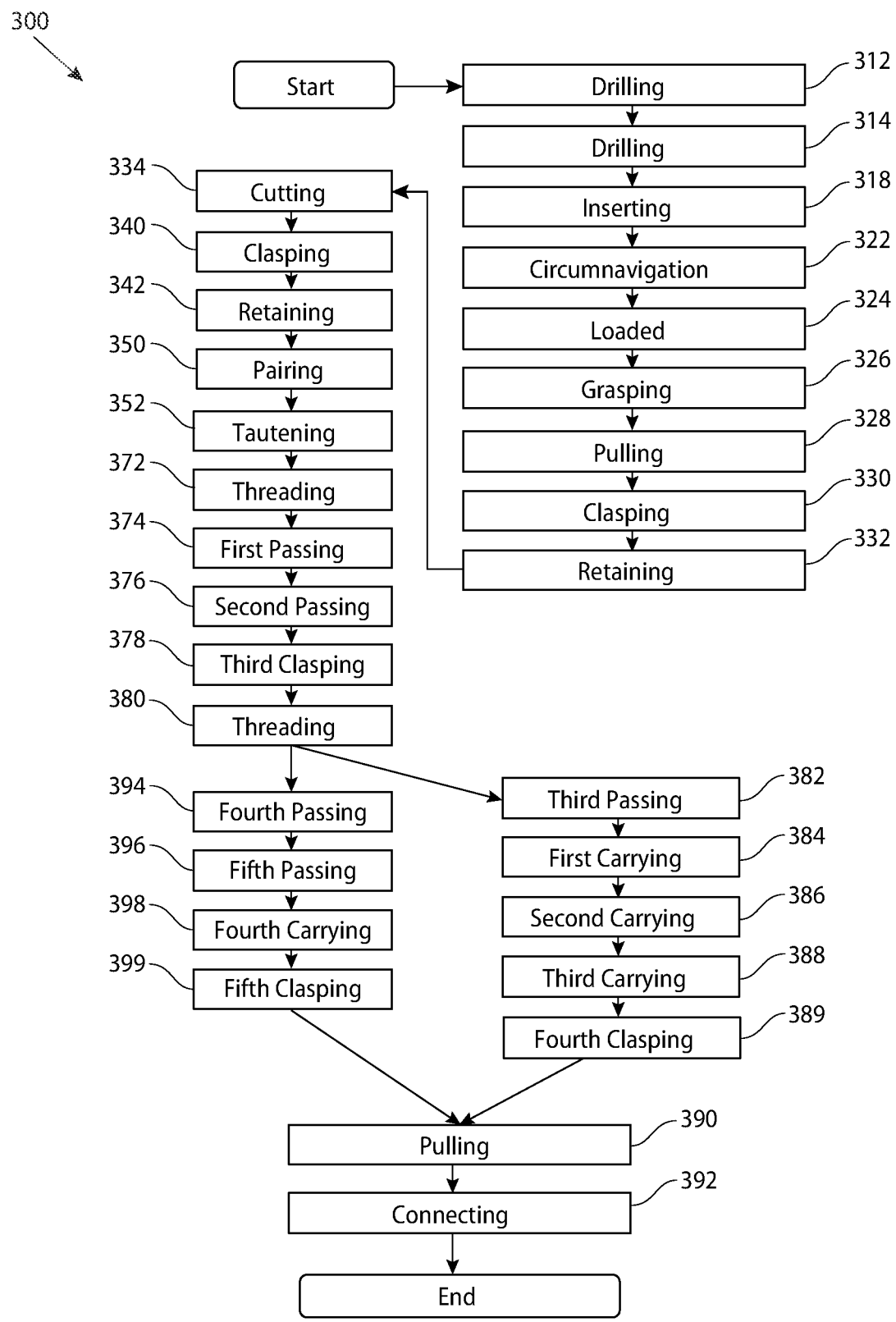
FIG. 27 illustrates embodiments of the methods of the present disclosure.

The faster and easier post-operative recovery after the surgical procedure 300, with reference to FIG. 27, is due to the surgical procedure 300 being a less invasive surgical procedure relative to the prior art, because the surgical procedure 300 simply re-stabilizes, reinforces, and restores the original anatomy and the natural biomechanics of the stifle joint 104. The restored limb is symmetrical with the natural biomechanics of the opposite limb of the canine 100, also referred to as a patient. This allows for the patient to be more fully weight-bearing on the surgically repaired limb sooner and minimizes off-loading of the patient's body weight from the surgically repaired limb over to the opposite limb for an extended period of time.

As a result, the cranial cruciate ligament 110 tear rate of the opposite limb of a canine 100 for this surgical procedure is in the range of thirteen to sixteen percent overall, as compared to TPLO and TTA surgical procedures having opposite limb tear rates of fifty to sixty percent in the first year alone and reports as high as seventy to eighty percent overall.

This surgical procedure employees strategic over-engineering and requires multiple points of failure for the stifle joint 104, after being repaired, and the surgical procedure itself, to fail. All of the one or more filaments 210, after being surgically implanted, must loosen, break, or fail for the stifle joint 104, after being repaired, to become unstable again.

In embodiments of the subject invention, the one or more filaments 210 may comprise a monofilament nylon. The one or more filaments 210, after being implanted, provoke the immune system to encapsulate or encase them in scar tissue over time (typically 6 to 12 months). The one or more filaments 210 become encased in scar tissue and this encasement reinforces the nylon of the one or more filaments 210 and strengthens the stifle joint 104 repair. Scar tissue is comprised of collagen, as are joint ligaments and tendons—while these are slightly different forms of collagen, they are collagen. The one or more filaments 210, after being implanted, provide a framework, or scaffolding, on which the body builds a new collagen ligament over time. The tensile strength 212 of the implanted materials is crucial and necessary for the first 6 to 12 months after surgery. Thereafter, a significant portion of the load 106 coming to bear on the stifle joint 104, after being repaired surgically, is or may be carried by the resulting scar tissue encasement and to a lesser degree the one or more filaments 210 at the encasement's core, underlying the resulting scar tissue. Thus, the surgical procedure 300 surgical repairs become stronger over time and it is very rare for the repair to lose its structural integrity with normal or routine use after six months post-op, requiring catastrophic type forces to compromise the repair. It has been found that the one or more filaments 210 may be removed at approximately 12 months post-operation, or advantageously, at approximately 18 months post-operation, or after a longer period post-operation, in cases where the patient (canine 100) is experiencing an aggressive immune response to the one or more filaments 210 that are implanted, that is, a rejection, leaving the stifle joint 104 stable after repair.

The surgical procedure is conducted comprising the following steps:

The canine 100 patient is placed in lateral recumbence with the hind limb to be surgically repaired, also referred to herein as a surgical limb 112, facing upward. The entire circumference of the surgical limb 112 is clipped and shaved from the hip joint distally to the hock joint. The lower extremities (the metatarsal area and digits distal to the hock joint) are taped with white adhesive tape to make an extended stirrup to suspend the limb to a fixed object above the surgical field.

The surgical limb 112 is then suspended, and after being suspended, is sterilely prepared for surgery. A large sterile surgical drape is placed over the opposite limb, wherein the opposite limb may be referred to herein as a non-surgical limb, and the surgical drape is secured to the proximal-most point of the medial aspect of the non-surgical limb using a towel clamp. The lower extremity of the surgical limb 112, which is suspended, is wrapped with a sterilized wrap product.

The wrapped lower extremity has the suspending tape cut, and is lowered onto the sterile surgical drape. The surgical limb 112 is draped off from the rest of the patient's body to create a sterile closed surgical field.

On the surgical limb 112 of the canine 100, a lateral fabella 120, a patella 122, and a proximal aspect 126 of a tibial tuberosity 124 are identified via palpation.

Figure 2:
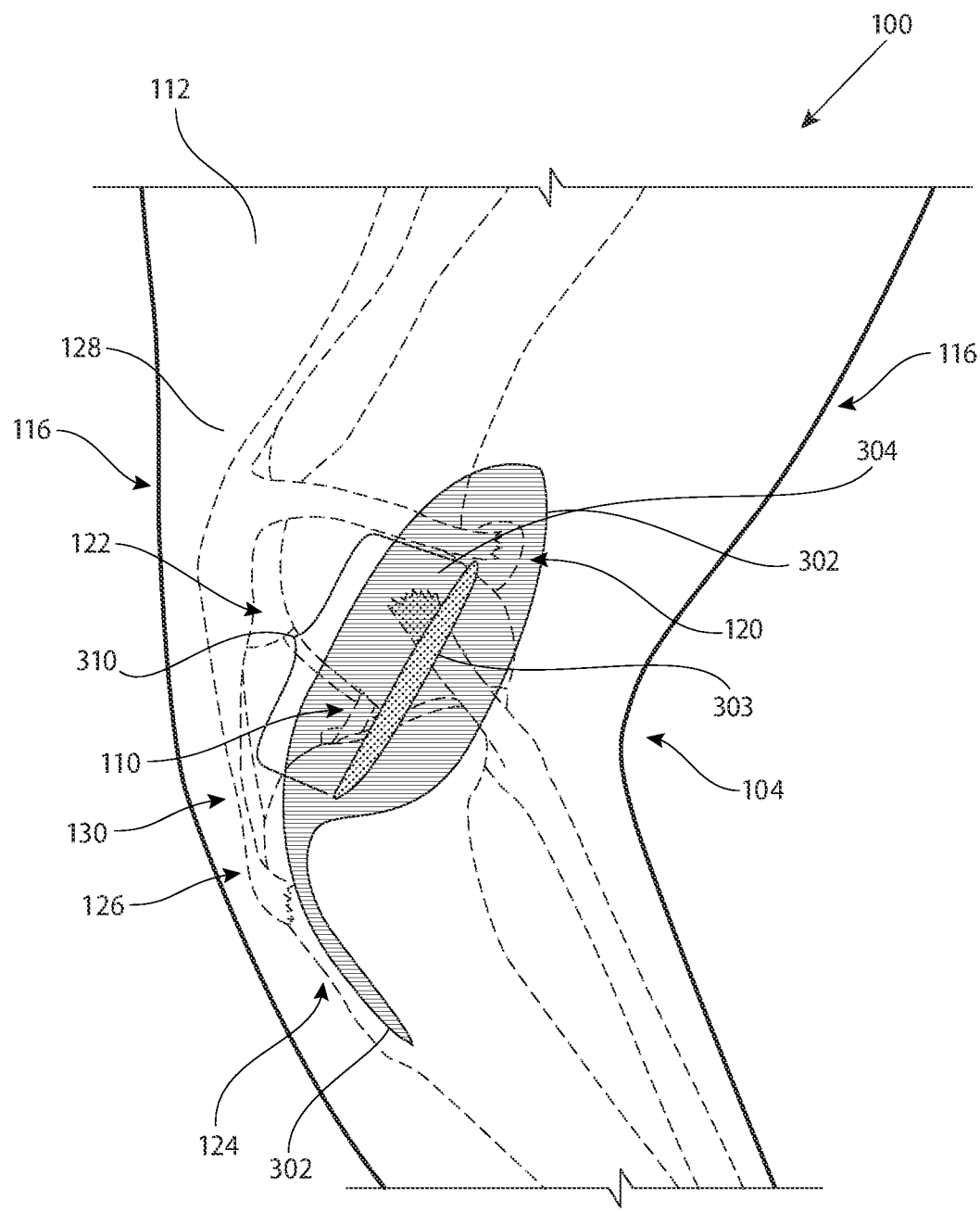
FIG. 2 illustrates a lateral view of the tendons and muscles of a left canine hind limb.
Figure 3:
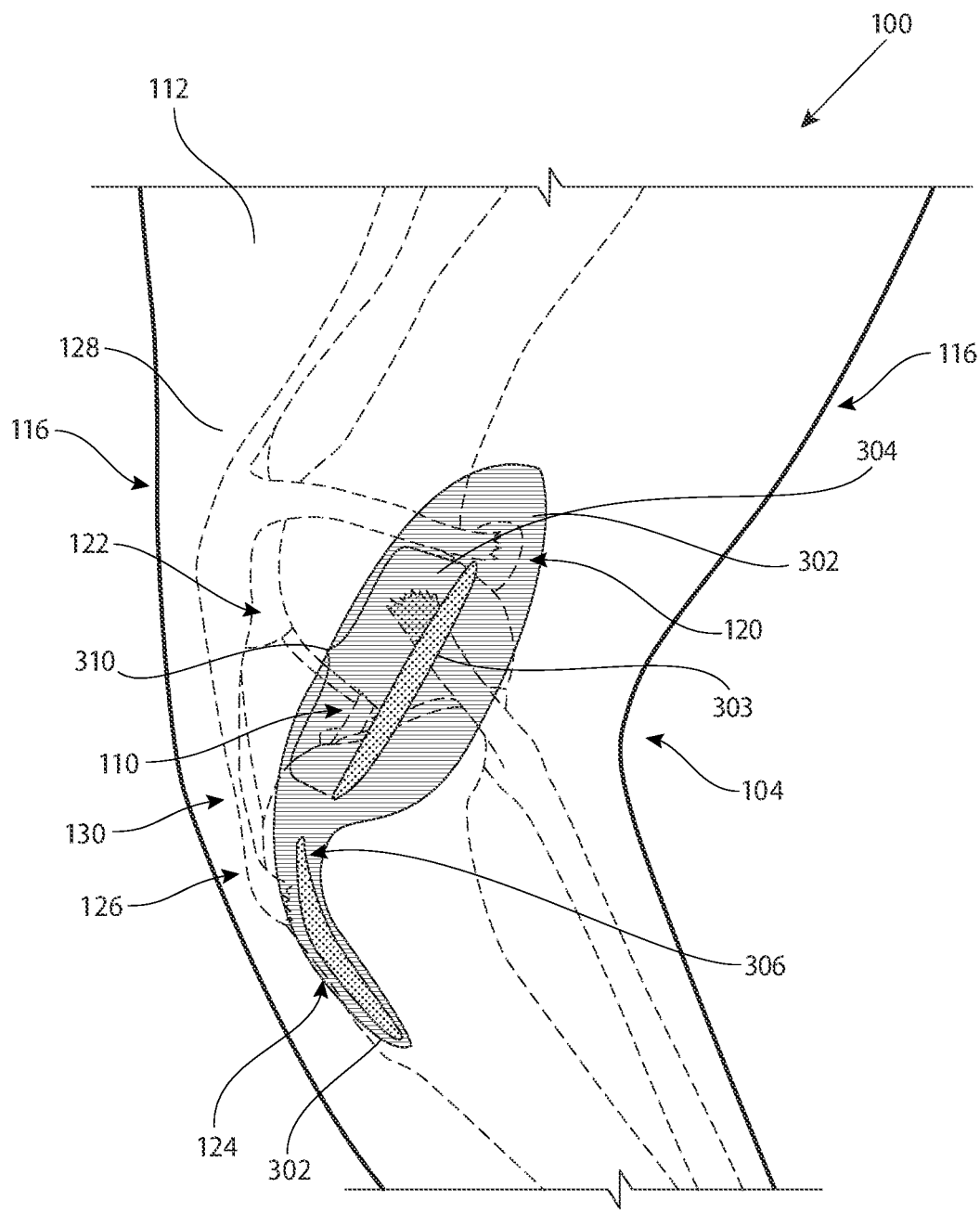
FIG. 3 illustrates a lateral view of the main ligaments and tendons of the canine stifle with a second incision proximal-lateral to the tibial tuberosity, and just lateral to the insertion of the patella tendon.

With reference to FIG. 1, FIG. 2, and FIG. 3, a skin incision 302 is made with a scalpel or other suitable instrument. The skin incision 302 is, advantageously, originating approximately one to two centimeters dorsal to the lateral fabella 120 and continuing distally to the proximal aspect 126 of the tibial tuberosity 124, then curving ventrally, distally, and parallel to the tibial tuberosity 124 for approximately two to three centimeters. The skin incision 302 is then widened or stretched, and may be clamped or otherwise held open, which as one of skill in the art will see, will permit access to tissues below the skin incision 302.

Thereafter, and with reference to FIG. 2 and FIG. 3, a fascia incision 303 may be made with a scalpel or other suitable instrument, and a surgical graft 304 may be prepared comprised of the lateral subcutaneous fat and fascia tissue in a region 310 near or adjacent to the skin incision 302 and the fascia incision 303, in which the subcutaneous fat and fascia lata incision in an area to be undermined for the surgical graft 304 comprise the region 310. The region 310 may be undermined, allowing the surgical graft 304 may be used towards the end of the surgical procedure 300, such that the surgical graft 304 may provide padding over the filament knots or attachments as created or used in the surgical procedure 300, by pulling the dissected or undermined surgical graft 304 back over the filament knots or attachments at an appropriate time in the surgical procedure 300, and securing the surgical graft 304 to fascia on the other side of the fascia incision 303, over the filament knots or attachments. In some aspects of the present disclosure, wherein the filament knots or attachments are located at a relatively more distal or lower position approximately at or near the tibial tuberosity, the surgical procedure 300 may omit the surgical graft 304 if the surgical graft 304 may not be needed to provide padding over the filament knots or attachments.

The skin 116 of the surgical limb 112 in the region of the skin incision 302 is separated from the lateral, cranial, and medial aspects of the tibial tuberosity 124 and patella ligament 130 (distal to the patella 122). With reference to FIG. 3, a small (approximately one to two centimeter) tibial-tuberosity-adjacent incision 306 is made on the proximal-lateral 132 aspect of the tibial tuberosity 124, just lateral to the insertion of the patella tendon 128 on the cranial aspect of the tibial tuberosity 124.

The muscle is bluntly dissected away from the proximal-lateral 132 aspect of the tibial tuberosity 124, exposing the bone, following the tibial-tuberosity-adjacent incision 306. With reference to FIG. 3, FIG. 5A, FIG. 5B, FIG. 5C, FIG. 19A, FIG. 19B, and FIG. 19C, to identify the location of a first hole 140 of two holes or more than two holes to be drilled in the tibial tuberosity 124, one skilled in the art can typically appreciate a dimple 134 (a small area of recessed bone) on the proximal-lateral 132 aspect of the tibial tuberosity 124 when applying a drill bit 160 to the area of the proximal-lateral 132 aspect. Once the dimple 134 is located, a surgeon drills in a drilling step 312, using the drill bit 160, the first hole 140 directly through the tibial tuberosity 124 (from a lateral aspect, also referred to as a lateral side 127, to a medial aspect, also referred to as a medial side 129 of the tibial tuberosity 124) at the location of the dimple 134, with reference to FIG. 5A, FIG. 5B, FIG. 5C, FIG. 19A, FIG. 19B, and FIG. 19C.

As illustrated in FIG. 5A, FIG. 5B, FIG. 5C, FIG. 19A, FIG. 19B, and FIG. 19C, the surgeon drills in a drilling step 314, using the drill bit 160 a second hole 142a of the same diameter as the first hole 140 through the tibial tuberosity 124 (again from a lateral aspect to a medial aspect of the tibial tuberosity 124) approximately near a vertical midpoint of the tibial tuberosity 124, or at a distance ranging from approximately one to four centimeters from the first hole 140, depending on the size and breed of the canine 100. It will be appreciated by one of skill in the art that one or more drill bits 160 may be used, and that the one or more drill bits 160 may be of different diameters, creating holes of different diameters. The second hole may be drilled in a relatively lower location, noted as a second hole 142b, which may be approximately two to three times the distance from the first hole 140 as the second hole 142a may be. The present disclosure of the first hole 140 and the second hole 142a or the second hole 142b is to present surgical methods for creating and maintaining isometric tension in the stifle joint 104 throughout the range of motion of the stifle joint 104. It will be appreciated by one of skill in the art that, in some aspects of the present disclosure, it may be advantageous to drill the first hole 140, the second hole 142a, and the second hole 142b, wherein the second hole 142a and the second hole 142b may be used for different of the one or more filaments 210 or of the plurality of filament portions 213, in threading the plurality of filament portions 213 the create the pathways of the present disclosure, to create and maintain isometric tension in the stifle joint 104 throughout the range of motion of the stifle joint 104.

The size of the first hole 140 and the second hole 142a and/or the second hole 142b, together comprising the "holes", drilled in the tibial tuberosity 124 is increased with the body size, weight, and muscle mass of the canine 100 who is the patient. The drill bit 160 may range in size from approximately three millimeters to approximately six millimeters in diameter. Increasing the diameter of the first hole 140 and the second hole 142a and/or the second hole 142b drilled allows for the holes to accommodate greater numbers and greater sizes of the one or more filaments 210 to be passed through, whether those one or more filaments 210 are advantageously monofilament nylon and/or comprise other materials.

Figure 4:
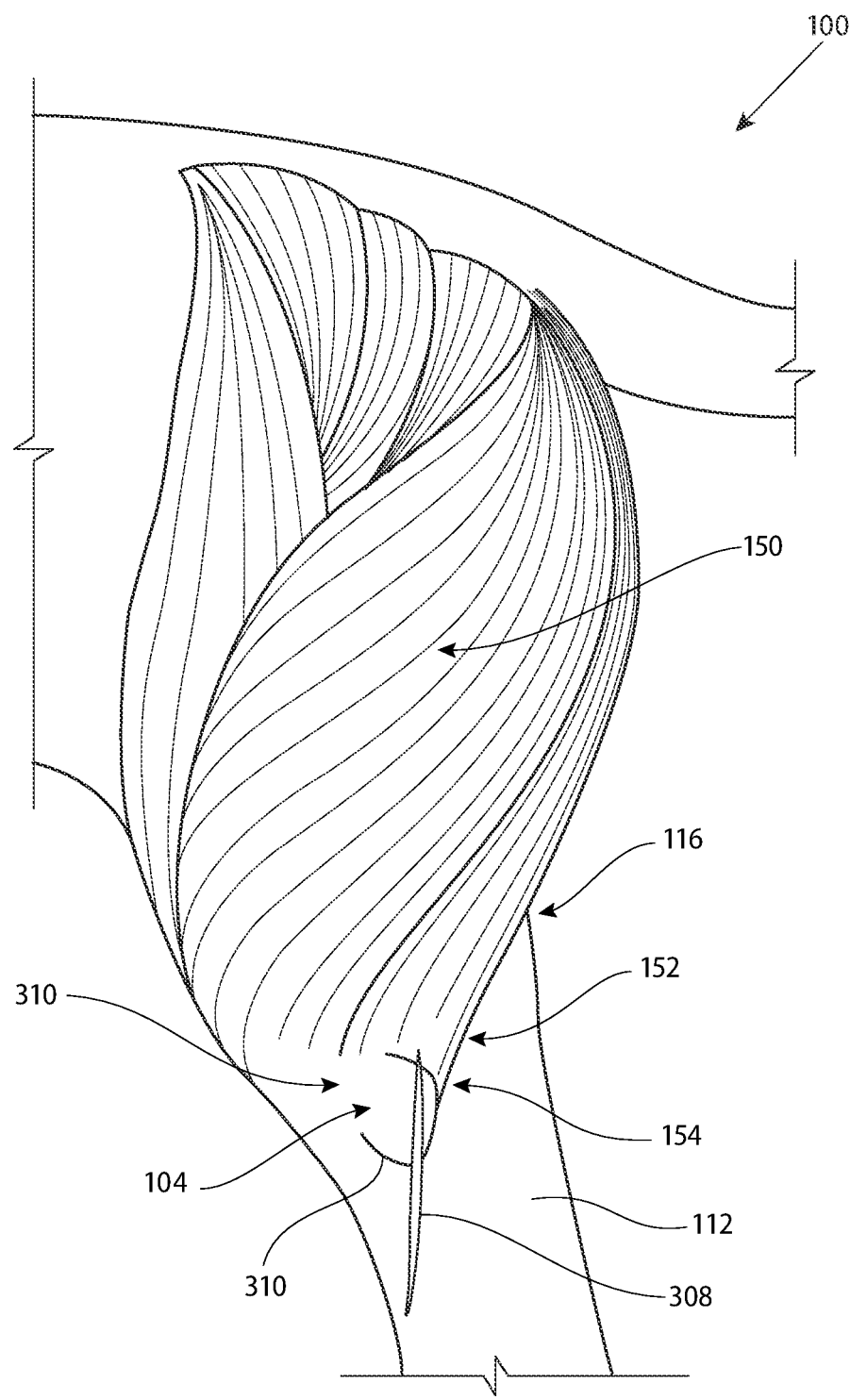
FIG. 4 illustrates a lateral view of the main ligaments and tendons of the canine stifle with a third incision made through the lateral aspect of the biceps femoris muscle.
Figure 5A:
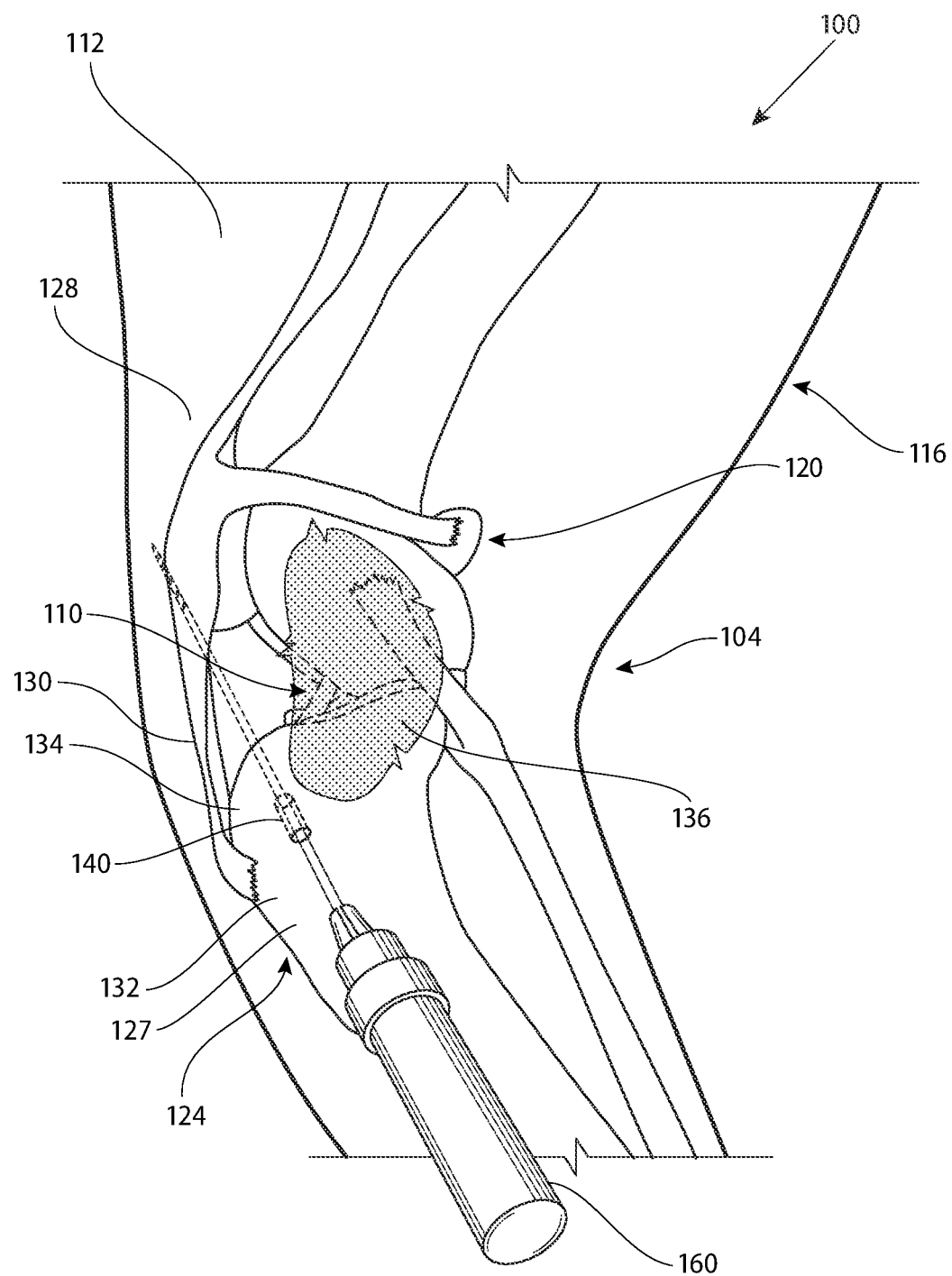
FIG. 5A illustrates a lateral view of the main ligaments and tendons of the canine stifle with a first hole being drilled through the tibial tuberosity.
Figure 5B:
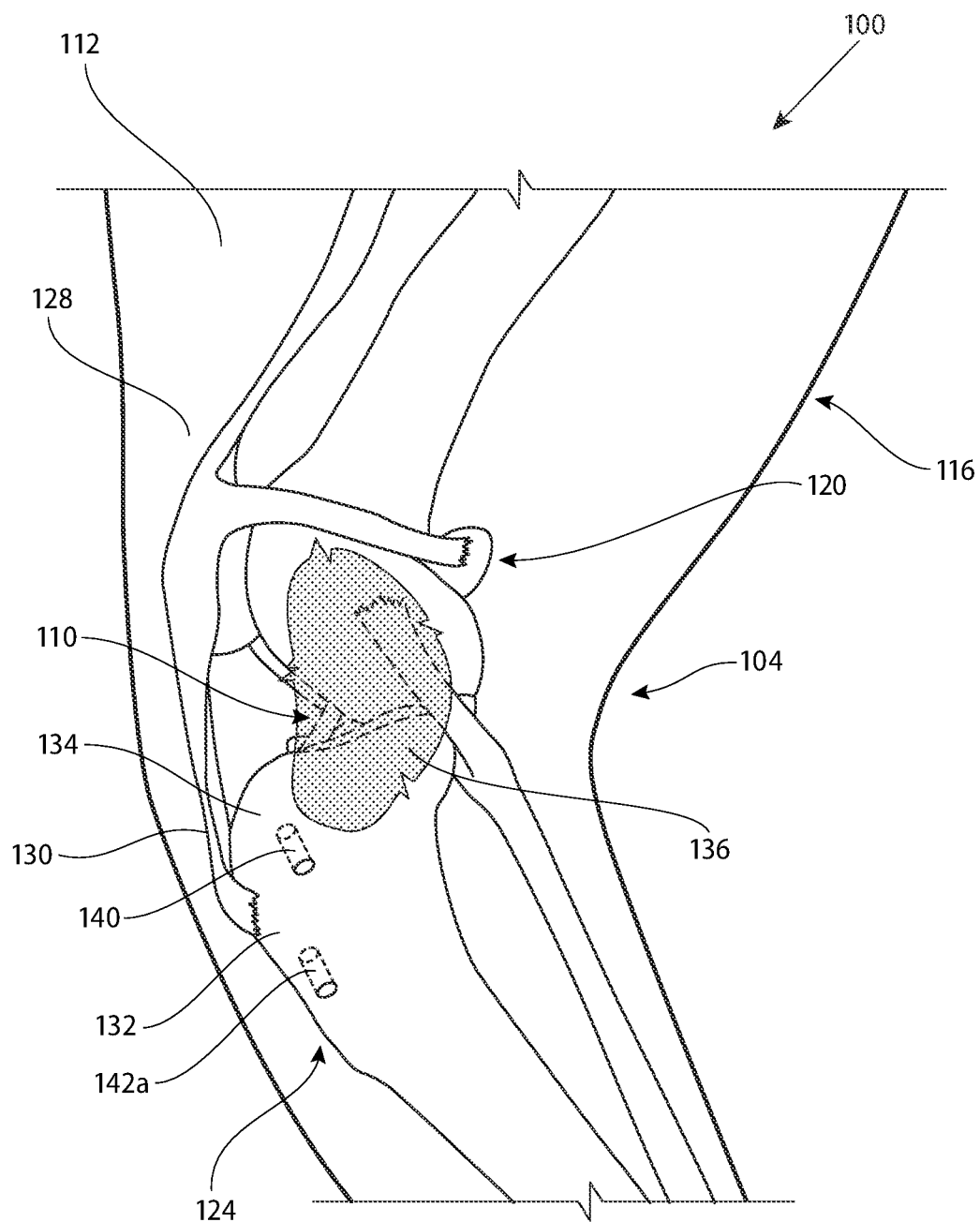
FIG. 5B illustrates a lateral view of the main ligaments and tendons of the canine stifle with a second hole being drilled through the tibial tuberosity in a first location.
Figure 5C:
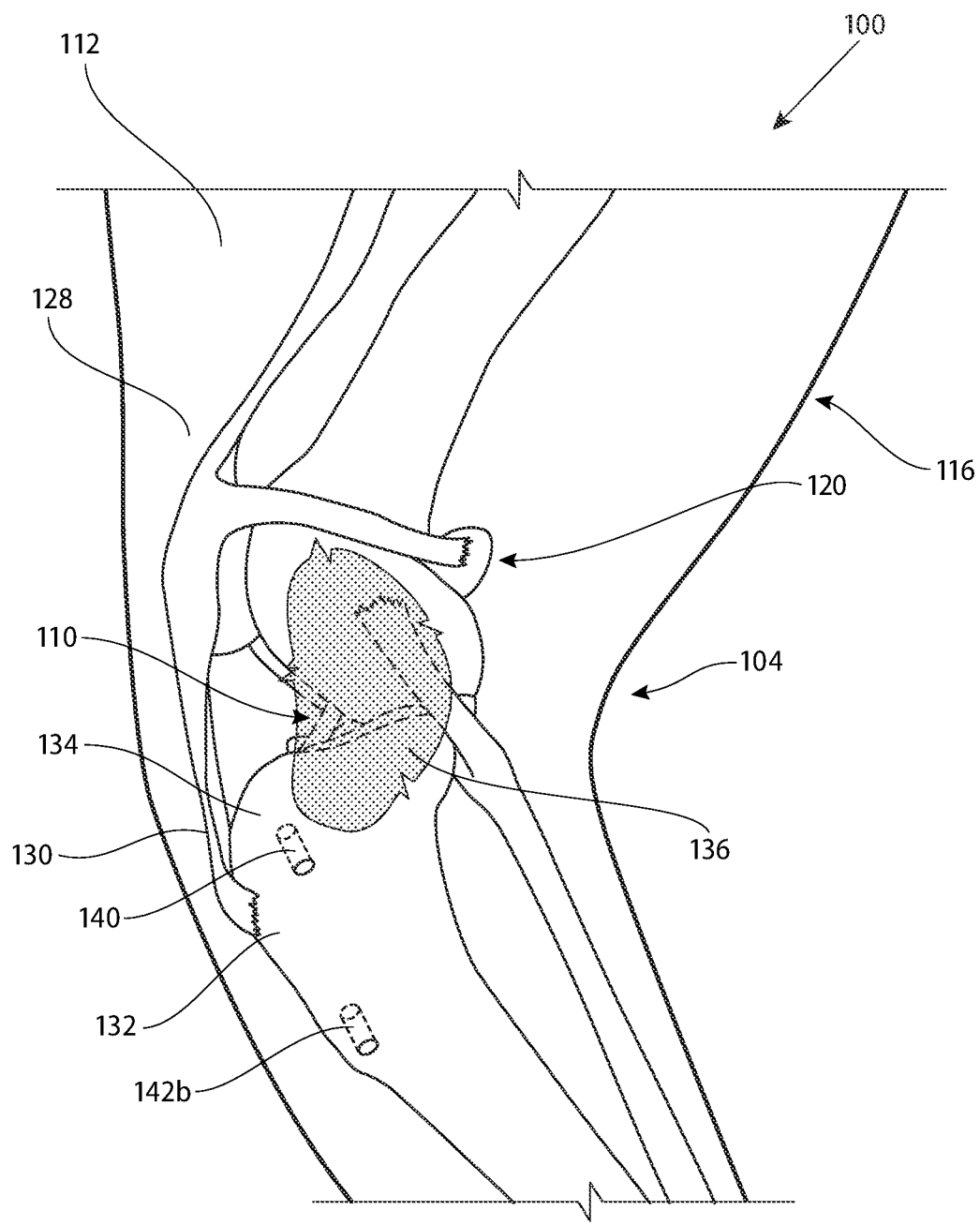
FIG. 5C illustrates a lateral view of the main ligaments and tendons of the canine stifle with a second hole being drilled through the tibial tuberosity in a second location.

As illustrated in FIG. 4, a lateral-fabella-adjacent incision 308, which may advantageously be relatively small, is made through a biceps femoris muscle 150 at a lateral aspect 152 of the biceps femoris muscle 150, at a distal-most point 154, passing the blade of a scalpel or other suitable instrument through the full thickness of the biceps femoris muscle 150 and tendon associated therewith, but taking care not to incise, the joint capsule below the biceps femoris muscle 150. The lateral-fabella-adjacent incision 308 is extended proximally, using curved Metzenbaum scissors or other suitable instruments, in the biceps femoris muscle 150 proximally, with the full length of the lateral-fabella-adjacent incision 308 ranging from approximately one to four centimeters, depending on the size and breed of the canine 100 until the lateral fabella 120 has been exposed and is readily accessible. The length of the lateral-fabella-adjacent incision 308 in the biceps femoral muscle will vary depending on the size of the canine 100, and range from approximately two to six centimeters in length. A length of approximately two centimeters may likely be sufficient for the lateral-fabella-adjacent incision 308 for a canine 100 weighing up to thirty pounds. For patients weighing over thirty pounds, the procedure adds roughly one to one and a half centimeters of lateral-fabella-adjacent incision 308 length per thirty pounds of body weight of the canine 100.

Figure 6:
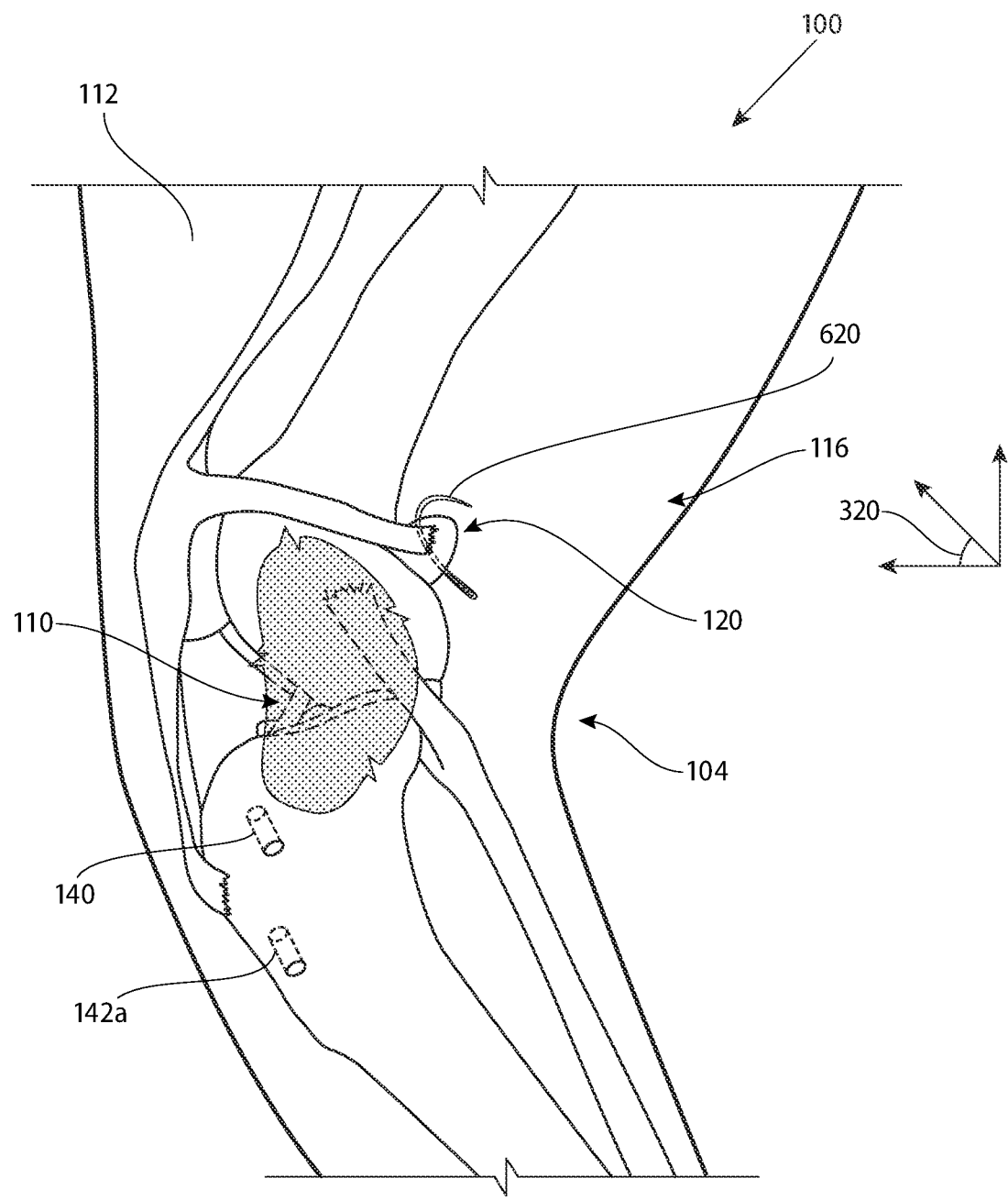
FIG. 6 illustrates a lateral view of a canine stifle with a curved needle circumnavigating around a lateral fabella.
Figure 7:
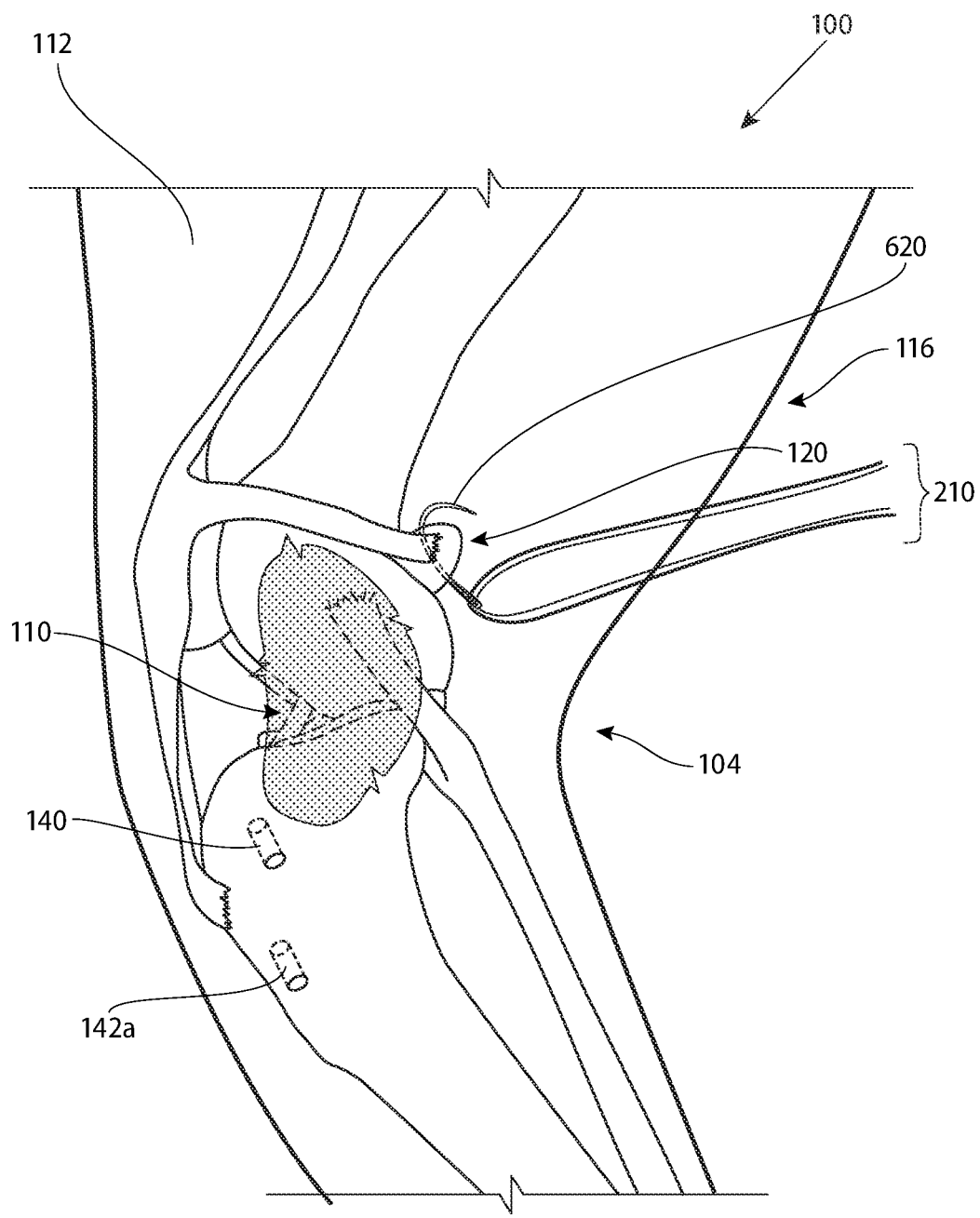
FIG. 7 illustrates a lateral view of a canine stifle with a curved needle circumnavigating around a lateral fabella, and one or more filaments threaded on to the curved needle.
Figure 28:
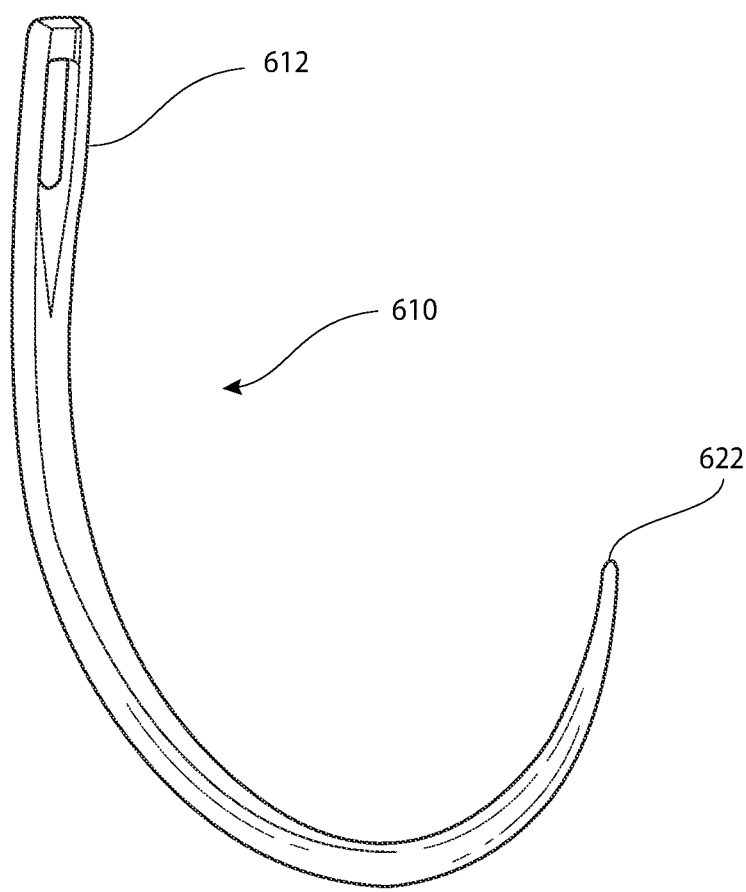
FIG. 28 illustrates an isometric view of a cruciate needle.
Figure 29:
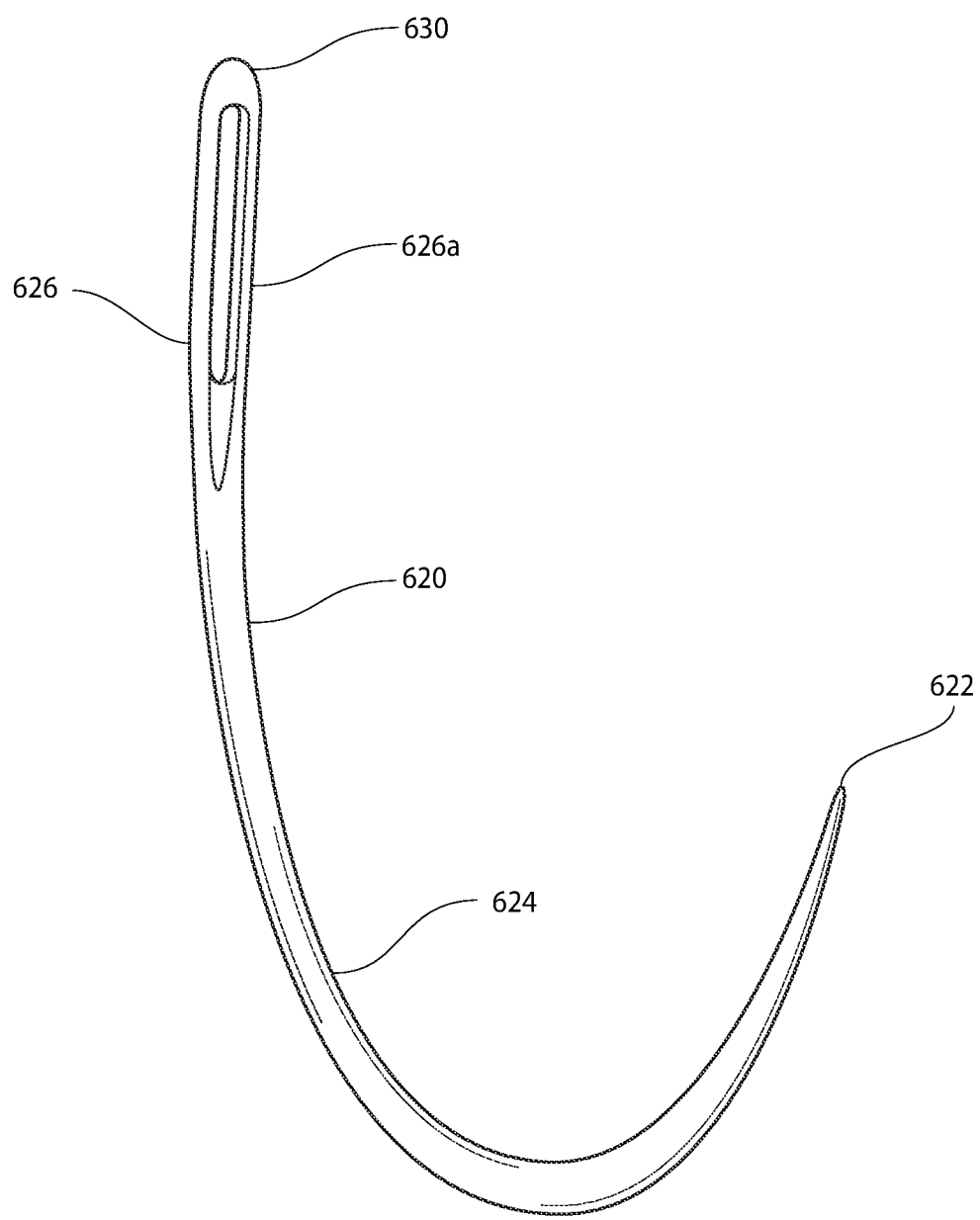
FIG. 29 illustrates an isometric view of a curved elongated eye stacking needle.
Figure 30:
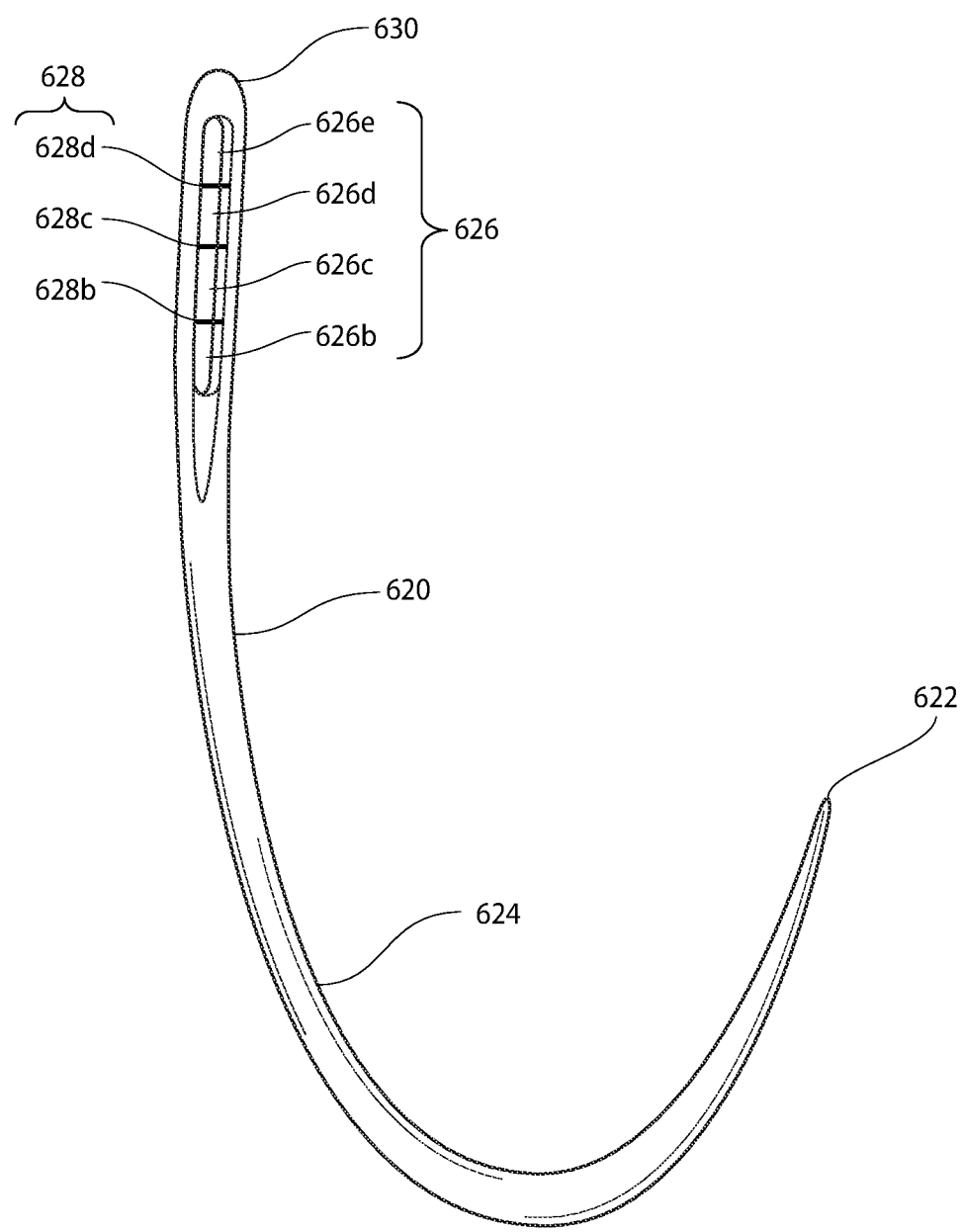
FIG. 30 illustrates an isometric view of a curved elongated eye stacking needle.
Figure 31:
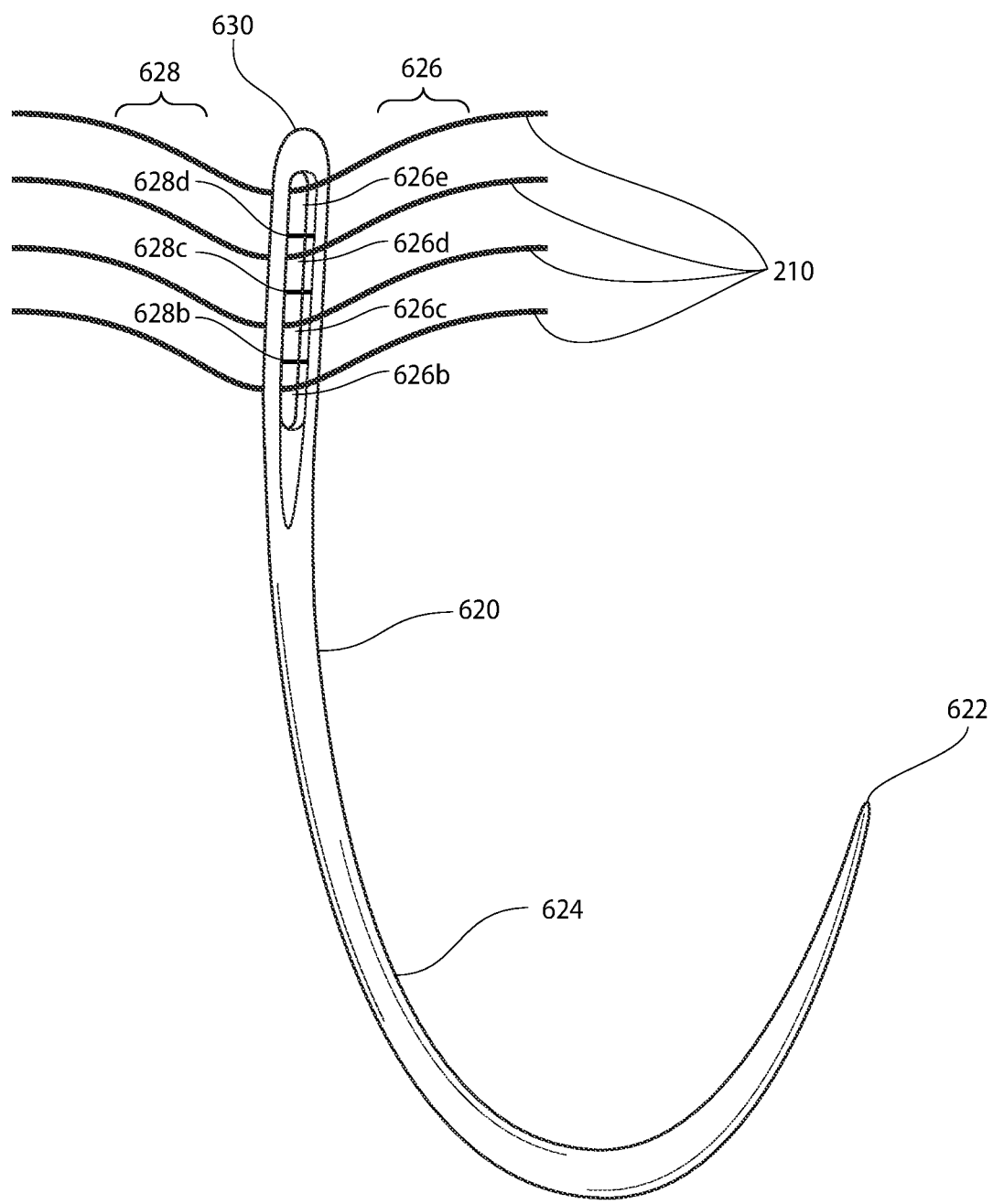
FIG. 31 illustrates an isometric view of a curved elongated eye stacking needle, with filaments threaded as described in the present disclosure.

As illustrated in FIG. 6, and with reference to FIG. 7, FIG. 8, FIG. 9, FIG. 10, and FIG. 27, once the lateral fabella 120 has been exposed and palpated, a curved elongated eye stacking needle 620 (a "CEES Needle", or "CEES", illustrated in FIG. 29, FIG. 30, and FIG. 31, in contrast to a standard cruciate needle 610 depicted in FIG. 28), is inserted in an inserting step 318 starting at the caudal-ventral aspect of the lateral fabella 120 and moved in a circumnavigation 322 proximally around the lateral fabella 120 at a needle-passage-angle 320 of approximately forty-five-degrees, exiting at the cranial-dorsal aspect of the lateral fabella 120. The curved elongated eye stacking needle 620, which may be referred to as a needle or as a surgical stacking needle, comprises a point 622, a curved body 624, one or more eyes 626, and an eye-end 630 being the end of the curved elongated eye stacking needle 620 distal to the point 622 and proximal to the one or more eyes 626. In some aspects, and with continued reference to FIG. 29, FIG. 30, and FIG. 31, the curved elongated eye stacking needle 620 with the one or more eyes 626 has a single eye, which may be referred to as an eye 626a. In such aspects the eye 626a is advantageously enlarged relative to an eye 612 of a standard cruciate needle 610, such that the eye 626a can fit the one or more filaments 210. In other aspects, the one or more eyes 626 comprises a plurality of eyes, referred to as a first eye 626b, a second eye 626c, a third eye 626d, a fourth eye 626e, and so on for the number of eyes deemed advantageous or desirable for the one or more eyes 626. The one or more eyes are referred to in sequence, with the first eye 626b being closest to the point 622, and the highest-numbered (e.g., third, fourth, etc.) eye being the eye closest to the eye-end 630. Each of the eyes in the one or more eyes 626, in aspects where the one or more eyes 626 comprises more than one such eye, is separated from any other of the one or more eyes 626 by an eye-support separator from one or more eye-support separators 628, being a portion of the needle that spans from one side of the needle to the other, defining the size and shape of the eyes adjacent to each of the one or more eye-support separators 628. In such aspects of the curved elongated eye stacking needle 620, comprising more than one such eye, the one or more eye-support separators 628 comprise one or more eye-support separators 628: a first eye-support separator 628b, a second eye-support separator 628c, a third eye-support separator 628d, and so on as appropriate for the number of eyes in the one or more eyes 626. The advantage of the one or more eyes 626 and the one or more eye-support separators 628 are increased strength of each eye and reduced breakage or damage to the curved elongated eye stacking needle 620, while having enough space in the one or more eyes 626 to hold and pull the one or more filaments 210. The curved elongated eye stacking needle 620, when used, hugs or holds tight to the lateral fabella 120 as the curved elongated eye stacking needle 620 is passed proximally. The needle-passage-angle 320 may advantageously be relatively more vertical for some breeds, including but not limited to in Pit bulls and Pit bull crosses.

With continued reference to FIG. 6, FIG. 7, FIG. 8, FIG. 9, FIG. 10, and FIG. 27, once the point 622 of the curved elongated eye stacking needle 620 has perforated the ligament of the lateral fabella 120, the point 622 is grasped and held (clamped) by a cruciate needle driver, being a suitable surgical instrument, and advantageously, large. The eye-end 630 of the curved elongated eye stacking needle 620 may be grasped and held (clamped) by a regular needle holder just below the one or more eyes 626 of the curved elongated eye stacking needle 620. The one or more eyes 626 of the curved elongated eye stacking needle 620 is then threaded 324 with varying combinations of the one or more filaments 210 (ranging in tensile strength 212 from 40-pound, 60-pound, and 80-pound, or higher or lower amounts of tensile strength 212, as are advantageous for the size and weight of the canine 100 who is the patient). The one or more filaments 210 may, advantageously, be sterile forty-eight-inch-long monofilament nylon, or may be other lengths and/or other materials. The one or more eyes 626—meaning, depending on the aspect of the needle used, either an eye 626a or a first eye 626b, a second eye 626c, and so on—are threaded 324 by stacking the one or more filaments 210 vertically within the one or more eyes 626 of the curved elongated eye stacking needle 620, with one filament of the one or more filaments 210 on top of the other filament of the one or more filaments 210. As each filament of the one or more filaments 210 is threaded 324 through the one or more eyes 626 of the curved elongated eye stacking needle 620, it has been found advantageous to have a midpoint 211 of each filament of the one or more filaments 210 balanced on either side of the one or more eyes 626, such that a symmetrical and equal length (approximately twenty-four inches if the filament of the one or more filaments 210 is approximately forty-eight inches) of the filament of the one or more filaments 210 is on each side of the curved elongated eye stacking needle 620. Thereafter, for each filament of the one or more filaments 210 of the one or more filaments 210, comprising two ends that are opposite each other, referred to for each filament of the one or more filaments 210 as a first filament-end 230 and a second filament-end 232. The first filament-end 230 and the second filament-end 232 of each filament of the one or more filaments 210 are then clasped together in a clasping-step 330 and retained in a retaining-step 332 using a kelly forceps, or other suitable medical forceps or locking forceps, referred to in the present disclosure as a kelly forceps. After the first filament-end 230 and the second filament-end 232 are retained in the retaining-step 332 to each other, the retained ends of each of the one or more filaments 210 are referred to as a first clamped ends 234.

A canine 100 that weighs about seventy-five-pounds will, typically, have two 60-pound (60 #) filaments of the one or more filaments 210 (which, after they are cut or divided, become four filament portions of the plurality of filament portions 213) and two 40-pound (40 #) filaments of the one or more filaments 210 (which, after they are cut or divided, become four filament portions of the plurality of filament portions 213).

With reference to FIG. 6, FIG. 7, FIG. 8, FIG. 9, and FIG. 10, and with reference to FIG. 27, the threaded 324 curved elongated eye stacking needle 620 is clasped with the cruciate needle driver or other suitable instrument and the threaded 324 curved elongated eye stacking needle 620 is moved in a circumnavigation 322 directly around the lateral fabella 120, "hugging" the curved elongated eye stacking needle 620 close to the lateral fabella 120 as the curved elongated eye stacking needle 620 passes around the lateral fabella 120 at an angle approximately forty-five degrees to the horizontal plane. This approximately 45-degree angle path of the curved elongated eye stacking needle 620 may have to be increased to approximately 65 degrees in pit bulls and pit bull crosses.

The point 622 of the curved elongated eye stacking needle 620 is grasped in a grasping-step 326 with the cruciate needle driver or other suitable instrument, with continued reference to FIG. 6, FIG. 7, FIG. 8, FIG. 9, FIG. 10, and FIG. 27, as the point 622 exits on the other side of the lateral fabella 120 and the curved elongated eye stacking needle 620 is pulled in a pulling-step 328 completely around the lateral fabella 120 in a tight orbit, as the person carrying out the surgical procedure 300 grasps the curved elongated eye stacking needle 620 in the grasping-step 326 and turns the curved elongated eye stacking needle 620 incrementally as the curved elongated eye stacking needle 620 is pulled in the pulling-step 328 (using an appropriate turning wrist action) in a full orbit around the lateral fabella 120 until the threaded 324 curved elongated eye stacking needle 620 and one or more filaments 210 can be pulled in a pulling-step 328 free in a lateral direction from the stifle joint 104. This final lateral pull may sometimes require the assistance of another surgeon or surgical technician.

With continued reference to FIG. 6, FIG. 7, FIG. 8, FIG. 9, FIG. 10, and FIG. 27, once the curved elongated eye stacking needle 620 is pulled free around the lateral fabella 120, each of the one or more filaments 210 stacked within the one or more eyes 626 of the curved elongated eye stacking needle 620 is cut in a cutting-step 334 at its apex, each apex being the point of each of the one or more filaments 210 which is contacting the one or more eyes 626 of the curved elongated eye stacking needle 620, and advantageously, such point is the midpoint 211 of each of the filaments of the one or more filaments 210, with scissors and freed from the one or more eyes 626. When each filament of the one or more filaments 210 is cut in the cutting-step 334, the act of cutting creates two new ends from each of the filaments of the one or more filaments 210 passed around the lateral fabella 120, a third filament-end 240 and a fourth filament-end 242, and the act of cutting in the cutting-step 334 makes each of the one or more filaments 210 into a plurality of filament portions 213. The plurality of filament portions 213 may be referred to as a first filament portion 213a and a second filament portion 213b, which are paired and created from the same one of the one or more filaments 210, e.g. a first filament 210a, and other filament portions from the plurality of filament portions 213 may be referred to as a third filament portion 213c and a fourth filament portion 213d which are paired and created from a different one of the one or more filaments 210, e.g. a second filament 210b. In some aspect of the present disclosure, a fifth filament portion and a sixth filament portion which are paired may be created from a third filament, and a seventh filament portion and eighth filament portion which are paired may be created from a fourth filament, and so on for the number of the one or more filaments 210 used. For a given one of the one or more filaments 210, the third filament-end 240 and the fourth filament-end 242 may be ends of the first filament portion 213a and the second filament portion 213b, or other filament portions from the others of the one or more filaments 210. All of the plurality of filament portions 213 together, after being created by the one or more filaments 210 (e.g., the first filament 210a, the second filament 210b, and the third filament and fourth filament if they are implemented, which as will be apparent to one of skill in the art, should be determined based on what the surgeon deems appropriate based on that patient's body weight and muscle mass) being cut, are together referred to as the plurality of filament portions 213. The third filament-end 240 and the fourth filament-end 242 are then clasped together in a clasping-step 340 and retained in a retaining-step 342 using a kelly forceps, or other suitable medical forceps or locking forceps. After the third filament-end 240 and the fourth filament-end 242 are retained in the retaining-step 342 to each other, these retained ends of each of the one or more filaments 210 are referred to as a second clamped ends 244 of that particular one of the one or more filaments 210. Each of the second clamped ends 244 are thereafter lined up on the surgical drape, i.e., the surgical field.

With reference to FIG. 11, FIG. 12, FIG. 13, FIG. 14, FIG. 15A, FIG. 15B, FIG. 16, FIG. 17, FIG. 18A, FIG. 18B, FIG. 18C, FIG. 18D, FIG. 18E, FIG. 18F, FIG. 18G, FIG. 18H, FIG. 20A, FIG. 20B, FIG. 21, FIG. 22, FIG. 23, FIG. 24, FIG. 25, FIG. 26, and FIG. 27, for each of the one or more filaments 210, there exists the first clamped ends 234 and the second clamped ends 244. Each first clamped ends 234 of one of the one or more filaments 210 is paired up, in a pairing-step 350, with the second clamped ends 244 of that one of the one or more filaments 210, by pulling on either a second clamped ends 244 or a first clamped ends 234, and seeing which of the other ones of the first clamped ends 234 or second clamped ends 244 moves. Once all of the corresponding pairs of first clamped ends 234 and second clamped ends 244 have been paired up in the pairing-step 350, each of the one or more filaments 210, which are now effectively doubled as the plurality of filament portions 213, is pulled taught in a tautening-step 352.

The surgical procedure 300 strategically implants one or more filaments 210 along the one or more extra-capsular loading pathways 214, which may comprise two separate such pathways, that divide and distribute the load 106 on the stifle joint 104 of the patient in different planes and directions, with reference to FIG. 1, FIG. 2, FIG. 3, FIG. 4, FIG. 11, FIG. 12, FIG. 13, FIG. 14, FIG. 15A, FIG. 15B, FIG. 16, FIG. 17, FIG. 18A, FIG. 18B, FIG. 18C, FIG. 18D, FIG. 18E, FIG. 18F, FIG. 18G, FIG. 18H, FIG. 20A, FIG. 20B, FIG. 21, FIG. 22, FIG. 23, FIG. 24, FIG. 25, and FIG. 26. One portion of the load 106 is distributed more distally along a caudolateral pathway 360 that carries its share of the load 106 exclusively on the lateral aspect of the stifle joint 104 and along the vertical planes 216. The remaining portion of the load 106 is distributed more proximally along a craniomedial pathway 370 that carries its share of the load 106 more proximally and along the horizontal planes 218 (medial to lateral) and vertical planes 216.

The separate loading pathways—the caudolateral pathway 360 and the craniomedial pathway 370—are created in the following manner, with reference to FIG. 11, FIG. 12, FIG. 13, FIG. 14, FIG. 15A, FIG. 15B, FIG. 16, FIG. 17, FIG. 18A, FIG. 18B, FIG. 18C, FIG. 18D, FIG. 18E, FIG. 18F, FIG. 18G, FIG. 18H, FIG. 20A, FIG. 20B, FIG. 21, FIG. 22, FIG. 23, FIG. 24, FIG. 25, and FIG. 26. Half of the total, or other suitable number or portion, of the first clamped ends 234 of the one or more filaments 210 are threaded through the eye of, in a threading-step 372, also referred to as "threaded on", a straight elongated eye stacking needle 650, which is advantageously approximately four inches long. The straight elongated eye stacking needle 650 is then passed through the first hole 140, which is the proximal-most hole in the tibial tuberosity 124 from lateral to medial, in a first passing-step 374. The straight elongated eye stacking needle 650 is then passed, in a second passing-step 376, back through the second hole 142a and/or the second hole 142b, which is the distal-most hole in the tibial tuberosity 124 from medial to lateral. Each of the first clamped ends 234 used in the preceding steps are then paired with the second clamped ends 244 used in the preceding steps and corresponding to the first clamped ends 234 on each of the one or more filaments 210, clasping them together in a third clasping step 378, using Kelly hemostats or other suitable instruments.

In some aspects of the present disclosure, and with continued reference to FIG. 11, FIG. 12, FIG. 13, FIG. 14, FIG. 15A, FIG. 15B, FIG. 16, FIG. 17, FIG. 18A, FIG. 18B, FIG. 18C, FIG. 18D, FIG. 18E, FIG. 18F, FIG. 18G, FIG. 18H, FIG. 20A, FIG. 20B, FIG. 21, FIG. 22, FIG. 23, FIG. 24, FIG. 25, and FIG. 26, the other half or other suitable number or portion of the total of the first clamped ends 234 of the one or more filaments 210 are threaded through the eye of, in a threading-step 380, a straight elongated eye stacking needle 650, which is advantageously approximately four inches long, and which may be referred to as a surgical stacking needle. This may be the straight elongated eye stacking needle 650 that was previously used, or another straight elongated eye stacking needle 650. The straight elongated eye stacking needle 650 is then passed through the first hole 140, which is the proximal-most hole in the tibial tuberosity 124 from lateral to medial, in a third passing-step 382. The needle is then carried, in a first carrying-step 384, proximally at an angle of approximately thirty to approximately forty-five degrees) first through the soft fascia tissue on the medial aspect of the patella ligament 130, exiting and crossing over the cranial border behind the patella ligament 130, and between the patella ligament 130 and the joint capsule, and then the needle is carried more proximally, in a second carrying-step 386, through the fascia tissue 136 on the lateral aspect of the patella ligament 130 and may be carried, in a third carrying-step 388, through the lateral fascia (fascia lata) of the biceps femoris muscle tendon unit (being careful not to perforate the joint capsule). Each of the first clamped ends 234 used in the preceding steps are then paired with the second clamped ends 244 used in the preceding steps and corresponding to the first clamped ends 234 on each of the one or more filaments 210, clasping them together in a fourth clasping step 389, using Kelly hemostats or other suitable instruments.

Figure 32:
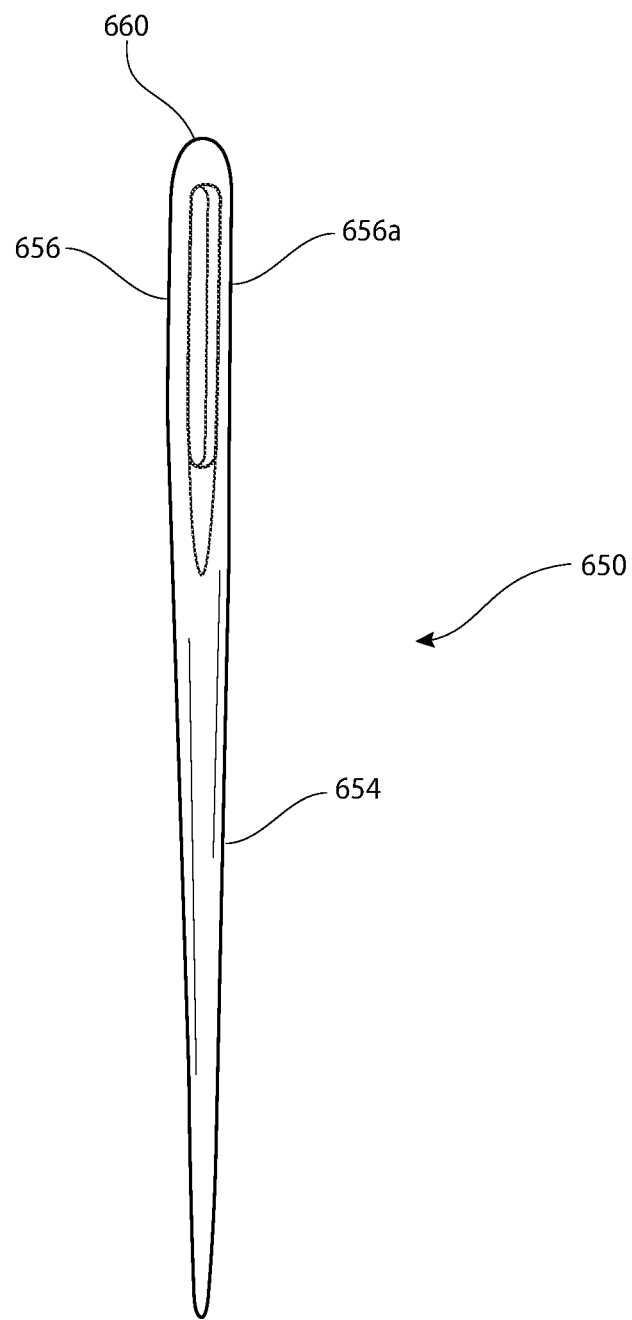
FIG. 32 illustrates an isometric view of a straight elongated eye stacking needle.
Figure 33:
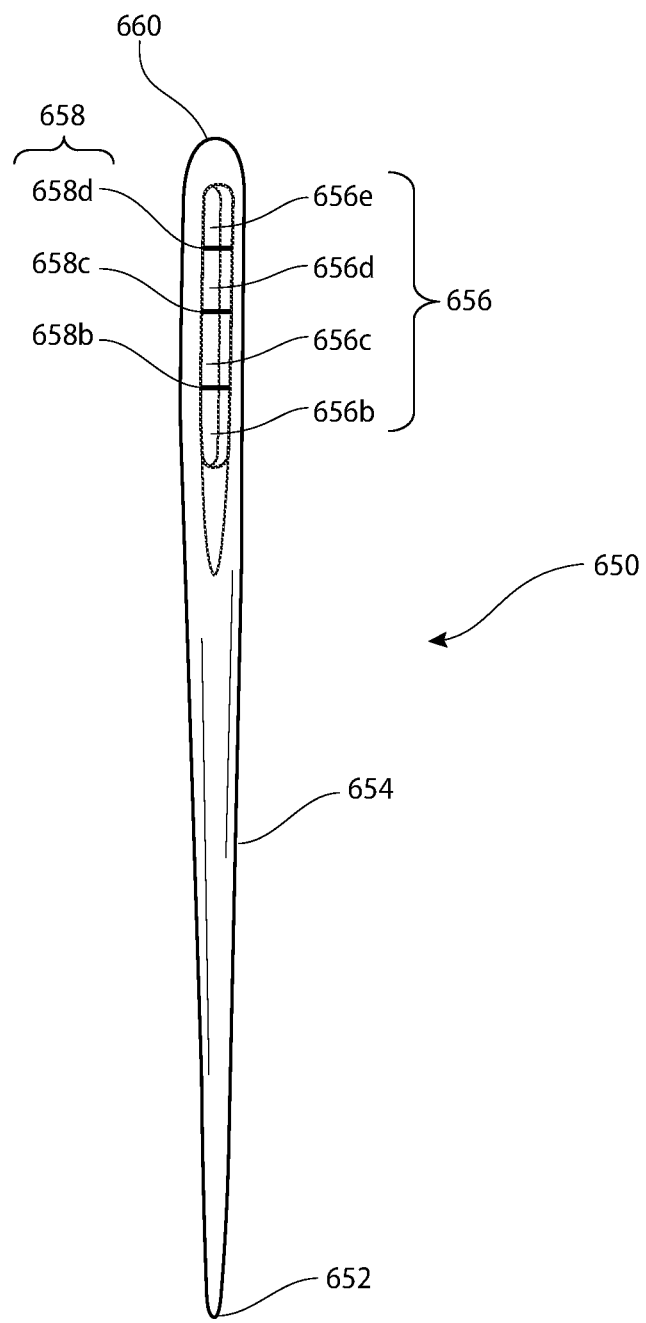
FIG. 33 illustrates an isometric view of a straight elongated eye stacking needle, with filaments threaded as described in the present disclosure.
Figure 34:
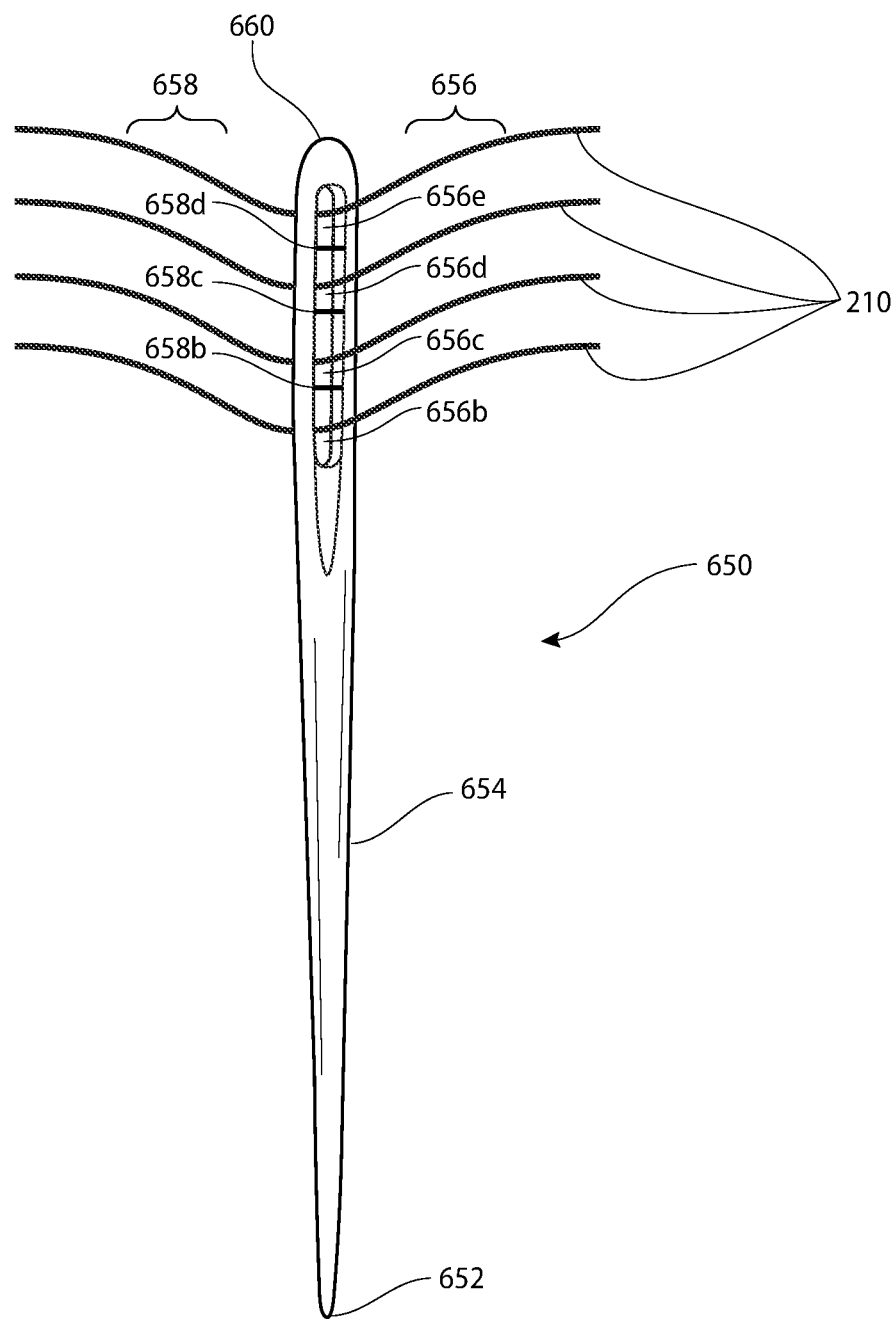
FIG. 34 illustrates an isometric view of a straight elongated eye stacking needle, with filaments threaded as described in the present disclosure.

The straight elongated eye stacking needle 650, which may be referred to as a needle, and with reference to FIG. 32, FIG. 33, and FIG. 34, comprises a point 652, a body 654, one or more eyes 656, and an eye-end 660 being the end of the straight elongated eye stacking needle 650 distal to the point 652 and proximal to the one or more eyes 656. The straight elongated eye stacking needle 650 may be substantially straight or approximately straight. In some aspects, as shown in FIG. 32, the straight elongated eye stacking needle 650 with the one or more eyes 656 has a single eye, which may be referred to as an eye 656a. In such aspects the eye 656a is advantageously enlarged relative to an eye 612 of a standard cruciate needle 610, such that the eye 656a can fit the one or more filaments 210. In other aspects, as shown in FIG. 33 and FIG. 34, the one or more eyes 656 comprises multiple eyes, referred to as a first eye 656b, a second eye 656c, a third eye 656d, a fourth eye 656e, and so on for the number of eyes deemed advantageous or desirable for the one or more eyes 656. The one or more eyes are referred to in sequence, with the first eye 656b being closest to the point 652, and the highest-numbered (e.g., third, fourth, etc.) eye being the eye closest to the eye-end 660. Each of the eyes in the one or more eyes 656, in aspects where the one or more eyes 656 comprises more than one such eye, is separated from any other of the one or more eyes 656 by an eye-support separator of one or more eye-support separators 658, being a portion of the needle that spans from one side of the needle to the other, defining the size and shape of the eyes adjacent to each of the one or more eye-support separators 658. In such aspects of the straight elongated eye stacking needle 650, comprising more than one such eye, the one or more eye-support separators 658 comprise one or more eye-support separators 658: a first eye-support separator 658b, a second eye-support separator 658c, a third eye-support separator 658d, and so on as appropriate for the number of eyes in the one or more eyes 656. The advantage of the one or more eyes 656 and the one or more eye-support separators 658 are increased strength of each eye and reduced breakage or damage to the straight elongated eye stacking needle 650, while having enough space in the one or more eyes 656 to hold and pull the one or more filaments 210.

Figure 8:
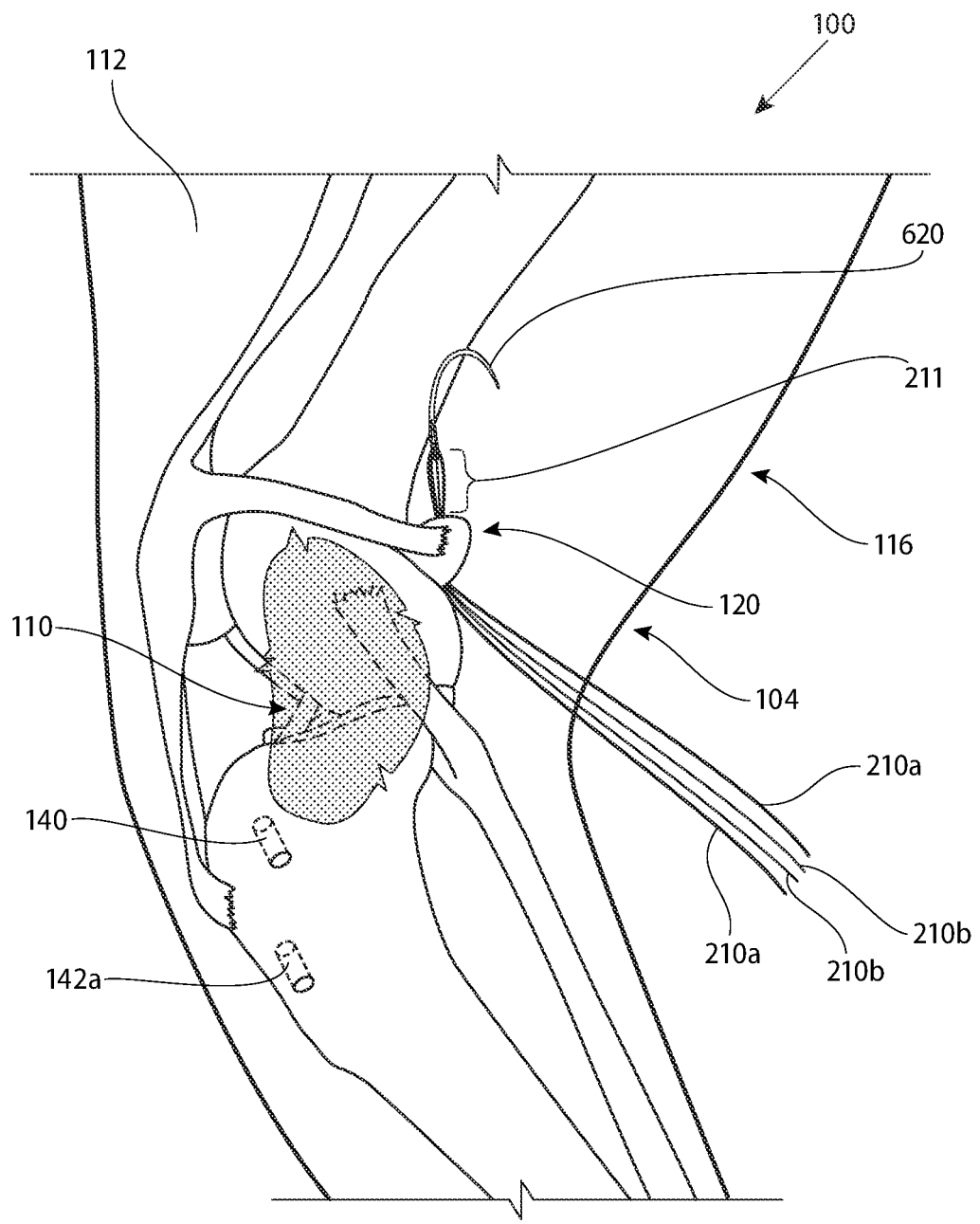
FIG. 8 illustrates a lateral view of a canine stifle with a curved needle circumnavigated around a lateral fabella, and one or more filaments threaded on to the curved needle.
Figure 9:
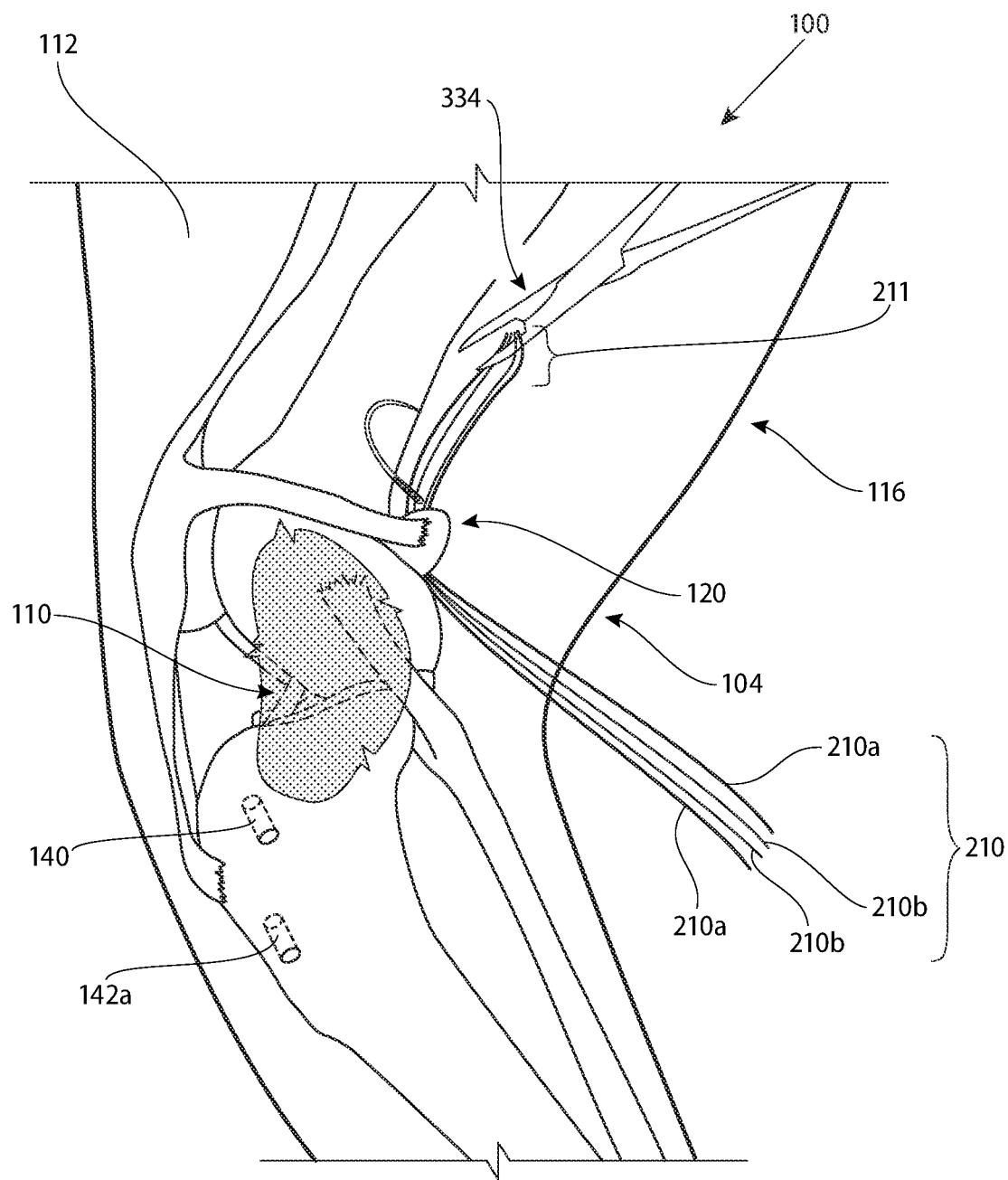
FIG. 9 illustrates a lateral view of a canine stifle with the curved needle circumnavigated around a lateral fabella, and the one or more filaments being severed.
Figure 10:
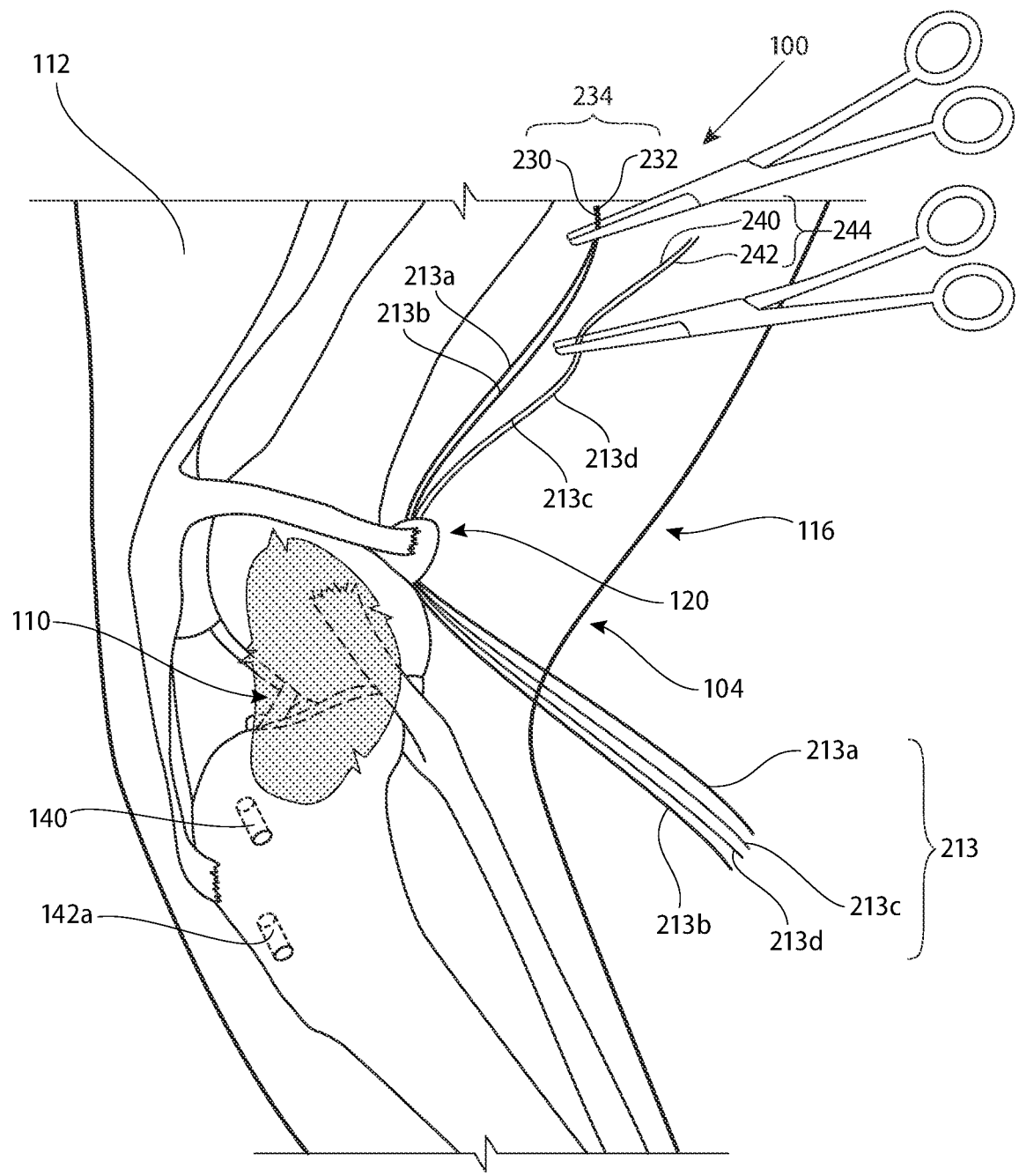
FIG. 10 illustrates a lateral view of a canine stifle with the curved needle removed, and the one or more filaments severed to become a plurality of filament portions.
Figure 11:
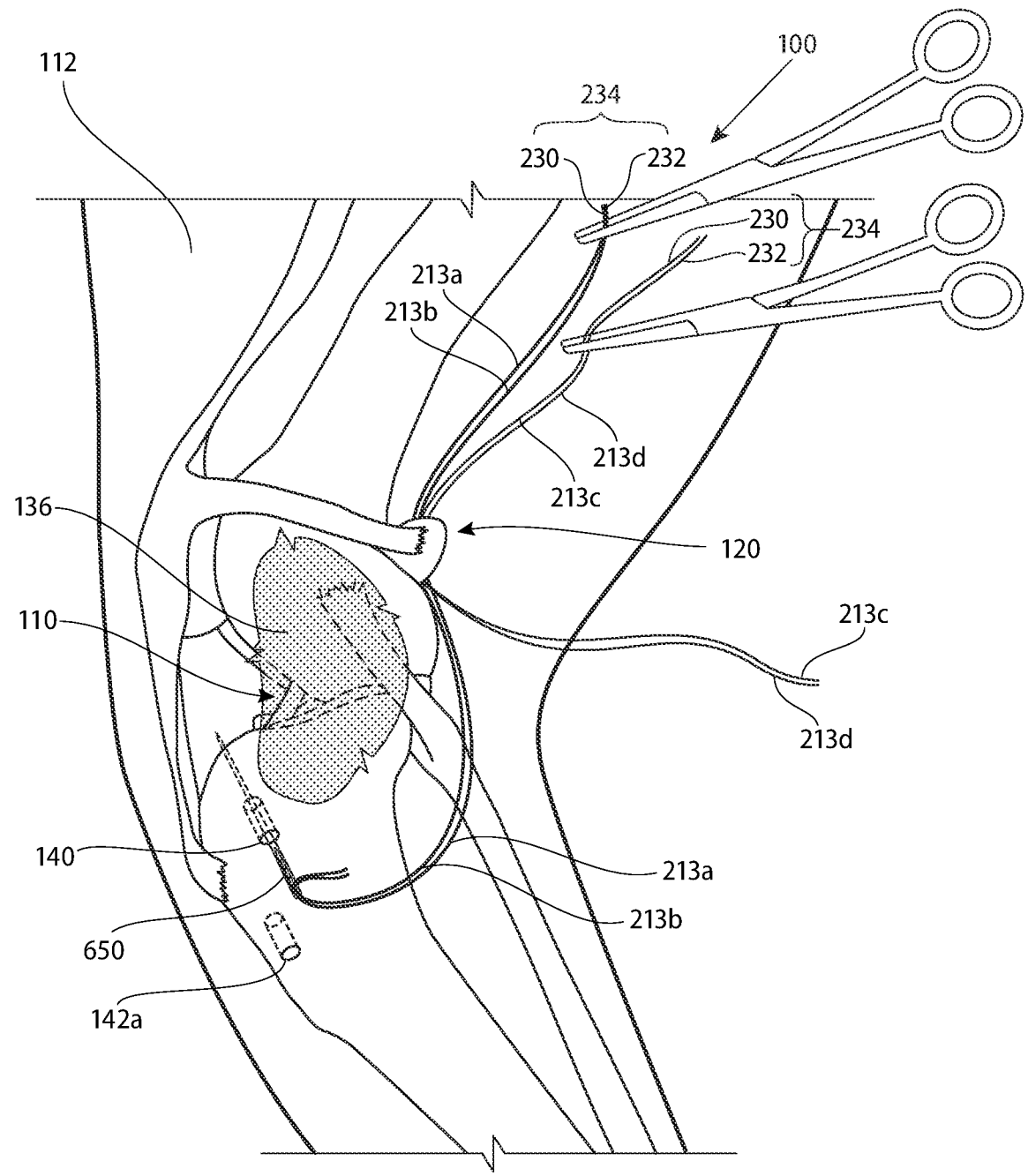
FIG. 11 illustrates a lateral view of a canine stifle with a first and a second filament portion of the plurality of filament portions threaded onto a straight needle and into a first hole.
Figure 12:
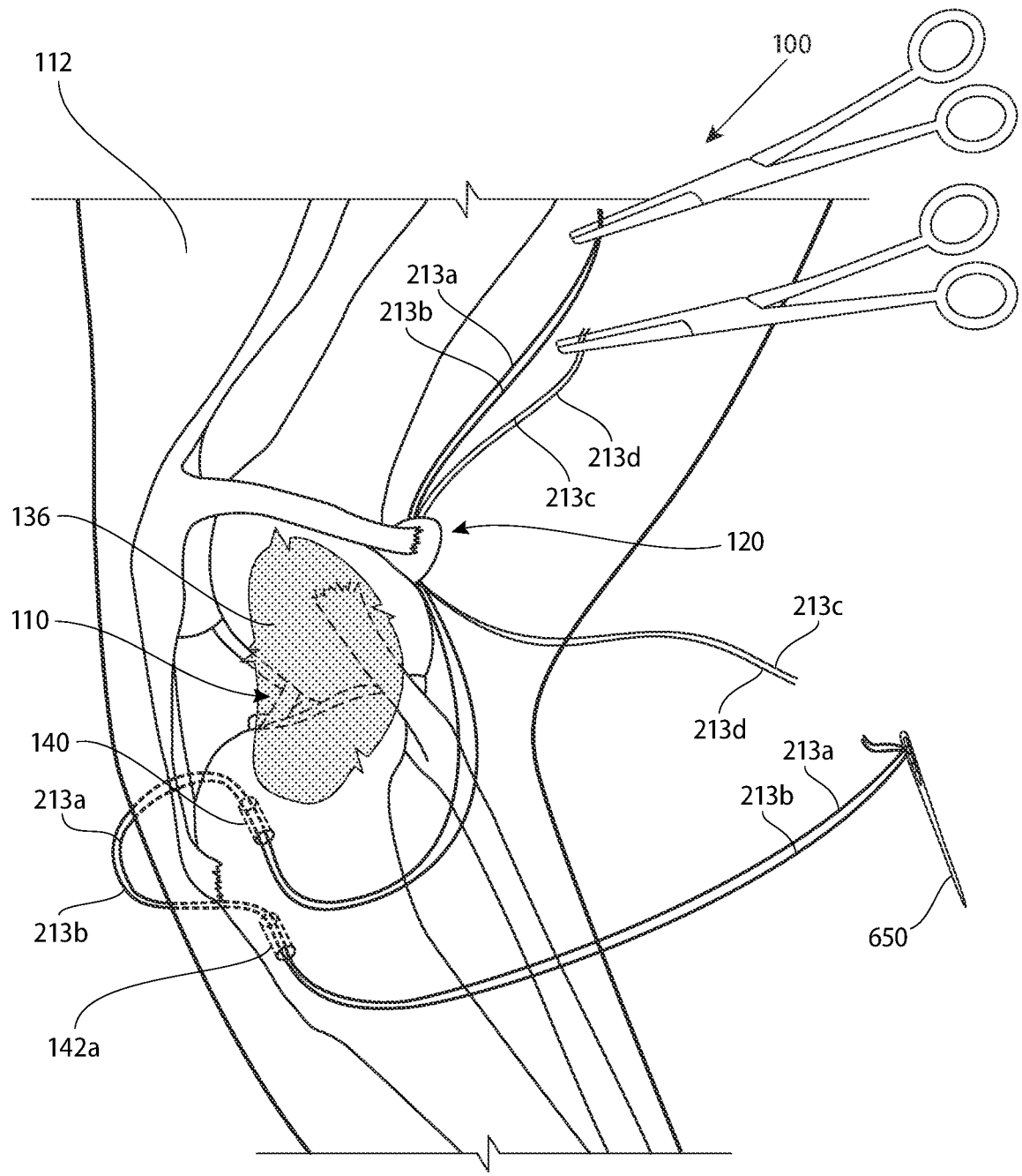
FIG. 12 illustrates a lateral view of a canine stifle with the first and second filament portions of the plurality of filament portions threaded onto a straight needle and through a second hole.
Figure 13:
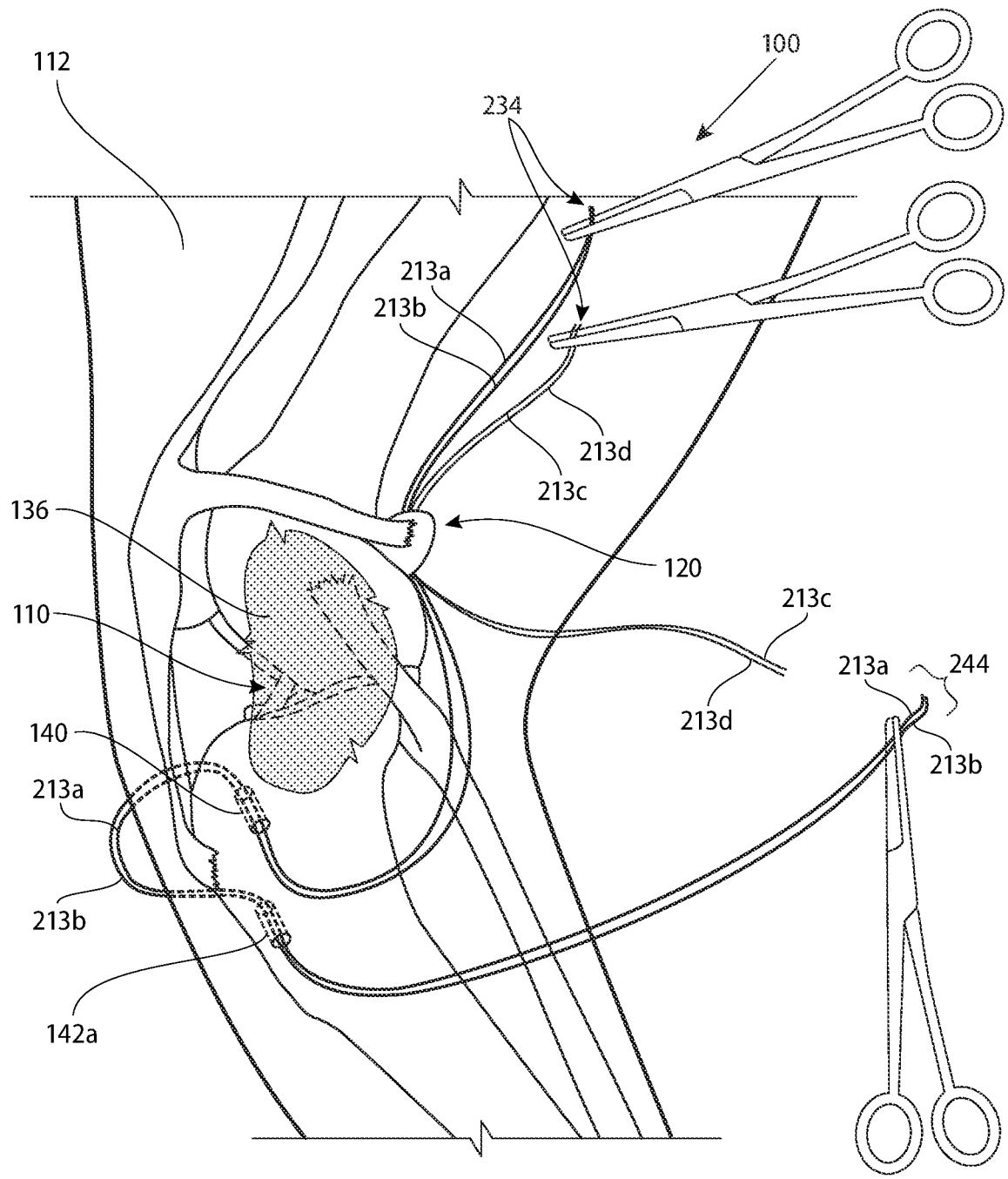
FIG. 13 illustrates a lateral view of a canine stifle with the first and second filament portions of the plurality of filament portions clamped.
Figure 14:
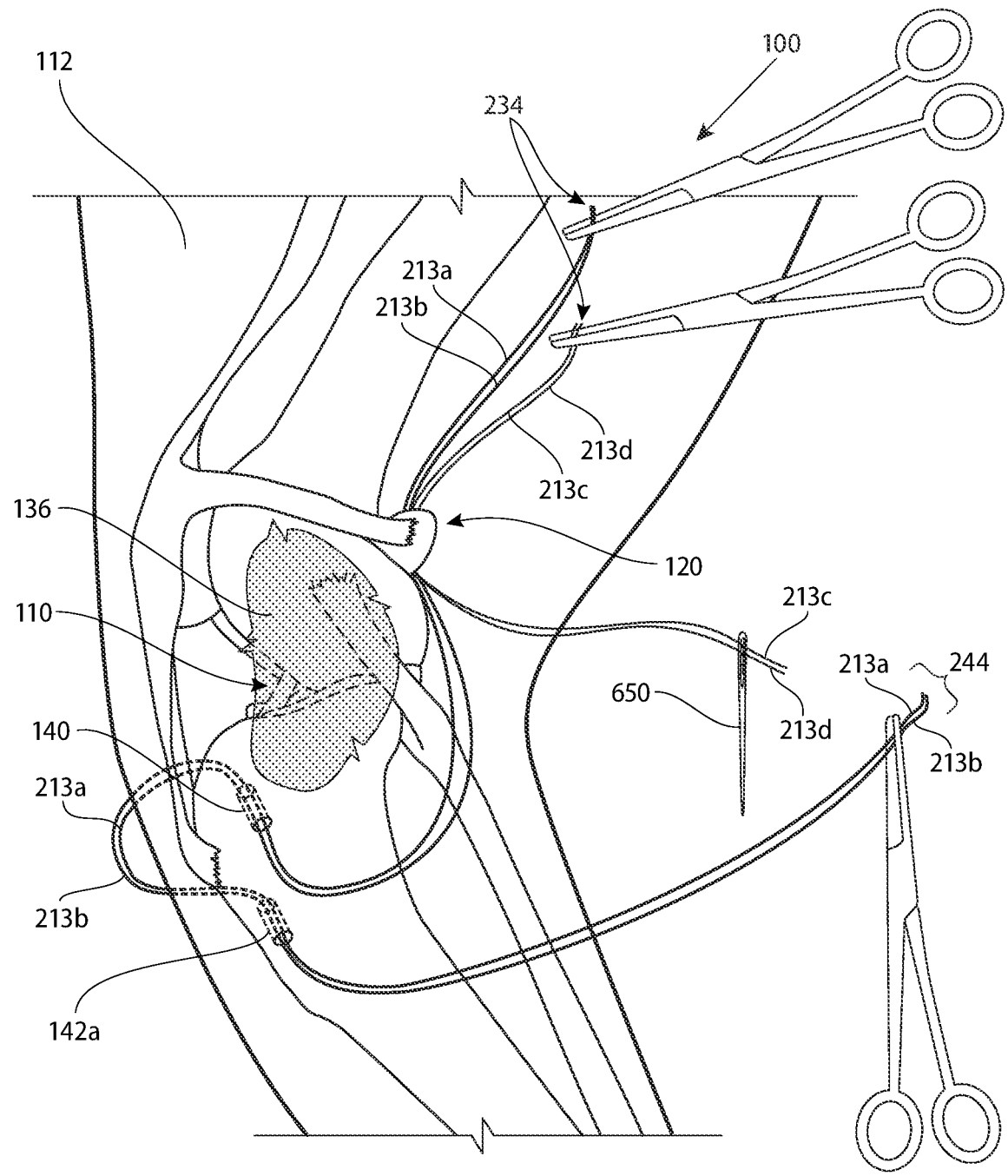
FIG. 14 illustrates a lateral view of a canine stifle with a third and a fourth filament portion of the plurality of filament portions threaded onto a straight needle.
Figure 15A:
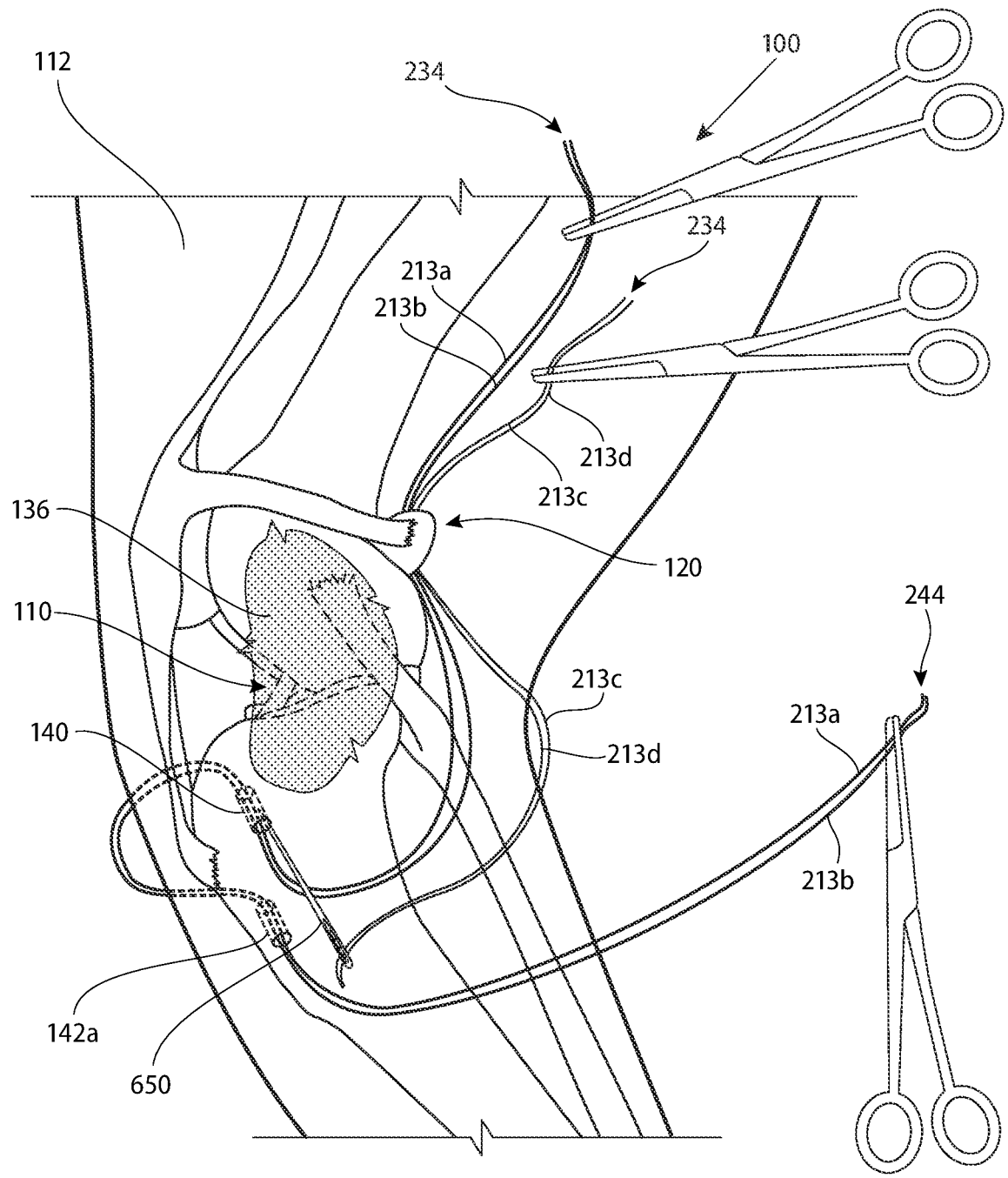
FIG. 15A illustrates a lateral view of a canine stifle with the third and fourth filament portions of the plurality of filament portions threaded onto a straight needle and into a first hole.
Figure 15B:
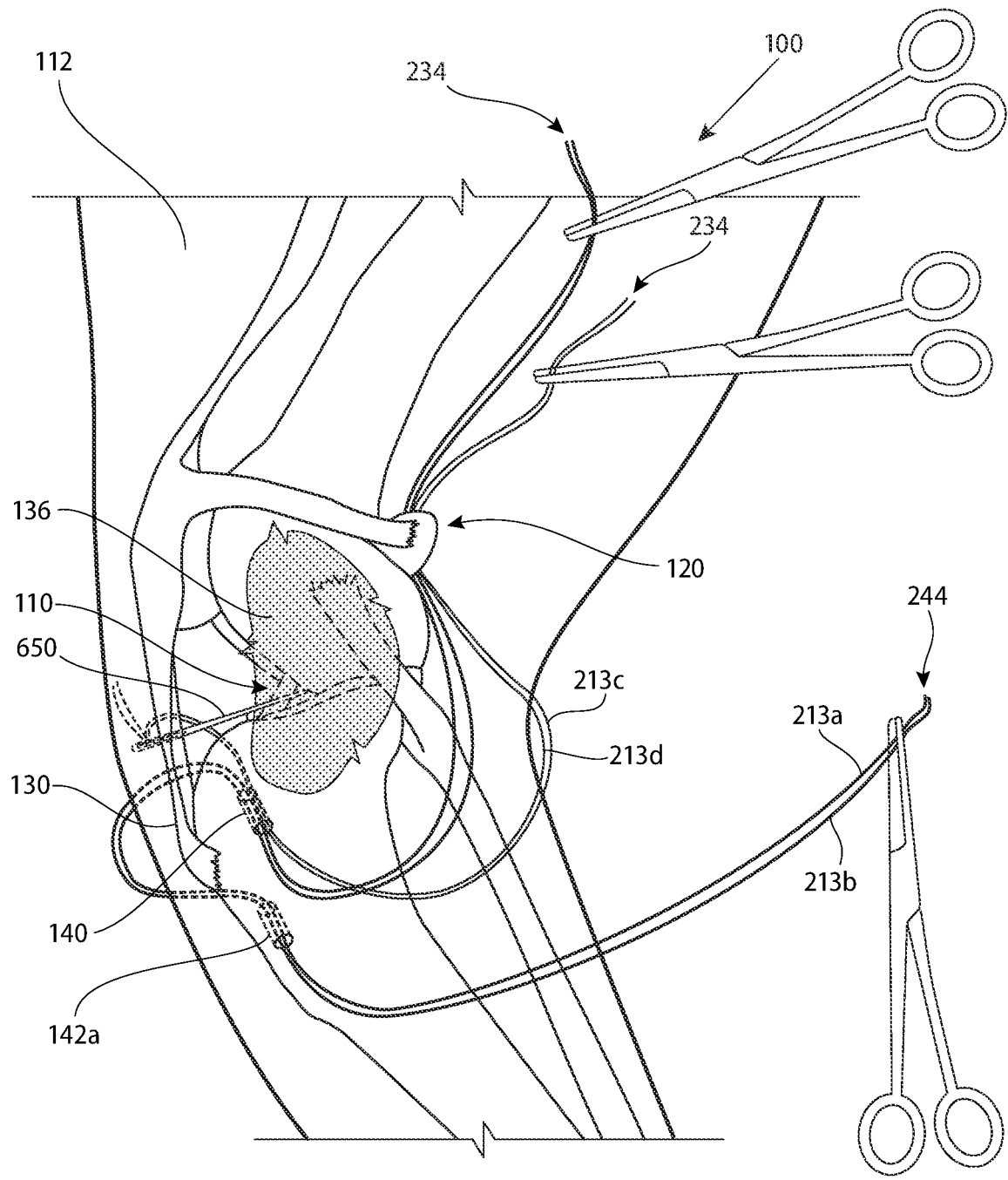
FIG. 15B illustrates a lateral view of a canine stifle with the third and fourth filament portions of the plurality of filament portions threaded on the straight needle, behind a patellar ligament, and under a fascia region.
Figure 16:
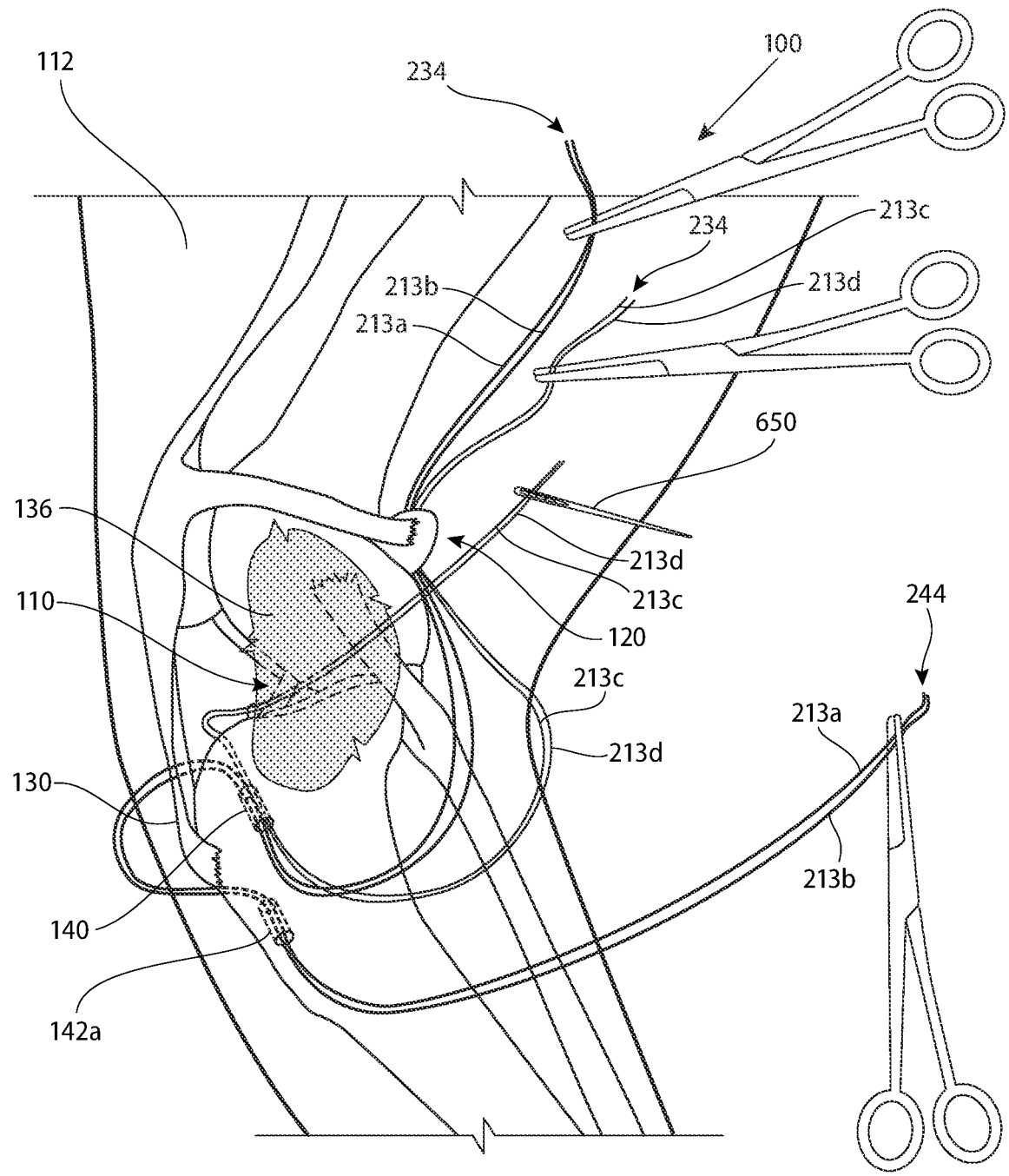
FIG. 16 illustrates a lateral view of a canine stifle with the third and fourth filament portions of the plurality of filament portions threaded on the straight needle and through a fascia region.
Figure 17:
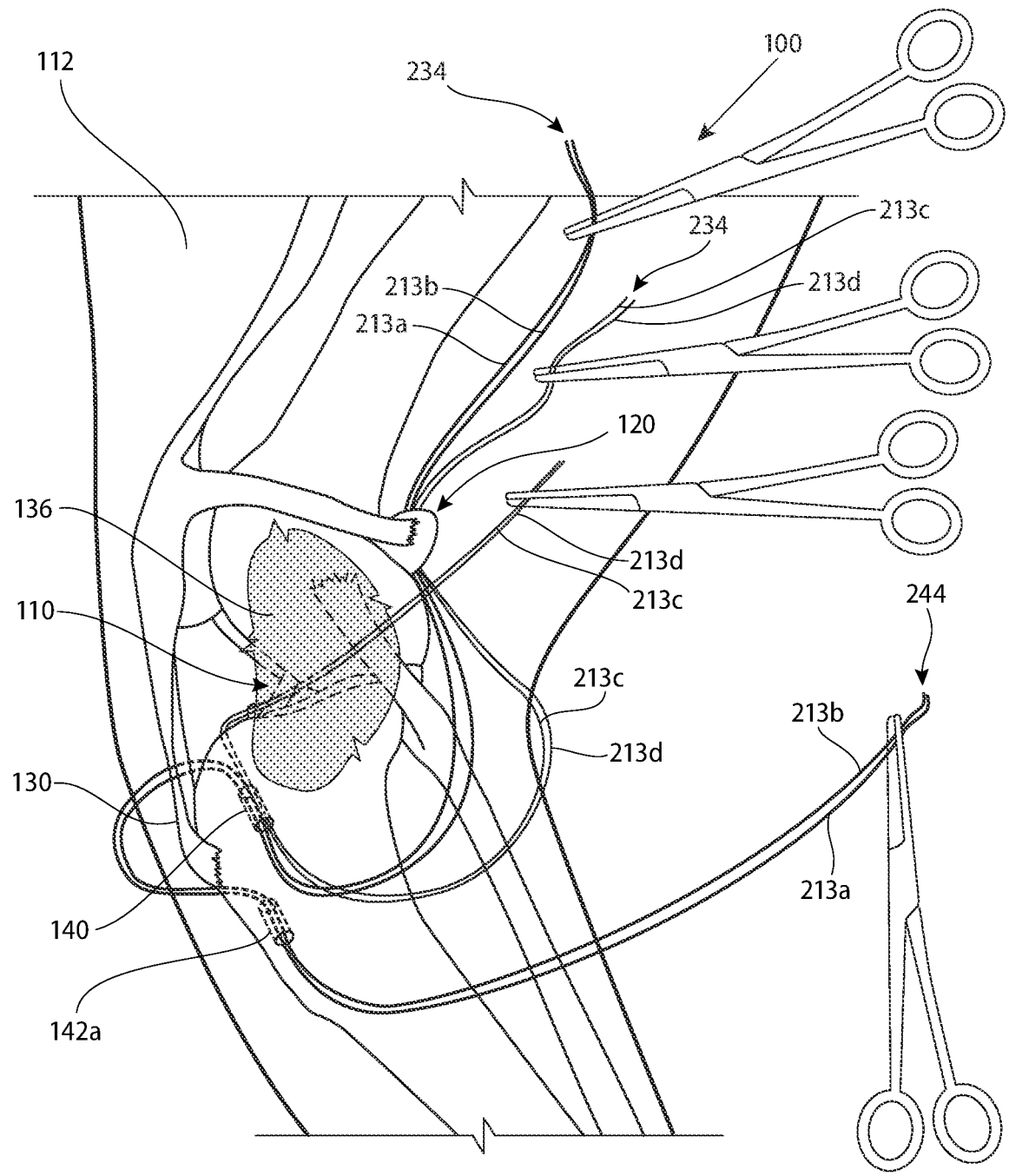
FIG. 17 illustrates a lateral view of a canine stifle with the third and fourth filament portions of the plurality of filament portions clamped.
Figure 18A:
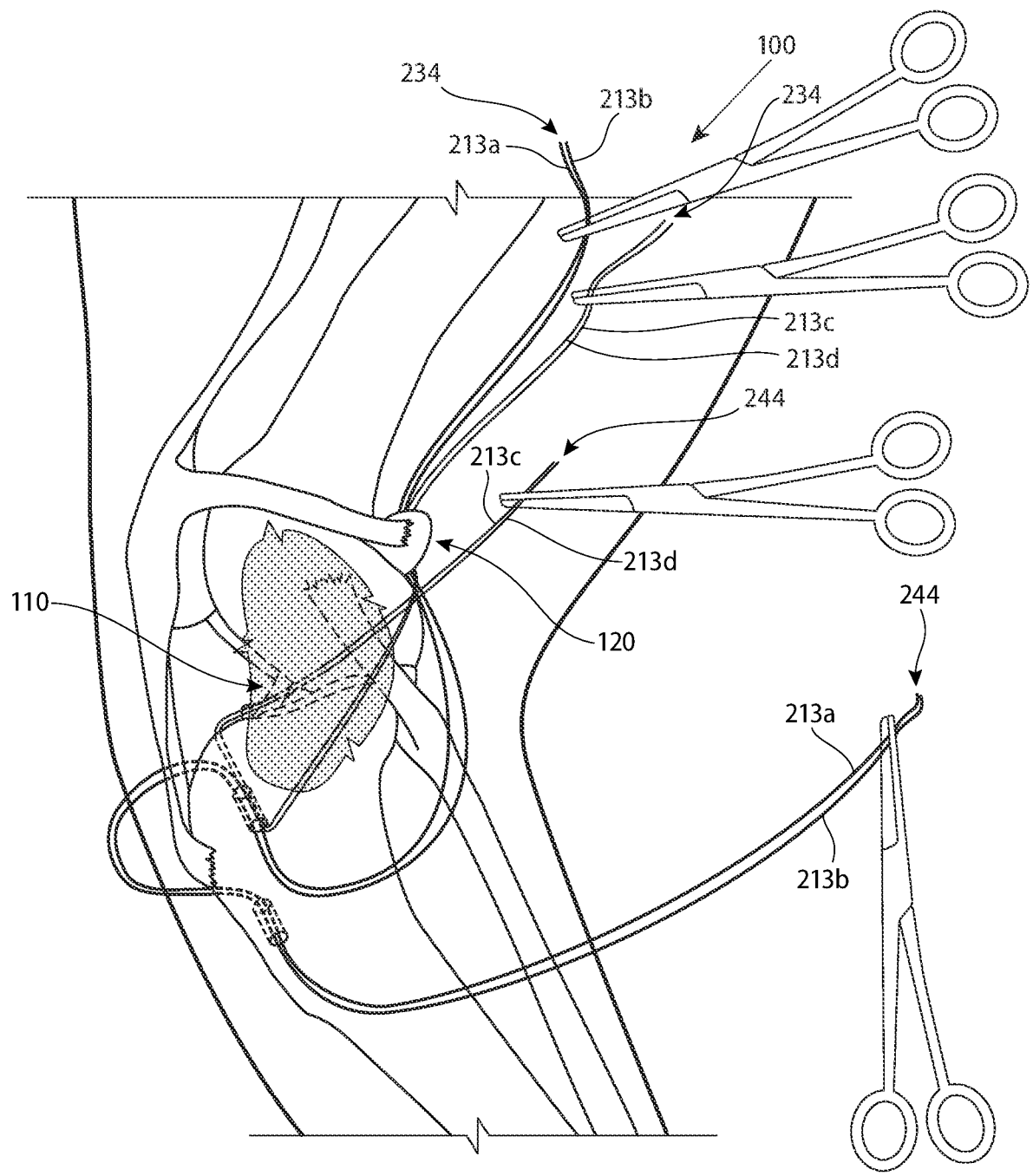
FIG. 18A illustrates a lateral view of a canine stifle with the third and fourth filament portions pulled partly taut.
Figure 18B:
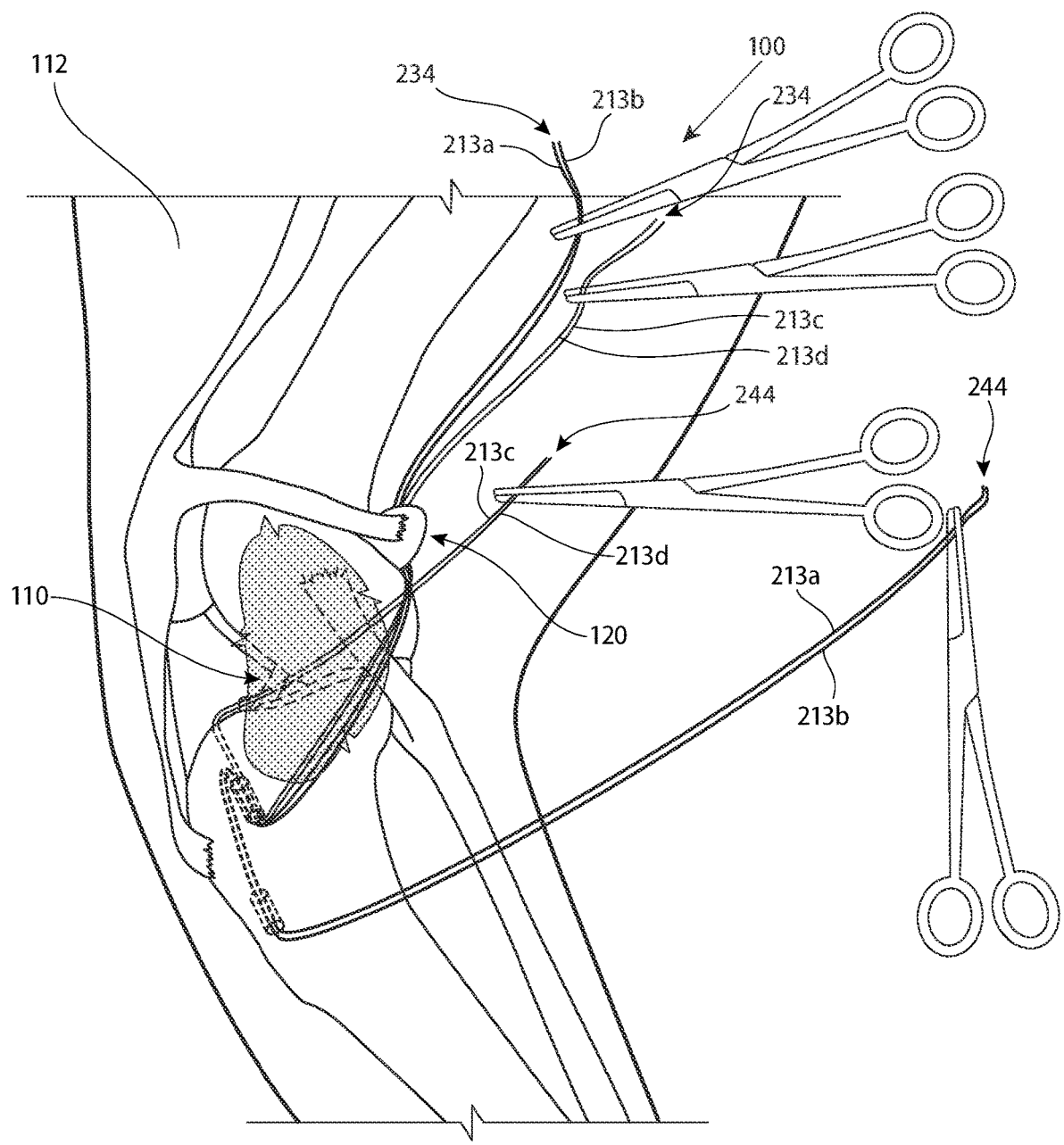
FIG. 18B illustrates a lateral view of a canine stifle with the first and second filament portions pulled partly taut.
Figure 18C:
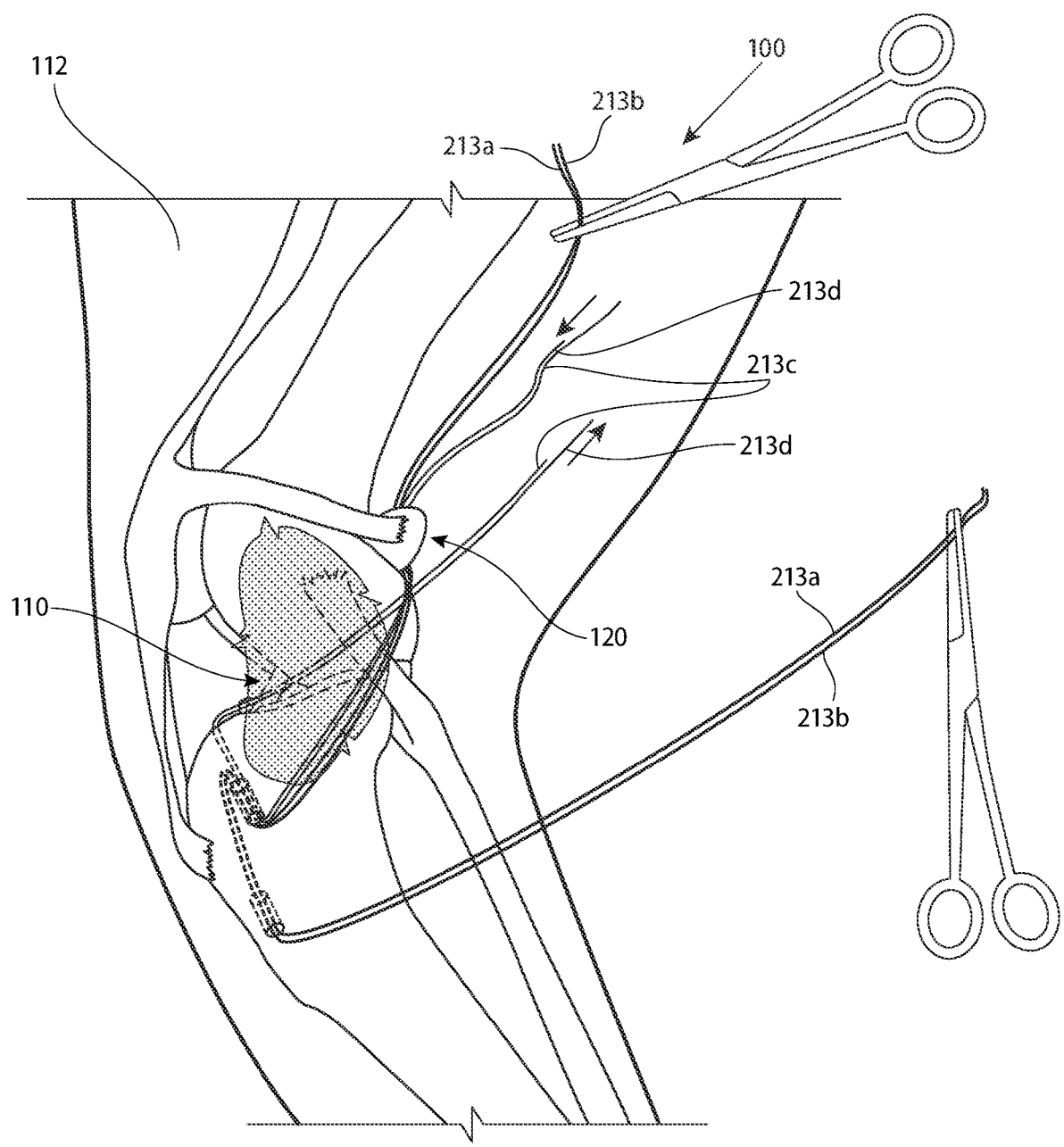
FIG. 18C illustrates a lateral view of a canine stifle with the third and fourth filament portions unclamped, and moved relative to each other to pair their respective ends.
Figure 18D:
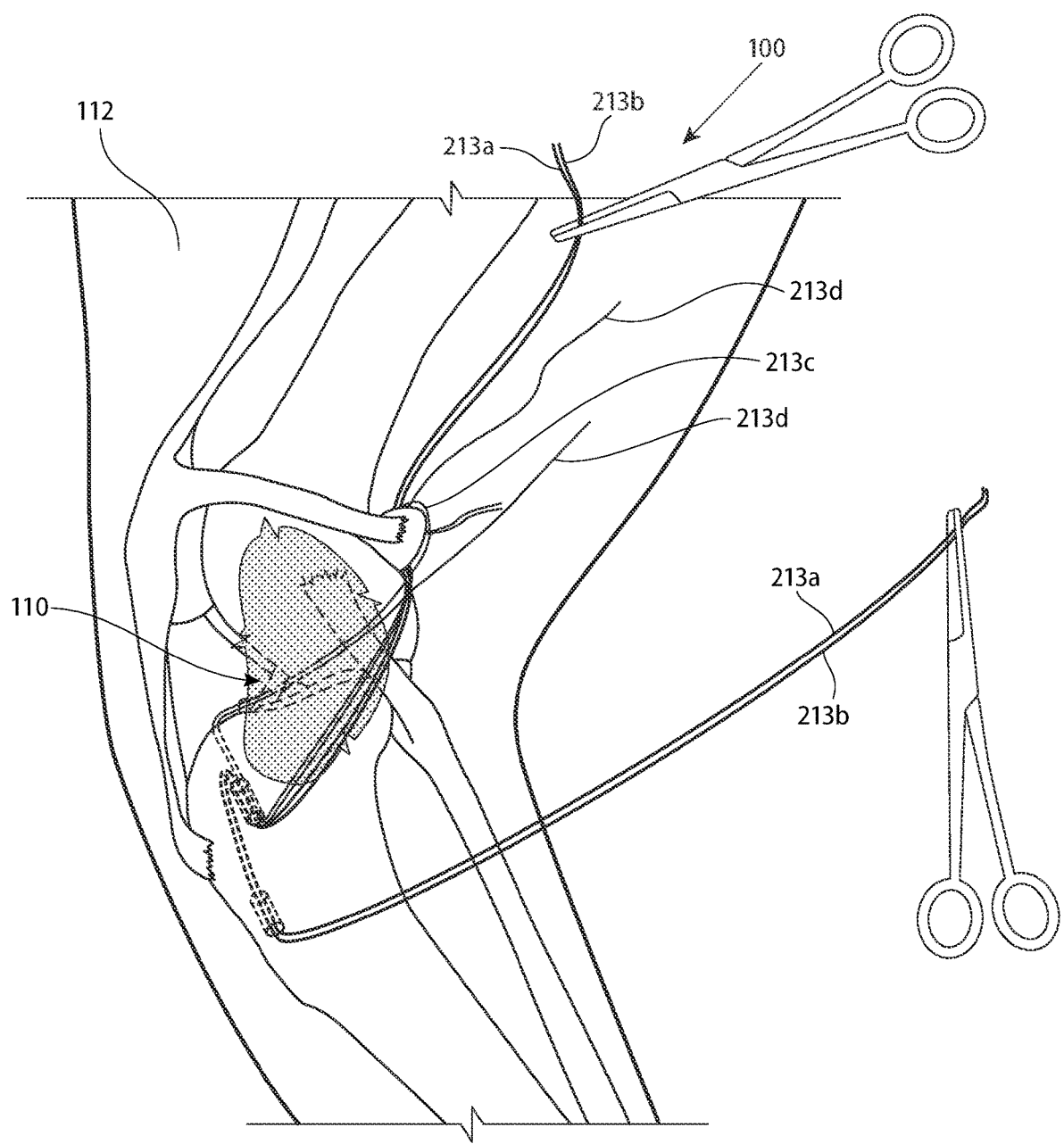
FIG. 18D illustrates a lateral view of a canine stifle with the third and fourth filament portions unclamped, and the ends of the third filament portion connected to each other.
Figure 18E:
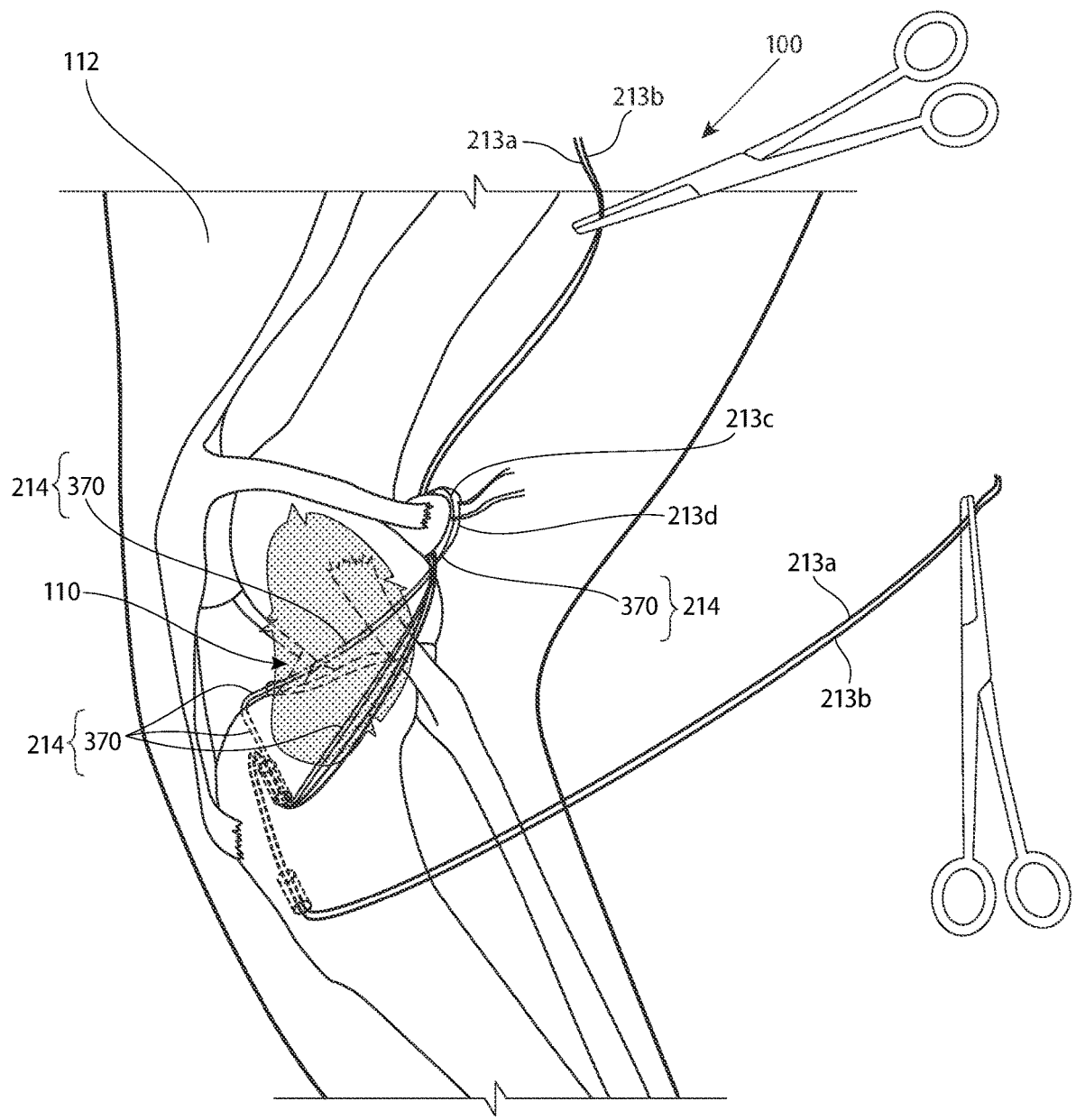
FIG. 18E illustrates a lateral view of a canine stifle with the third and fourth filament portions unclamped, and the ends of the fourth filament portion connected to each other.
Figure 18F:
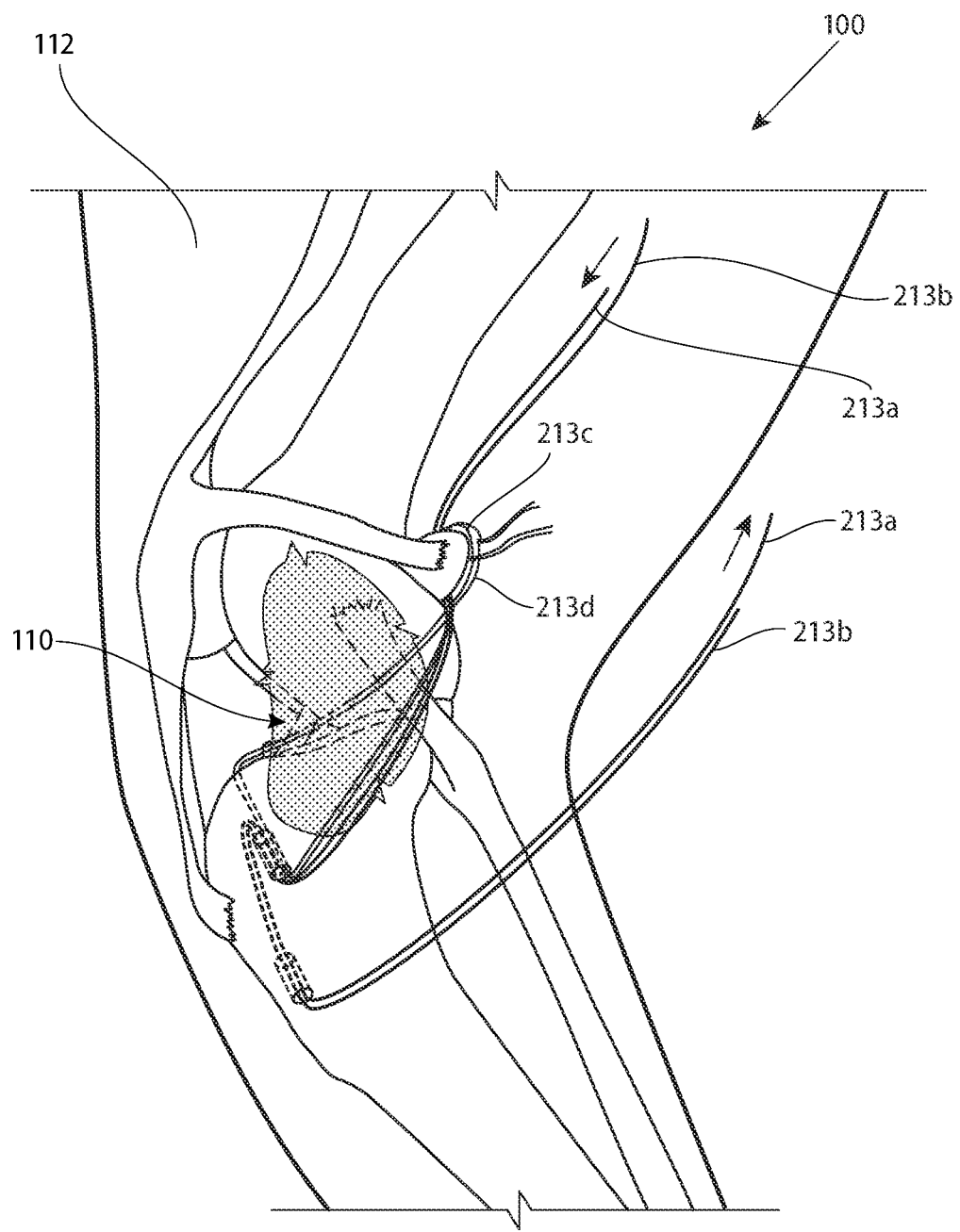
FIG. 18F illustrates a lateral view of a canine stifle with the first and second filament portions unclamped, and moved relative to each other to pair their respective ends.
Figure 18G:
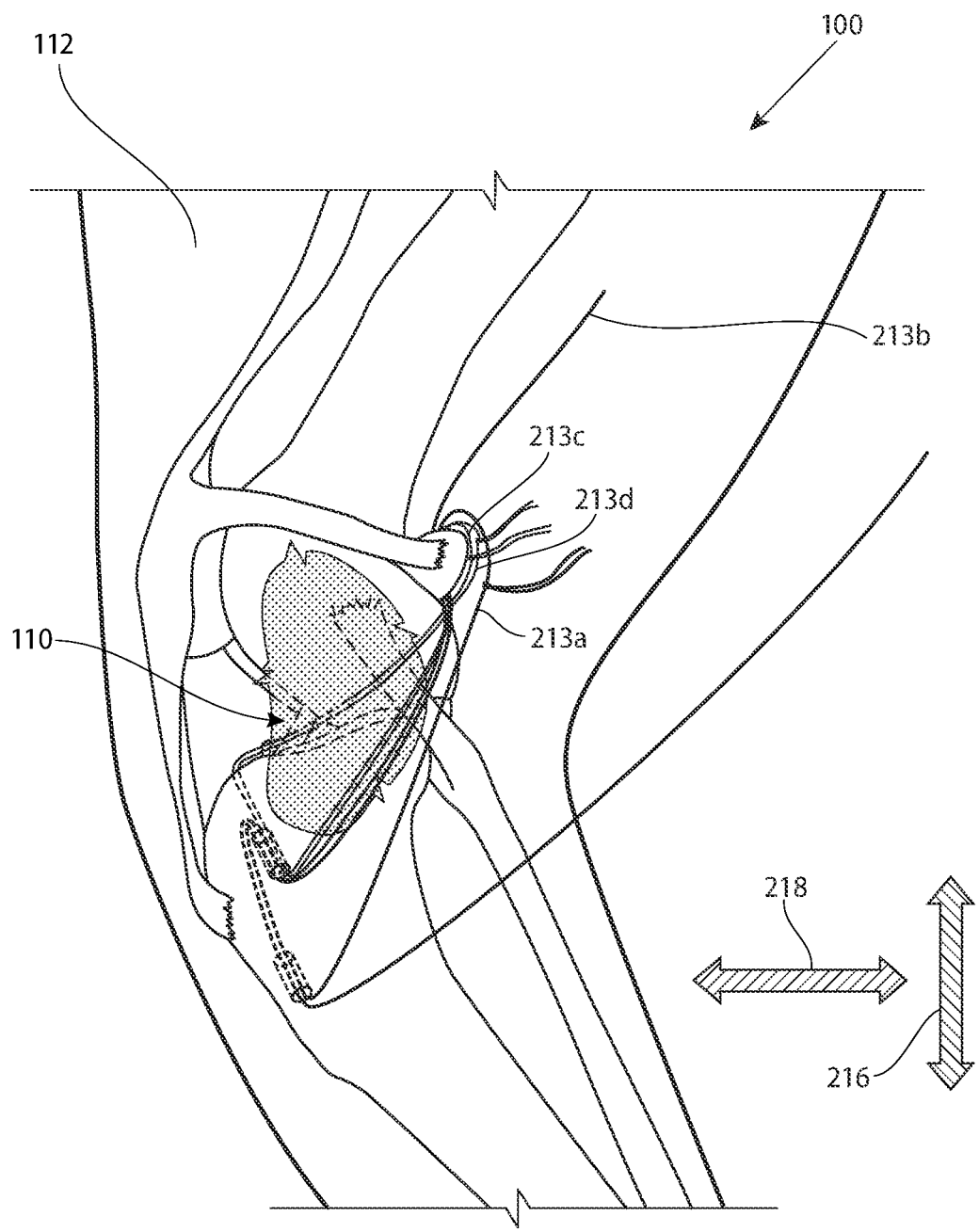
FIG. 18G illustrates a lateral view of a canine stifle with the first and second filament portions unclamped, and the ends of the first filament portion connected to each other.
Figure 18H:
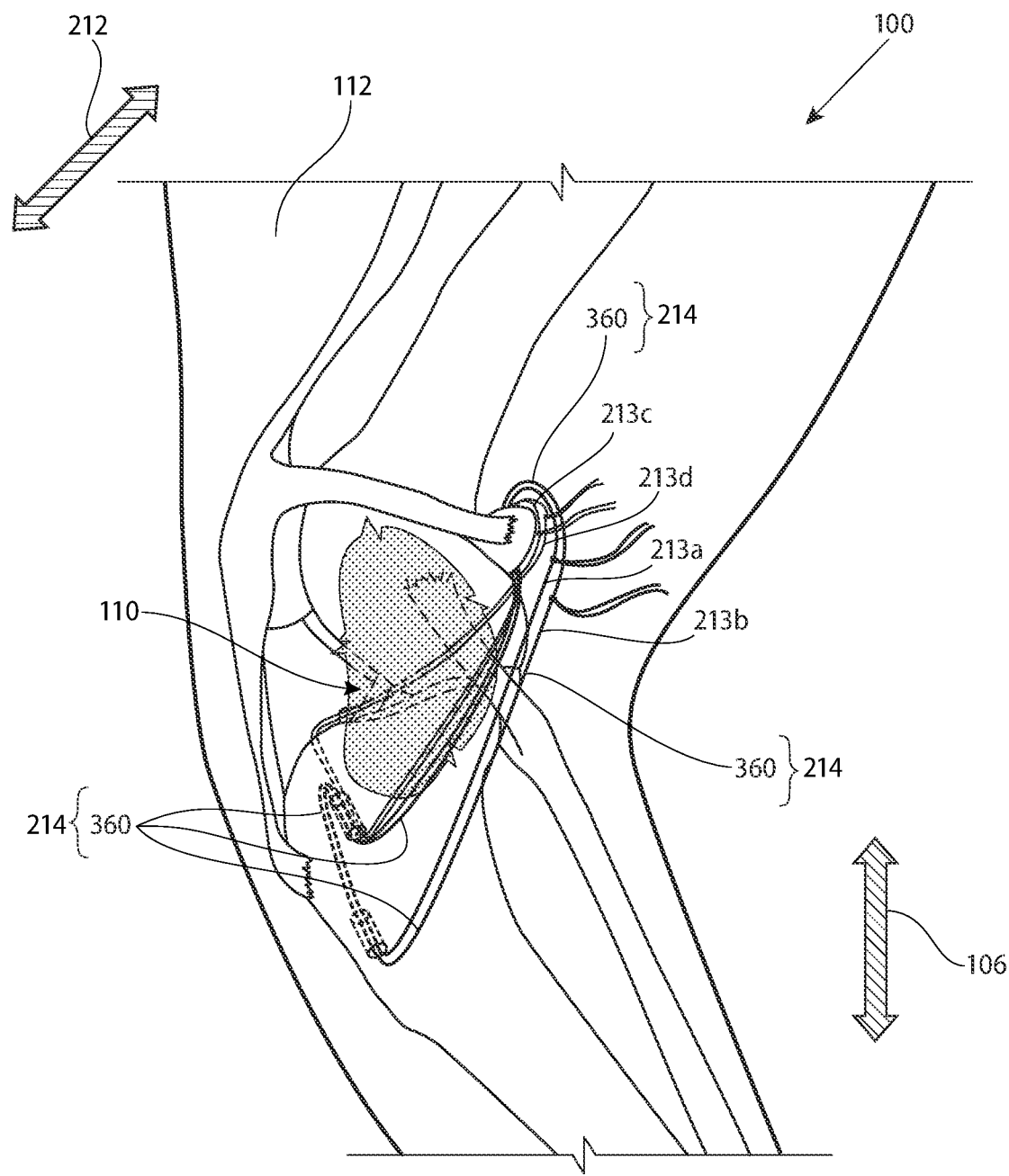
FIG. 18H illustrates a lateral view of a canine stifle with the first and second filament portions unclamped, and the ends of the second filament portion connected to each other.
Figure 19A:
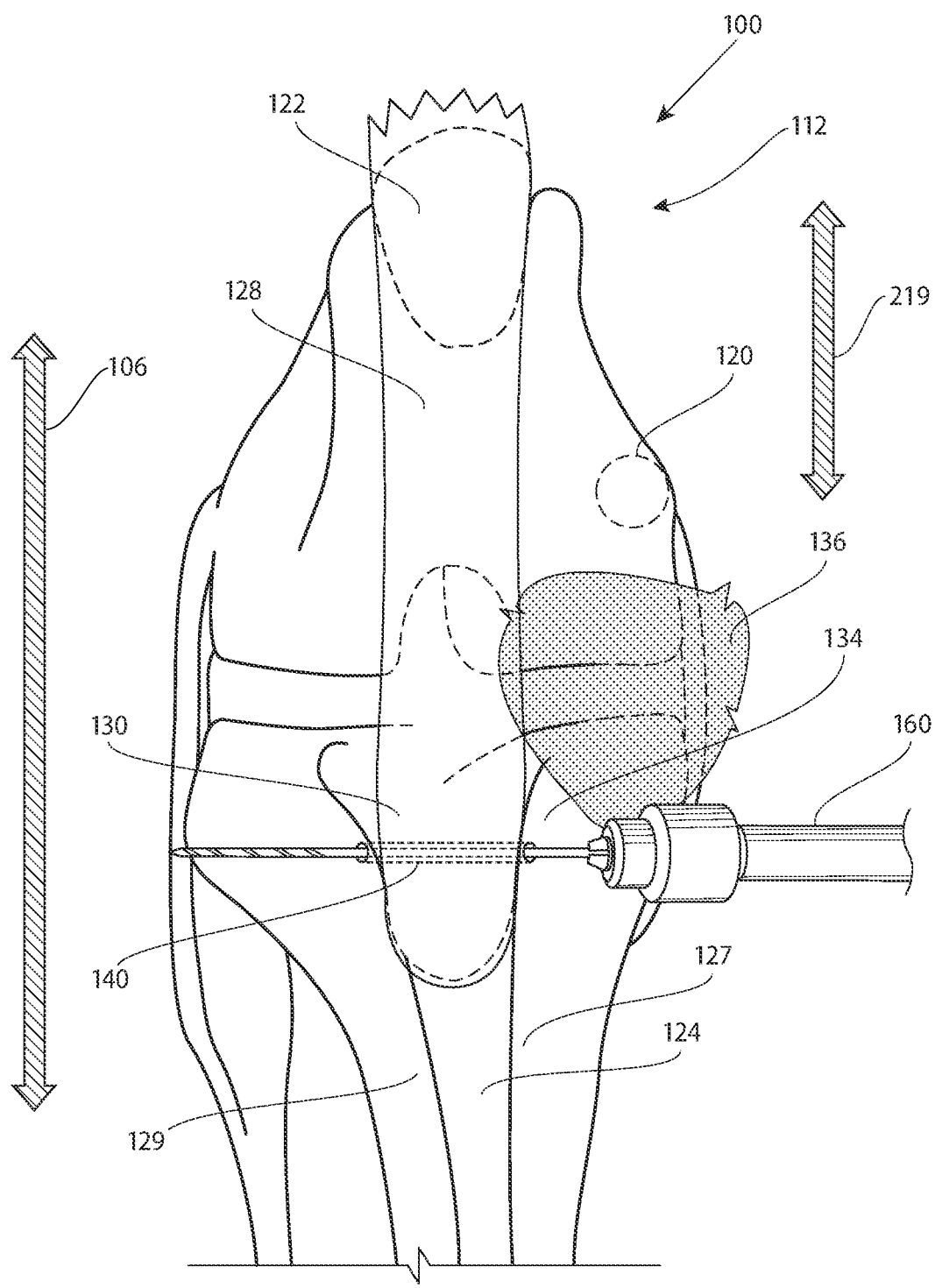
FIG. 19A illustrates a cranial view of the main ligaments and tendons of the canine stifle, with a first hole being drilled through the tibial tuberosity.
Figure 19B:
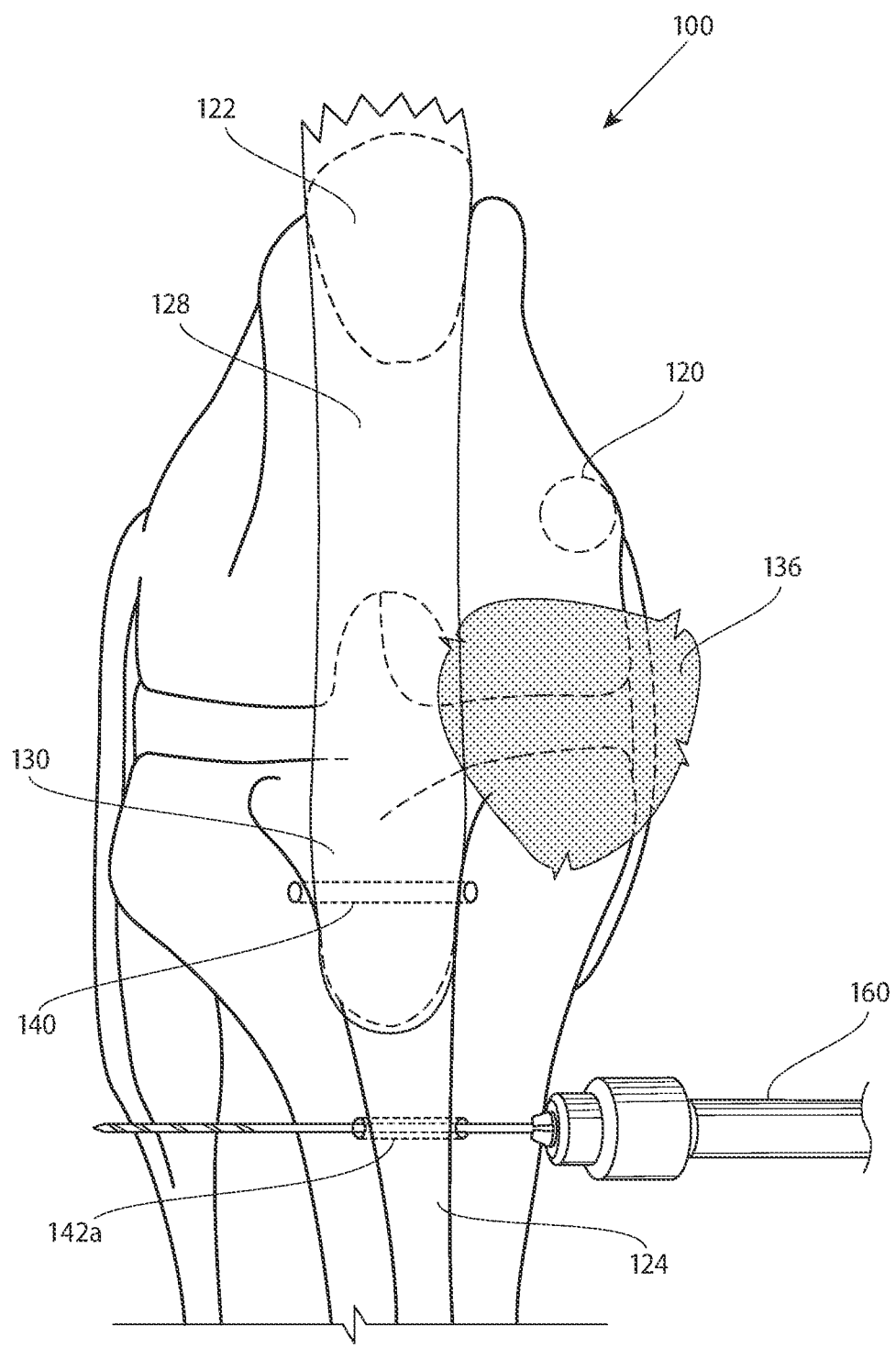
FIG. 19B illustrates a cranial view of the main ligaments and tendons of the canine stifle, with a second hole being drilled through the tibial tuberosity in a first location.
Figure 19C:
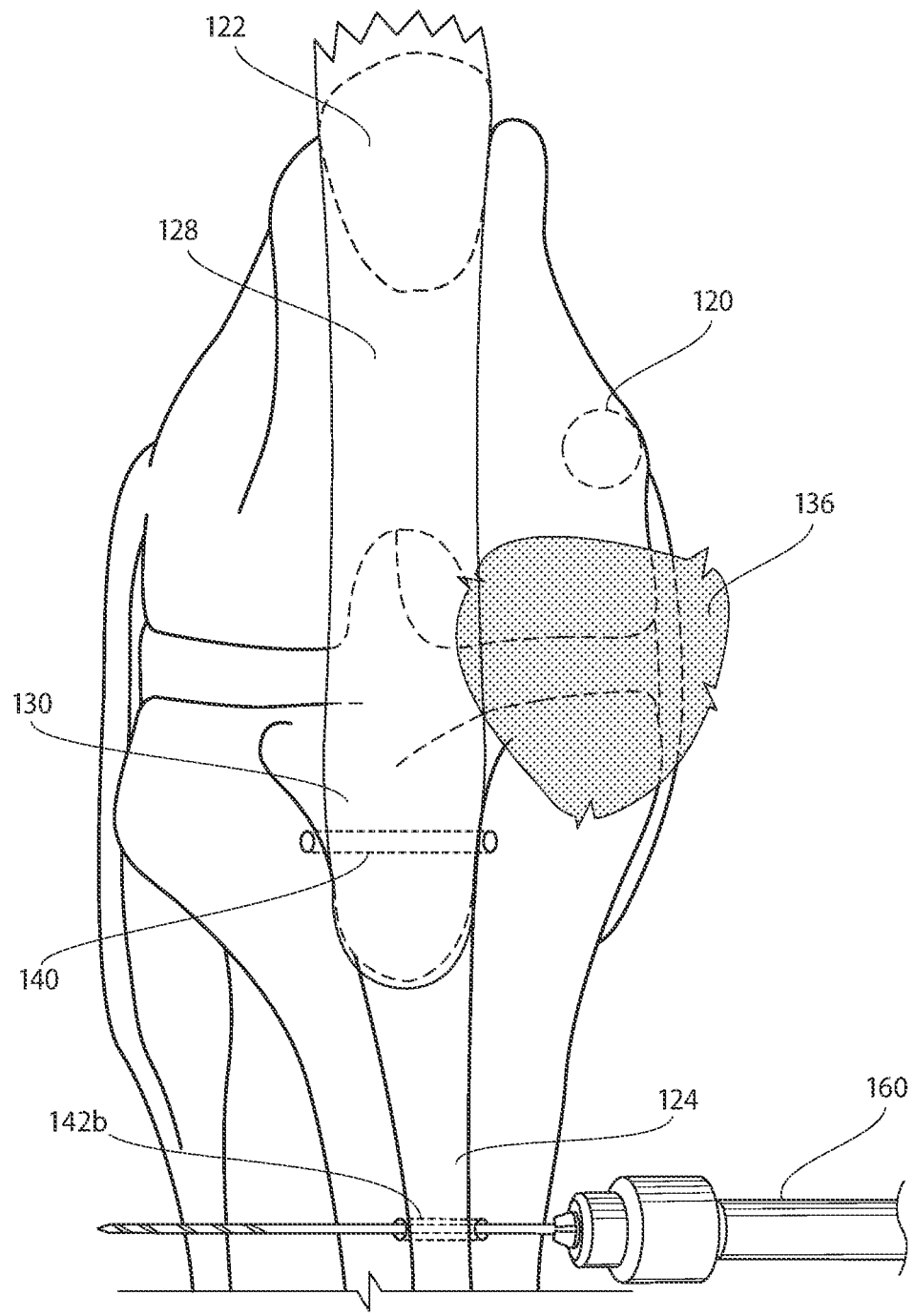
FIG. 19C illustrates a cranial view of the main ligaments and tendons of the canine stifle, with a second hole being drilled through the tibial tuberosity in a second location.
Figure 20A:
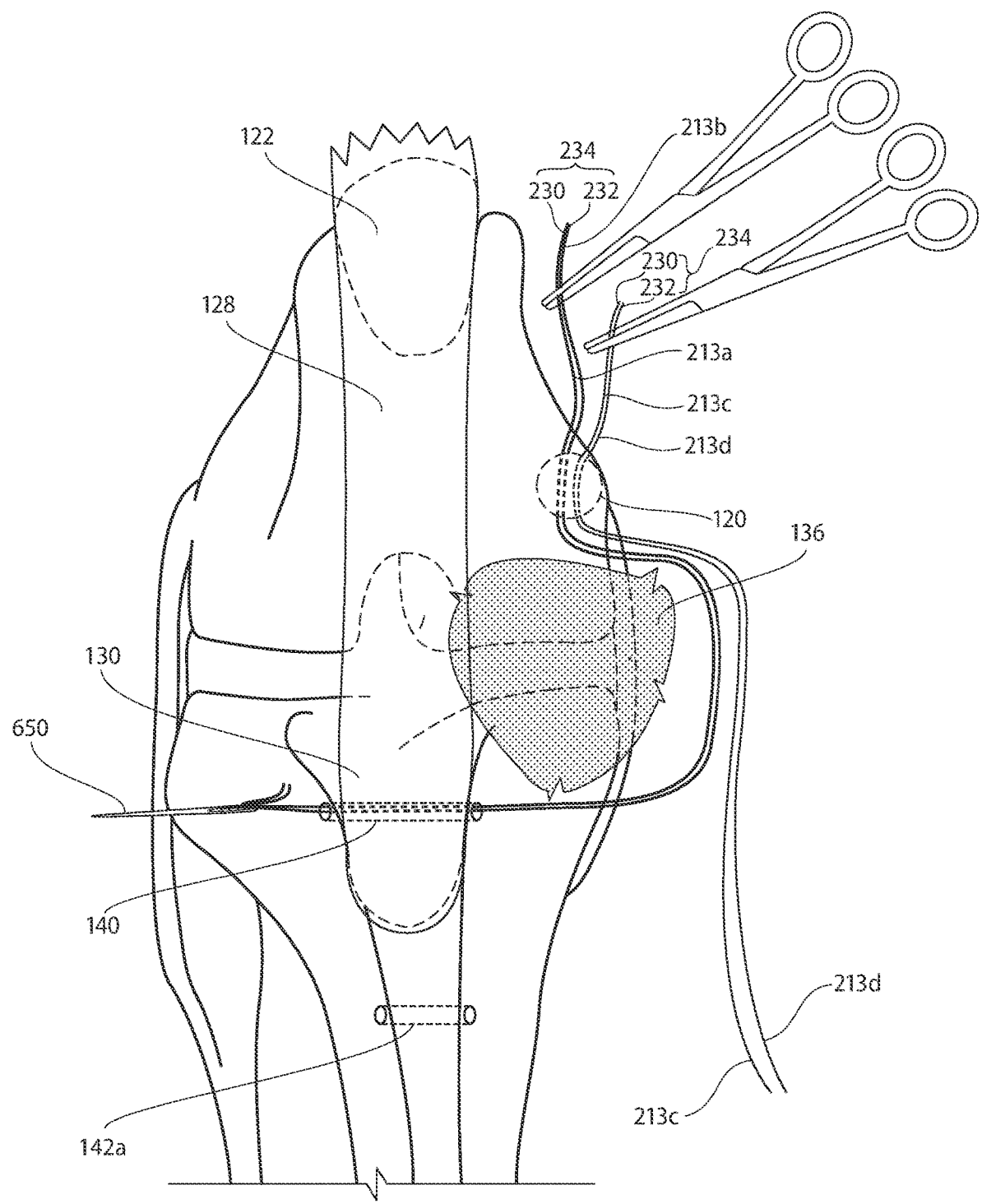
FIG. 20A illustrates a cranial view of the main ligaments and tendons of the canine stifle with the one or more filaments severed to become the plurality of filament portions, and the first and the second filament portion of the plurality of filament portions threaded onto a straight needle and into the first hole.
Figure 20B:
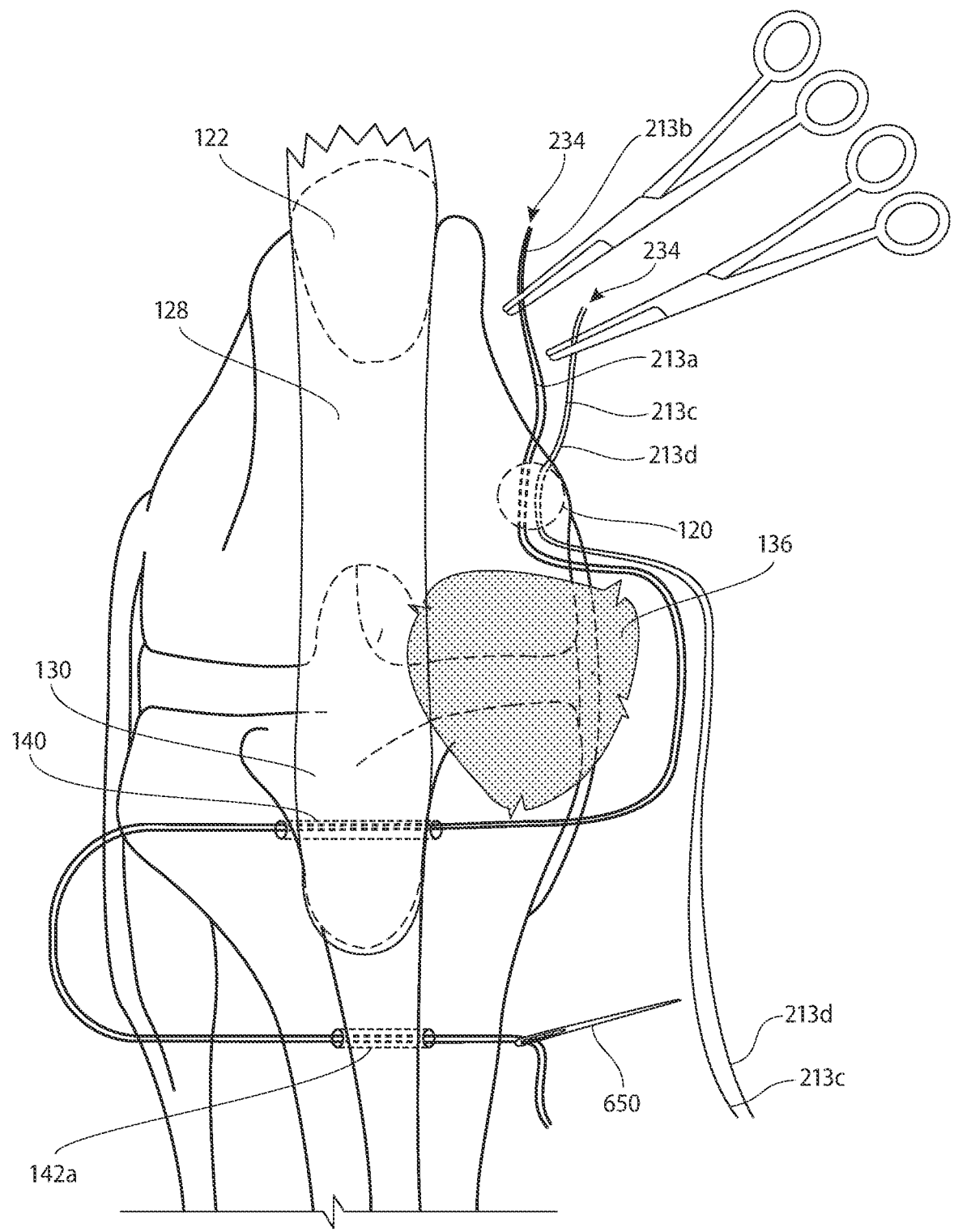
FIG. 20B illustrates a cranial view of the main ligaments and tendons of the canine stifle with the first and second filament portions of the plurality of filament portions threaded onto a straight needle and through a second hole.
Figure 21:
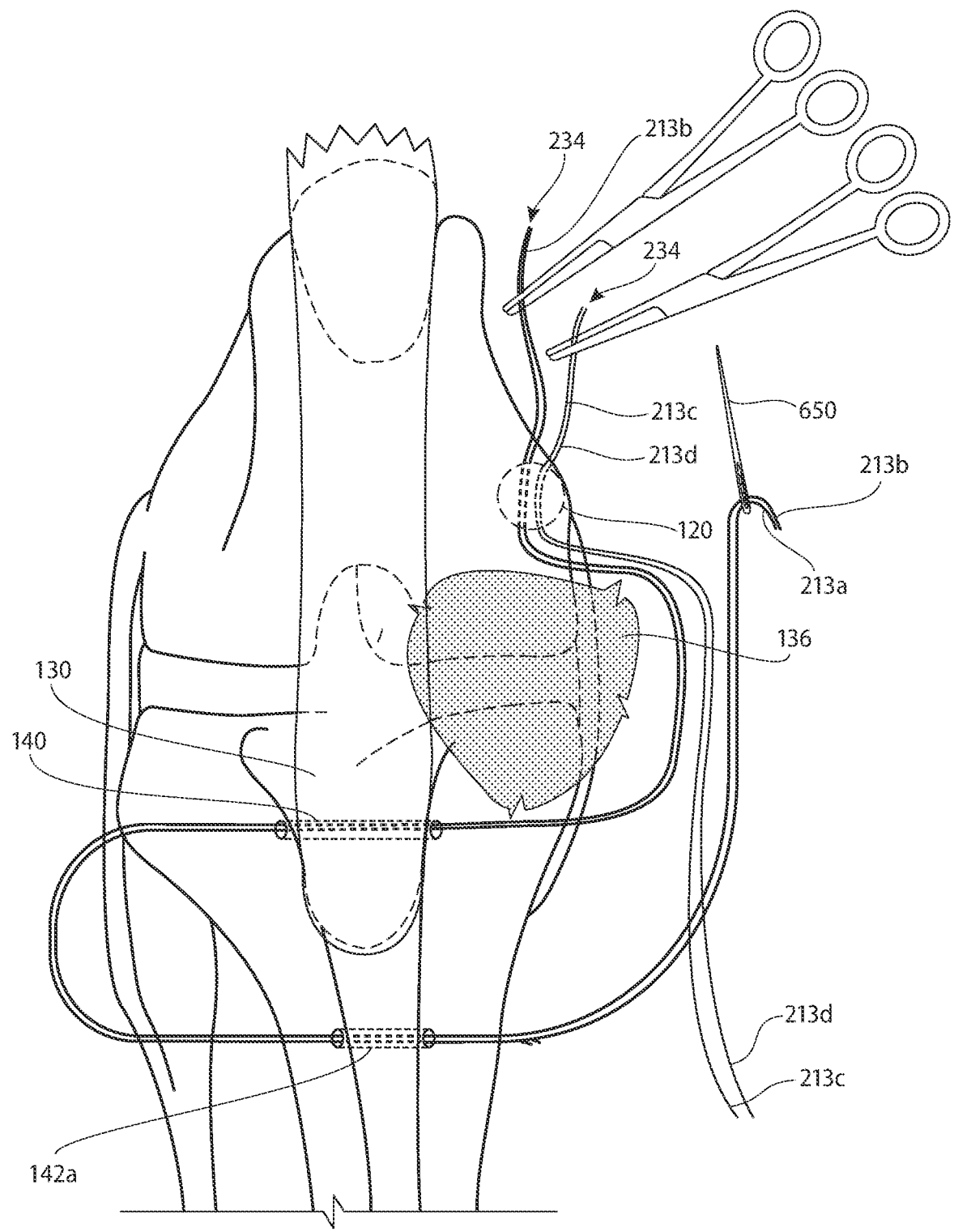
FIG. 21 illustrates a cranial view of the main ligaments and tendons of the canine stifle with the first and second filament portions of the plurality of filament portions threaded onto a straight needle and through a second hole.
Figure 22:
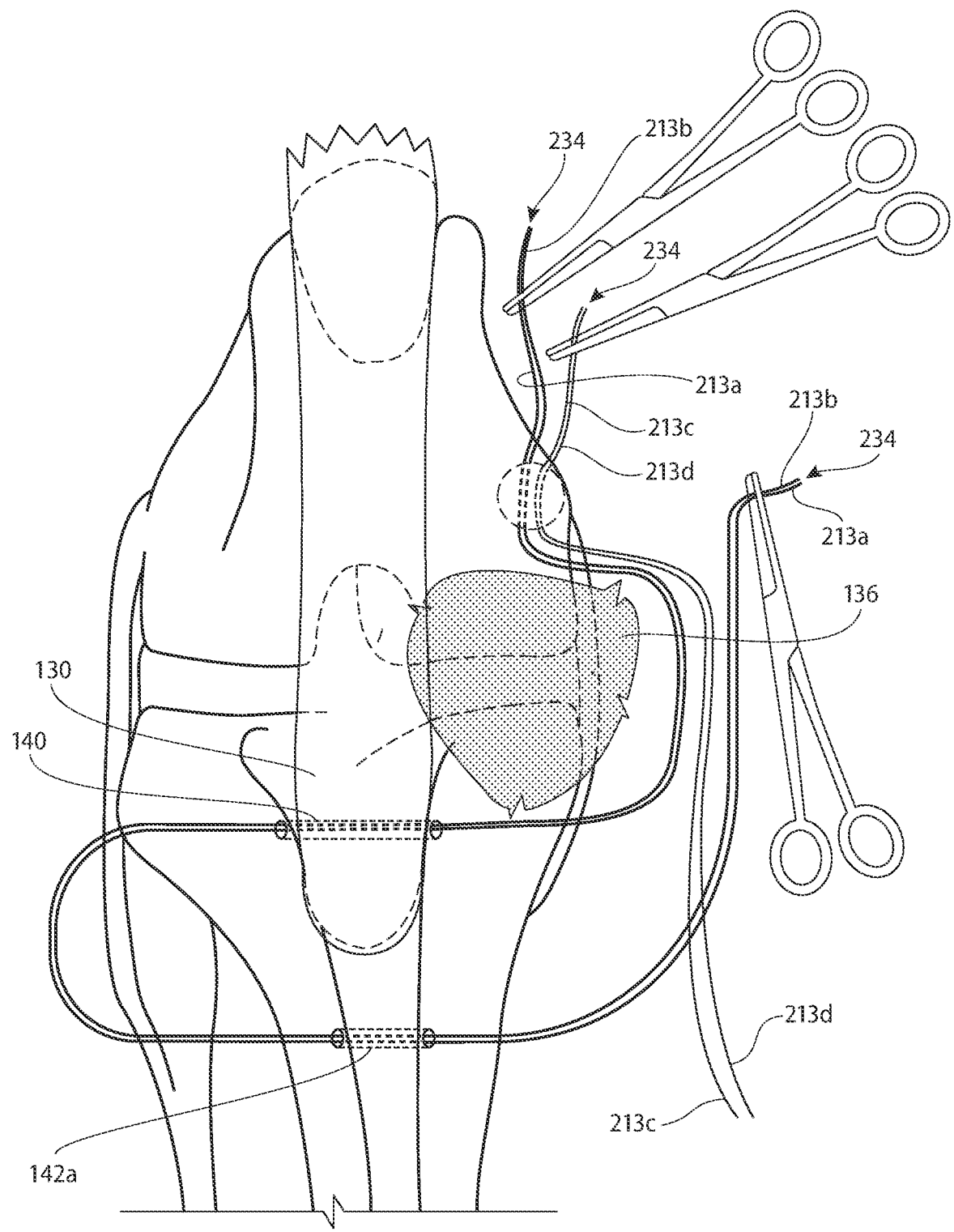
FIG. 22 illustrates a lateral view of a canine stifle with the first and second filament portions of the plurality of filament portions clamped.
Figure 23:
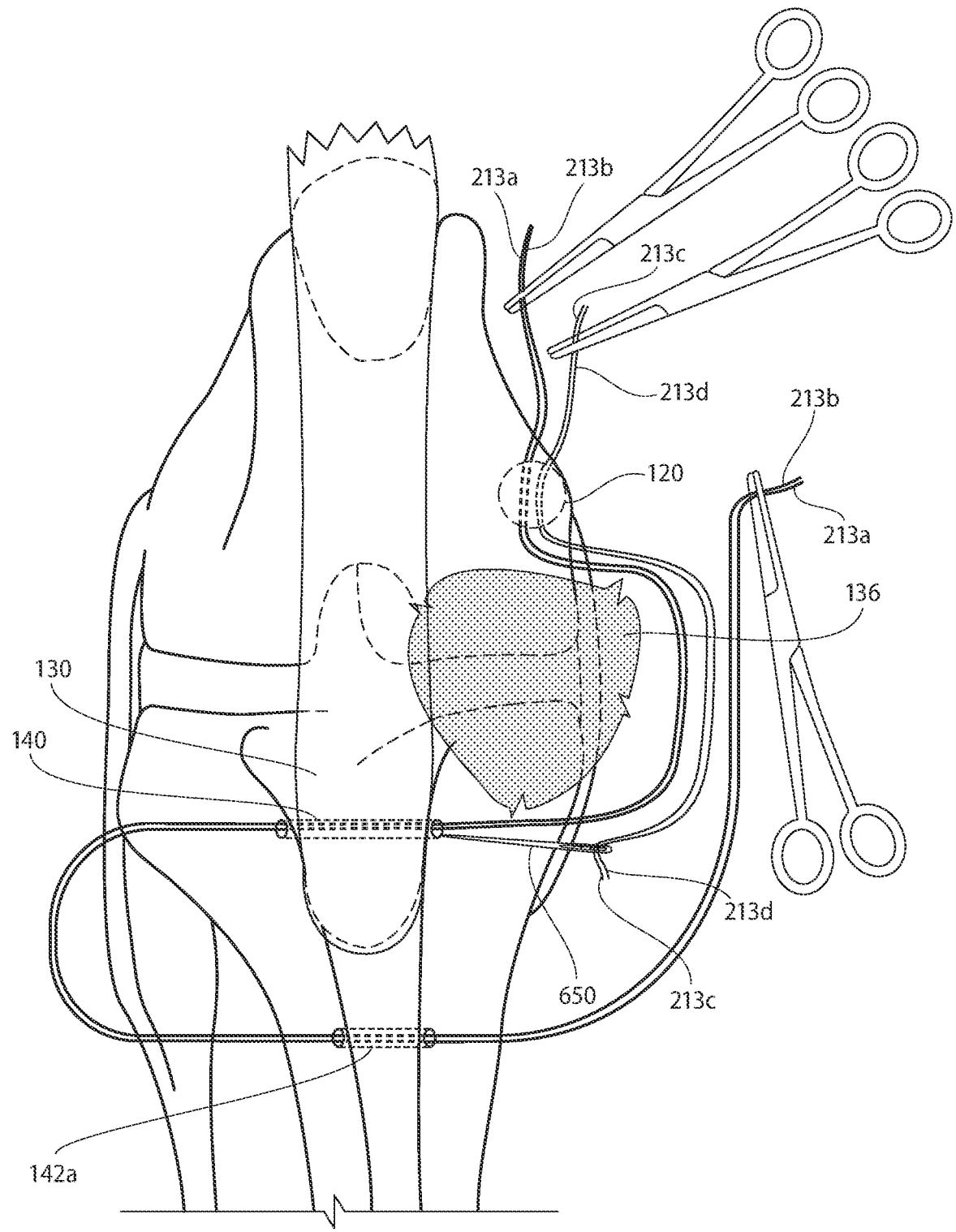
FIG. 23 illustrates a lateral view of a canine stifle with a third and a fourth filament portion of the plurality of filament portions threaded onto a straight needle.
Figure 24:
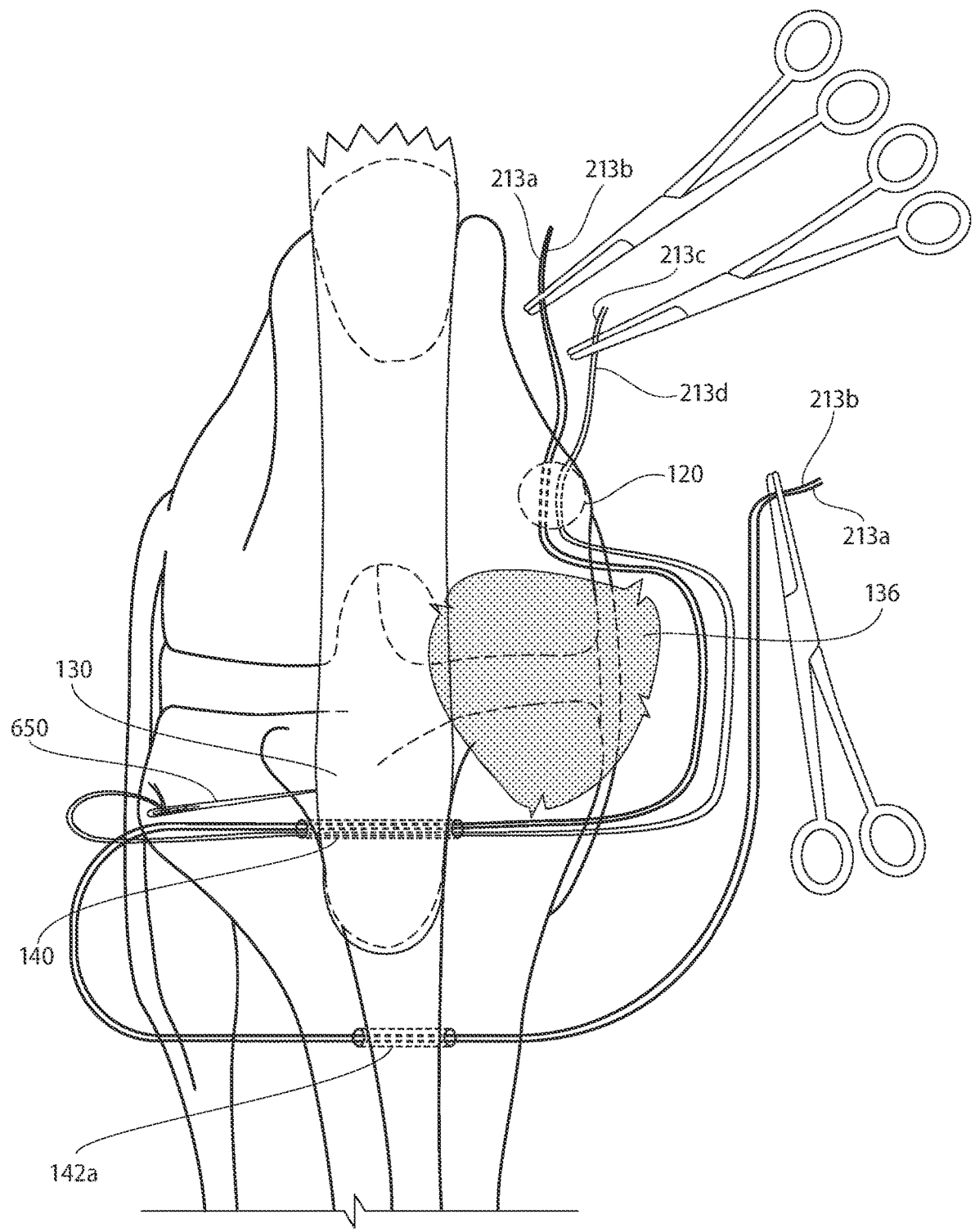
FIG. 24 illustrates a lateral view of a canine stifle with a third and a fourth filament portion of the plurality of filament portions threaded onto a straight needle and through the first hole.
Figure 25:
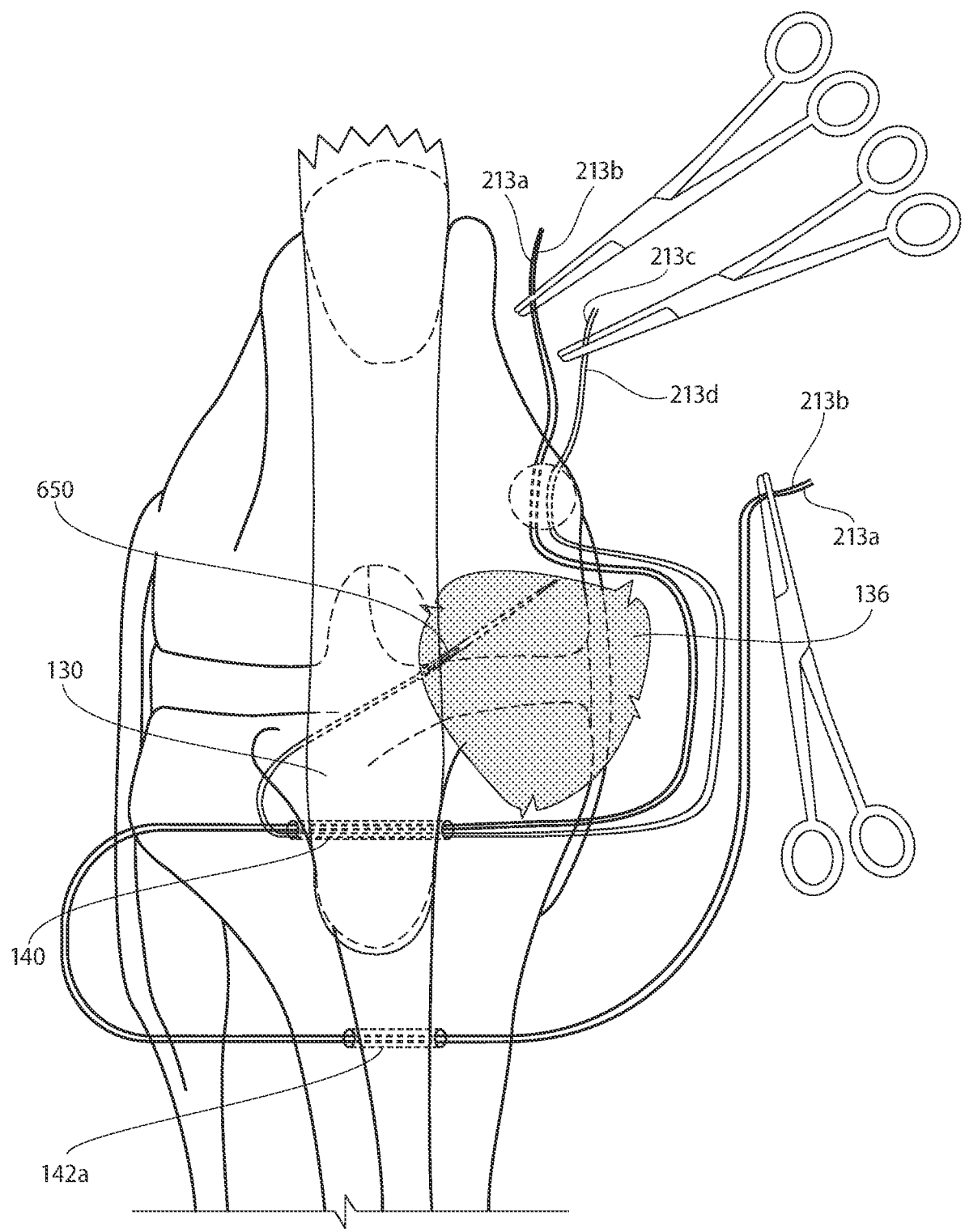
FIG. 25 illustrates a lateral view of a canine stifle with a third and a fourth filament portion of the plurality of filament portions threaded onto a straight needle, through the first hole, behind the patella ligament, and under a fascia region.
Figure 26:
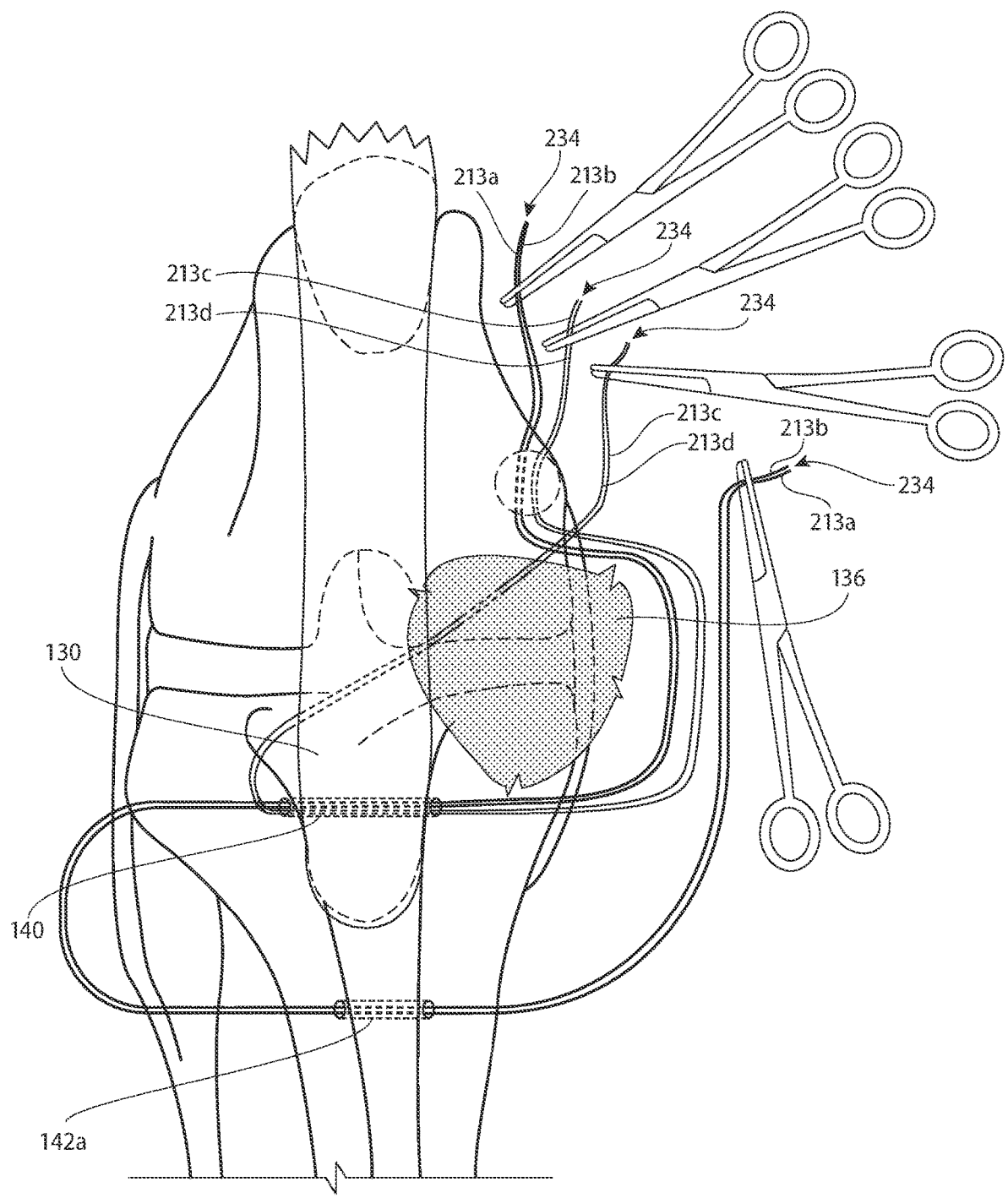
FIG. 26 illustrates a lateral view of a canine stifle with a third and a fourth filament portion of the plurality of filament portions threaded onto a straight needle, through the first hole, behind the patella ligament, under a fascia region, and clamped.

In some aspects of the present disclosure, and with reference to FIG. 14, FIG. 15A, FIG. 15B, FIG. 16, FIG. 17, FIG. 18A, FIG. 18B, FIG. 18C, FIG. 18D, FIG. 18E, FIG. 23, FIG. 24, FIG. 25, and FIG. 26, the craniomedial pathway 370 can be established to form a crossing figure-8 pattern. In such aspects, the other half, or other suitable number or portion, of the total of the first clamped ends 234 of the one or more filaments 210 are threaded through the eye of, in the threading-step 380, the straight elongated eye stacking needle 650. The straight elongated eye stacking needle 650 is then passed, in a fourth-passing-step 394, behind the full thickness of the patella ligament 130 at the distal-most point of the patella ligament 130, just proximal to an attachment of the patella ligament 130 to the tibial tuberosity 124, from lateral to medial, passing between the patella ligament 130 and the joint capsule. With the fourth-passing-step 394, the craniomedial pathway 370 first traverses over the cranial aspect of the stifle joint 104. The straight elongated eye stacking needle 650 is then passed, in a fifth passing-step 396, through the first hole 140, being the proximal-most hole in the tibial tuberosity 124, from medial back to lateral. The straight elongated eye stacking needle 650 is then carried, in fourth carrying-step 398 proximally through the fascia tissue 136 on the lateral aspect of the stifle joint 104, being careful not to perforate the joint capsule. Each of the first clamped ends 234 used in the preceding steps are then paired with the second clamped ends 244 used in the preceding steps and corresponding to the first clamped ends 234 on each of the one or more filaments 210, clasping them together in a fifth clasping step 399, using Kelly hemostats or other suitable instruments. In some aspects of the present disclosure, one or more of the one or more filaments 210 may be passed separately on the caudolateral pathway 360 or the craniomedial pathway 370, that is, the plurality of filament portions 213 that were formed from a single one of the one or more filaments 210 may be separated, with one of the plurality of filament portions 213 being placed and threaded on the caudolateral pathway 360 and the other of the plurality of filament portions 213 being placed and threaded on the craniomedial pathway 370. For instance, and without limiting the foregoing, the first filament portion 213a may be placed on the caudolateral pathway 360 and the second filament portion 213b may be placed on the craniomedial pathway 370, or the first filament portion 213a may be placed on the craniomedial pathway 370 and the second filament portion 213b may be placed on the caudolateral pathway 360. This may be done for any of the plurality of filament portions 213.

Thereafter, and with continued reference to FIG. 18A, FIG. 18B, FIG. 18C, FIG. 18D, FIG. 18E, FIG. 18F, FIG. 18G, and FIG. 18H, each of the one or more filaments 210 are then pulled tight, in a pulling-step 390, until each of the one or more filaments 210 are all taut within and along their respective pathways (the caudolateral pathway 360 and the craniomedial pathway 370). The first clamped ends 234 and the second clamped ends 244 of the one or more filaments 210, and any of the plurality of filament portions 213 that are separated and not clamped as pairs of the plurality of filament portions 213, comprising both of the foregoing loading pathways must then be connected together, in a connecting-step 392, in a taut and secure manner, either by tying knots (it has been found advantageous to have six throws each, though other numbers of knots have been found suitable, as will be appreciated by one of skill in the art) or using a suitable surgical crimping device or system. In some aspects of the present disclosure, the filament knots or attachments may be connected in the vicinity of the lateral fabella 120, and/or approximately near a lateral aspect of the stifle joint 104. In other aspects of the present disclosure, the filament knots or attachments may be connected approximately near the vicinity of the tibial tuberosity 124. In other aspects of the present disclosure, the filament knots or attachments may be connected in another region in the surgical field, or in more than one such region. Connecting, in the connecting-step 392, the first clamped ends 234 and the second clamped ends 244 of each of the one or more filaments 210, and of any of the plurality of filament portions 213 as appropriate in some aspects of the present disclosure, is a crucial juncture of the surgical procedure 300, and the sequence for connecting, in the connecting-step 392, all of the first clamped ends 234 and second clamped ends 244 and any of the plurality of filament portions 213 together is critical for achieving taut connections that remain taut, and provide the desired stability and outcome for the surgical procedure 300. The one or more filaments 210 and any of the plurality of filament portions 213 comprising the craniomedial pathway 370 must, it has been found advantageous, be connected together first, before the one or more filaments 210 and any of the plurality of filament portions 213 comprising the caudolateral pathway 360. Connecting the one or more filaments 210 and any of the plurality of filament portions 213 comprising the caudolateral pathway 360 first and the one or more filaments 210 and any of the plurality of filament portions 213 comprising the craniomedial pathway 370 second will result in the craniomedial pathway 370 being lax and the entire loading pathway (both the caudolateral pathway 360 and the craniomedial pathway 370) will be loose and unstable as a result. A goal of the foregoing steps of the present disclosure is creating and maintaining isometric tension in the stifle joint 104 throughout the range of motion of the stifle joint 104, in that having the plurality of filament portions 213 remain taut is beneficial throughout the range of motion of the stifle joint 104.

Within each of the caudolateral pathway 360 and the craniomedial pathway 370, and with continued reference to FIG. 18A, FIG. 18B, FIG. 18C, FIG. 18D, FIG. 18E, FIG. 18F, FIG. 18G, and FIG. 18H, the one or more filaments 210 and any of the plurality of filament portions 213 having greater diameter (and tensile strength 212 that is greater) must, it has been found advantageous, be connected first and their placement should be towards the center. Any of the one or more filaments 210 and any of the plurality of filament portions 213 having lesser diameter (and tensile strength 212 that is lesser) must, it has been found advantageous, be connected second and their placement should be towards the periphery (i.e., more dorsal/proximal in the craniomedial pathway 370 and more ventral/distal in the caudolateral pathway 360). After all of the one or more filaments 210 and any of the plurality of filament portions 213 in the craniomedial pathway 370 have been connected, the one or more filaments 210 and any of the plurality of filament portions 213 in the caudolateral pathway 360 are then connected in the same manner.

Once all of the one or more filaments 210 and any of the plurality of filament portions 213 have been connected, the surgical wound is flushed with sterile saline.

The lateral-fabella-adjacent incision 308 in the biceps femoris muscle 150, which may be in a distal portion of the biceps femoris muscle 150, is closed with a continuous suture pattern using suitable surgical suture material, including but not limited to 2-0 Monocryl suture.

The surgical graft 304 previously undermined and harvested (comprised of the lateral subcutaneous fat and fascia tissue-fascia lata) is pulled over the connection points or lateral anchor points of the one or more filaments 210 and any of the plurality of filament portions 213.

The skin incision 302, which may be referred to as a surgical incision, is then closed in a routine fashion, closing the subcutaneous tissue and skin using the suture material and pattern (and skin staples) of the surgeon's choice.

Dead space created on the medial aspect of the stifle joint 104 is closed with a transdermal "tacking" suture using suitable surgical sutures, including but not limited to 2-0 Monocryl suture.

The surgical wound is wrapped in a sterile dressing and bandage for the first seventy-two hours after surgery.

While several variations of the present invention have been illustrated by way of example in particular embodiments, it is apparent that further embodiments could be developed within the spirit and scope of the present invention. However, it is to be expressly understood that such modifications and adaptations are within the spirit and scope of the present invention, and are inclusive, but not limited to the following appended claims as set forth. Certain aspects of the present invention were described above. From the foregoing it will be seen that this invention is one well adapted to attain all the ends and objects set forth above, together with other advantages, which are obvious in and inherent to the inventive apparatus disclosed herein. It will be understood that certain features and sub-combinations are of utility and may be employed without reference to other features and sub-combinations. It is expressly noted that the present invention is not limited to those aspects described above, but rather the intention is that additions and modifications to what was expressly described herein are also included within the scope of the invention. Moreover, it is to be understood that the features of the various aspects described herein are not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

Accordingly, what is claimed is:

1. A method for repairing an injured canine cranial cruciate ligament in a stifle, the method comprising:

drilling a first hole in a tibial tuberosity extending from a lateral side to a medial side and drilling a second hole in a tibial tuberosity extending from a lateral side to a medial side;

inserting a first needle into a lateral fabella, circumnavigating around the lateral fabella at substantially a forty-five degree angle to a horizontal plane and exiting the lateral fabella;

threading an eye of the first needle with a one or more filaments, each of the one or more filaments having a first filament-end and a second filament-end;

circumnavigating the first needle threaded with the one or more filaments around the lateral fabella at an angle substantially forty-five degrees to the horizontal plane, until the first needle and the one or more filaments can be pulled free in a lateral direction from the stifle;

cutting each of the one or more filaments within the first needle at an apex to create a third filament-end and a fourth filament-end for each of the one or more filaments;

threading a first portion of the one or more filaments through an eye of a second needle through the first filament-end and the second filament-end of each of the one or more filaments;

passing the second needle through the first hole in the tibial tuberosity from the lateral side to the medial side;

passing the second needle through the second hole in the tibial tuberosity from the medial side to the lateral side;

pairing and clasping the first filament-end and the second filament-end of each of the one or more filaments with a corresponding third filament-end and fourth filament-end of each of the one or more filaments;

threading substantially a remaining portion of the one or more filaments through the eye of the second needle through the first filament-end and second filament-end each of the one or more filaments;

passing the second needle through the first hole in the tibial tuberosity from the lateral side to the medial side;

carrying the second needle at angle between thirty to forty-five degrees through a soft fascia tissue on a medial aspect of a patella ligament, exiting and crossing over a cranial border of the patella ligament, through a fascia tissue on a lateral aspect of the patella ligament and carried through a lateral fascia of a biceps femoris muscle;

pairing and clasping the first filament-end and the second filament-end of each of the one or more filaments with the corresponding third filament-end and fourth filament-end of each of the one or more filaments, pulling the one or more filaments substantially tight; and connecting the first filament-end and the second filament-end of each of the one or more filaments with the corresponding third filament-end and fourth filament-end of each of the one or more filaments.

2. The method of claim 1, wherein the first hole is proximal to a proximal-lateral aspect of the tibial tuberosity.

3. The method of claim 1, wherein the second hole is proximal to a vertical midpoint of the tibial tuberosity.

4. The method of claim 1, wherein the one or more filaments comprise a monofilament nylon.

5. The method of claim 1, wherein the one or more filaments comprise an increased tensile strength of eight to ten times a load that comes to bear on the stifle.

6. The method of claim 1, wherein the stifle requires multiple points of failure in the one or more filaments for the stifle to fail.

7. The method of claim 1, wherein the first portion of the one or more filaments is distributed along and comprise a craniomedial pathway, distributing a load more proximally and along both a vertical plane and a horizontal plane, and wherein the one or more filaments comprising the craniomedial pathway must be connected first, and wherein the one or more filaments having a greater diameter than any other of the one or more filaments must be connected first.

8. The method of claim 7, wherein the remaining portion of the one or more filaments is distributed along and comprise a caudolateral pathway which distributes a load more distally and vertically along a lateral-vertical plane, and wherein the one or more filaments comprising the caudolateral pathway must be connected after the one or more filaments comprising the craniomedial pathway, and wherein the one or more filaments having the greater diameter than any other of the one or more filaments must be connected first.

9. The method of claim 1, wherein the second hole is approximately one to four centimeters from the first hole.

10. The method of claim 1, wherein the first hole and the second hole each comprise a diameter of approximately three to approximately six millimeters.

11. The method of claim 1, wherein each of the one or more filaments comprises a length of approximately forty-eight inches.

12. The method of claim 1, wherein a tensile strength of each of the one or more filaments is selected from a group comprising 40-pound, 60-pound, and 80-pound.

13. A method for repairing an injured canine cranial cruciate ligament in a stifle, the method comprising:

drilling a first hole in a tibial tuberosity extending from a lateral side to a medial side;

drilling a second hole in the tibial tuberosity extending from a lateral side to a medial side;

inserting a curved needle into a caudal-ventral aspect of a lateral fabella, circumnavigating around the lateral fabella at substantially a forty-five degree angle to a horizontal plane and exiting at a cranial-dorsal aspect of the lateral fabella;

threading an eye of the curved needle with a one or more filaments, each of the one or more filaments having a first filament-end and a second filament-end;

balancing a substantially equal length of each of the one or more filaments on either side of the eye of the curved needle;

circumnavigating the curved needle threaded with the one or more filaments around the lateral fabella at an angle substantially forty-five degrees to the horizontal plane, until the curved needle and the one or more filaments can be pulled free in a lateral direction from the stifle;

cutting each of the one or more filaments within the eye of the curved needle at a filament apex of each of the one or more filaments to create a third filament-end and a fourth filament-end each of the one or more filaments;

threading substantially a first half of the one or more filaments through an eye of a substantially straight needle, such that the first filament-end and the second filament-end of each of the one or more filaments are approximately near each other;

passing the substantially straight needle through the first hole in the tibial tuberosity from the lateral side to the medial side;

passing the substantially straight needle through the second hole in the tibial tuberosity from the medial side to the lateral side;

pairing and clasping the first filament-end and the second filament-end of each of the one or more filaments with a corresponding third filament-end and fourth filament-end of each of the one or more filaments;

threading substantially a second half of the one or more filaments through the eye of the substantially straight needle through the first filament-end and the second filament-end of each of the one or more filaments;

passing the substantially straight needle through the first hole in the tibial tuberosity from the lateral side to the medial side;

carrying the substantially straight needle at angle between thirty to forty-five degrees through a soft fascia tissue on a medial aspect of a patella ligament, exiting and crossing over a cranial border of the patella ligament, through a fascia tissue on a lateral aspect of the patella ligament and carried through a lateral fascia of a biceps femoris muscle;

pairing and clasping the first filament-end and the second filament-end of each of the one or more filaments with the corresponding third filament-end and fourth filament-end of each of the one or more filaments;

pulling the one or more filaments substantially tight; connecting the first filament-end and second filament-end of each of the one or more filaments with the corresponding third filament-end and fourth filament end of each of the one or more filaments; wherein the first half of the one or more filaments is distributed along and comprise a craniomedial pathway, distributing a load more proximally and along both a vertical plane and a horizontal plane, and wherein the one or more filaments comprising the craniomedial pathway must be connected first, and wherein the second half of the one or more filaments is distributed along and comprise a caudolateral pathway, distributing a load more distally and vertically along a lateral-vertical plane, and wherein the one or more filaments comprising the caudolateral pathway must be connected after the one or more filaments comprising the craniomedial pathway, and wherein within each of the craniomedial pathway and the caudolateral pathway, the one or more filaments having a greater diameter than any other of the one or more filaments must be connected first.

14. A method for repairing an injured canine cranial cruciate ligament in a stifle, the method comprising:
drilling a first hole in a tibial tuberosity extending from a lateral side to a medial side;
drilling a second hole in the tibial tuberosity extending from a lateral side to a medial side;
exposing a lateral fabella from a biceps femoris muscle;
inserting a curved elongated eye stacking needle into caudal-ventral aspect of the lateral fabella, circumnavigating around the lateral fabella at substantially a forty-five degree angle to a horizontal plane and exiting at a cranial-dorsal aspect of the lateral fabella;
holding a needle point of the curved elongated eye stacking needle;
holding another end of the curved elongated eye stacking needle, proximate to an eye of the curved elongated eye stacking needle;
threading the eye of the curved elongated eye stacking needle with a one or more filaments, wherein the one or more filaments are vertically stacked within the eye of the curved elongated eye stacking needle;
balancing a substantially equal length of each of the one or more filaments on either side of the eye of the curved elongated eye stacking needle;
clasping a first filament-end and a second filament-end each of the one or more filaments;
circumnavigating the curved elongated eye stacking needle threaded with the one or more filaments around the lateral fabella at an angle substantially forty-five degrees to the horizontal plane, until the curved elongated eye stacking needle and the one or more filaments can be pulled free in a lateral direction from the stifle;
cutting each of the one or more filaments within the eye of the curved elongated eye stacking needle at a filament apex to create a third filament-end and a fourth filament-end of each of the one or more filaments;
clasping the third filament-end and fourth filament-end of each of the one or more filaments;
threading substantially a first half of the one or more filaments through an eye of a straight elongated eye stacking needle, such that the first filament-end and the second filament-end of each of the one or more filaments are approximately near each other;
passing the straight elongated eye stacking needle through the first hole in the tibial tuberosity from the lateral side to the medial side;
passing the straight elongated eye stacking needle through the second hole in the tibial tuberosity from the medial side to the lateral side;
pairing and clasping the first filament-end and the second filament-end of each of the one or more filaments with a corresponding third filament-end and fourth filament-end of each of the one or more filaments;
threading substantially a second half of the one or more filaments through the eye of the straight elongated eye stacking needle through the first filament-end and the second filament-end of each of the one or more filaments;
passing the straight elongated eye stacking needle through the first hole in the tibial tuberosity from the lateral side to the medial side;
carrying the straight elongated eye stacking needle at angle between thirty to forty-five degrees through a soft fascia tissue on a medial aspect of a patella ligament, exiting and crossing over a cranial border of the patella ligament, through a fascia tissue on a lateral aspect of the patella ligament and carried through a lateral fascia of a biceps femoris muscle;
pairing and clasping the first filament-end and the second filament-end of each of the one or more filaments with the corresponding third filament-end and fourth filament-end of each of the one or more filaments;
connecting the first filament-end and the second filament-end of each of the one or more filaments with the corresponding third filament-end and fourth filament-end of each of the one or more filaments.

15. The method of claim 14, wherein the first half of the one or more filaments is distributed along and comprise a craniomedial pathway, distributing a load more proximally and along both a vertical plane and a horizontal plane, and wherein the one or more filaments comprising the craniomedial pathway must be connected first, and wherein the one or more filaments having a greater diameter than any other of the one or more filaments must be connected first.

16. The method of claim 15, wherein the second half of the one or more filaments is distributed along and comprise a caudolateral pathway, distributing a load more distally and vertically along a lateral-vertical plane, and wherein the one or more filaments comprising the caudolateral pathway must be connected after the one or more filaments comprising the craniomedial pathway, and wherein the one or more filaments having the greater diameter than any other of the one or more filaments must be connected first.

* * * * *